(12) United States Patent
Palomer Benet et al.

(10) Patent No.: US 10,919,851 B2
(45) Date of Patent: Feb. 16, 2021

(54) 2-PYRROLIDINE PHENYLHYDRAZIDES ANTIBACTERIAL AGENTS

(71) Applicant: ABAC THERAPEUTICS, S.L, Esplugues de Llobregat (ES)

(72) Inventors: Albert Palomer Benet, Barcelona (ES); Domingo Gargallo Viola, Cornellà de Llobregat (ES)

(73) Assignee: ABAC THERAPEUTICS, S.L., Esplugues de Llobregat (ES)

( * ) Notice: Subject to any disclaimer, the term of this patent is extended or adjusted under 35 U.S.C. 154(b) by 0 days.

(21) Appl. No.: 16/320,929

(22) PCT Filed: Jul. 28, 2017

(86) PCT No.: PCT/EP2017/069179
§ 371 (c)(1),
(2) Date: Jan. 25, 2019

(87) PCT Pub. No.: WO2018/020004
PCT Pub. Date: Feb. 1, 2018

(65) Prior Publication Data
US 2019/0177272 A1    Jun. 13, 2019

(30) Foreign Application Priority Data

| Jul. 29, 2016 | (EP) | 16181965 |
| Mar. 8, 2017 | (EP) | 17159942 |
| Mar. 28, 2017 | (EP) | 17163270 |
| Mar. 30, 2017 | (ES) | 201700452 |

(51) Int. Cl.
| C07D 207/09 | (2006.01) |
| C07D 207/46 | (2006.01) |
| C07D 207/50 | (2006.01) |
| C07D 211/36 | (2006.01) |
| C07D 211/40 | (2006.01) |
| C07D 211/94 | (2006.01) |
| C07D 403/06 | (2006.01) |
| C07D 403/12 | (2006.01) |
| C07D 405/12 | (2006.01) |
| C07D 413/06 | (2006.01) |
| A61P 31/04 | (2006.01) |
| A61K 31/40 | (2006.01) |
| A61K 31/4025 | (2006.01) |
| A61K 45/06 | (2006.01) |

(52) U.S. Cl.
CPC ............ *C07D 207/09* (2013.01); *A61K 31/40* (2013.01); *A61K 31/4025* (2013.01); *A61K 45/06* (2013.01); *A61P 31/04* (2018.01); *C07D 207/46* (2013.01); *C07D 207/50* (2013.01); *C07D 211/36* (2013.01); *C07D 211/40* (2013.01); *C07D 211/94* (2013.01); *C07D 403/06* (2013.01); *C07D 403/12* (2013.01); *C07D 405/12* (2013.01); *C07D 413/06* (2013.01)

(58) Field of Classification Search
CPC .. C07D 207/09; C07D 207/46; C07D 207/50; C07D 211/36; C07D 211/40; C07D 211/94; C07D 403/06; C07D 403/12; C07D 405/12; C07D 413/06
See application file for complete search history.

(56) References Cited

U.S. PATENT DOCUMENTS

2013/0018079 A1    1/2013    Weibel et al.

FOREIGN PATENT DOCUMENTS

| CN | 101525336 A | 9/2009 |
| EP | 2100602 A1 | 9/2009 |
| GB | 769482 | 3/1957 |
| WO | WO 2012/051708 A1 | 4/2012 |
| WO | WO 2013/153394 A1 | 10/2013 |
| WO | WO 2016/0169291 A1 | 2/2016 |

OTHER PUBLICATIONS

International Search Report and Written Opinion dated Oct. 4, 2017 for PCT/EP2017/069179, 15 pages.
Greene, et al. "Protective Groups in Organic Synthesis", Third Edition, John Wiley & Sons, Inc., New York, 1999.
Giamarellou, et al. "*Acinetobacter baumannii*: a universal threat to public health?", International Journal of Antimicrobial Agents, 2008, vol. 32, No. 2, pp. 106-109.
Jernberg, et al. "Long-term impacts of antibiotic exposure on the human intestinal microbiota", Microbiology 2010, vol. 156, pp. 3216-3223.

(Continued)

*Primary Examiner* — Rebecca L Anderson
(74) *Attorney, Agent, or Firm* — Squire Patton Boggs (US) LLP

(57) ABSTRACT

2-Pyrrolidine phenylhydrazides antibacterial agents The present invention relates to 2-pyrrolidine phenylhydrazide compounds of formula (I), which are selective antibacterials specifically against *Acinetobacter baumannii*. The invention also relates to their therapeutic use as antibacterials, to a process for their preparation and to pharmaceutical compositions containing them.

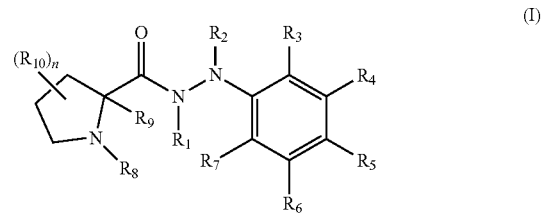

(I)

19 Claims, No Drawings

(56) References Cited

OTHER PUBLICATIONS

Liu, et al. "Structure-based design of novel class II c-Met inhibitors: 2. SAR and Kinase electivity profiles of the pyrazolone series", The Journal of Medicinal Chemistry, Mar. 8, 2012, vol. 55, No. 5, pp. 1868-1897.
Cockerill, et al. "Methods for Dilution Antimicrobial Susceptibility Tests for Bacteria That Grow Aerobically; Approved Standard—Novena Edition", Clinical and Laboratory Standards Institute, M07-A9, vol. 32, No. 2, Jan. 2012.
"Remington: The Science and Practice of Pharmacy, $20^{th}$ Edition", Lippincott, Wiliams & Wilkins, Philadelphia 2000, [ISBN: 0-683-306472].
Rowe, et al. "Handbook of Pharmaceutical Excipients, $6^{th}$ Edition", Pharmaceutical Press, London 2009, [ISBN: 9780853697923].
Villarreal, et al. "Use of broad-spectrum antibiotics and the development of irritable bowel syndrome", WMJ 2012, vol. 111, No. 1, pp. 17-20.
Volkert, et al. "Phenylhydrazide as an Enzyme-Labile Protecting Group in Peptide Synthesis", The Journal of Organic Chemistry, Oct. 1, 2002, vol. 67, No. 20, pp. 6902-6910.
Wintersdorff, et al. "Dissemination of Antimicrobial Resistance in Microbial Ecosystems through Horizontal Gene Transfer", Frontiers in Microbiology, Feb. 19, 2016, vol. 7, Article 173, pp. 1-10.

2-PYRROLIDINE PHENYLHYDRAZIDES ANTIBACTERIAL AGENTS

This application claims the benefit of the European Patent Application EP16181965.1 filed on Jul. 29, 2016, the European Patent Application EP17159942.6 filed on Mar. 8, 2017, the European Patent Application EP17163270.6 filed on Mar. 28, 2017 and the Spanish Patent Application ES 201700452 filed on Mar. 30, 2017.

TECHNICAL FIELD

The present invention relates to new antibacterial agents, particularly to 2-pyrrolidine phenylhydrazide compounds that show selective antibacterial activity against the Gram-negative bacteria *Acinetobacter baumannii*.

BACKGROUND ART

Infections caused by *Acinetobacter baumannii* (*A. baumannii*) bacteria are increasingly recognized as a serious health threat, especially in healthcare facilities, and are associated with increased morbidity, mortality and duration of hospital stay, as well as with high healthcare costs (Giamarellou et al. *Acinetobacter baumannii: a universal threat to public health?* Int. J. Antimicrob. Agents, 2008, 32(2), 106-9; Howard et al. *Acinetobacter baumannii. An emerging opportunistic pathogen.* Virulence 2012, 3(3), 243-250).

*A. baumannii* is a rod-shaped Gram-negative bacillus that is aerobic, and non-motile. It behaves as an opportunistic pathogen mainly affecting immunocompromised subjects, for example those having an underlying disease, such as chronic lung disease or diabetes, and those hospitalized for long periods and subjected to multiple invasive procedures.

*A. baumannii* is often implicated in nosocomial infections, so it has a high incidence among patients experiencing prolonged hospital stay, and is a particularly relevant source of infections in hospital intensive care units (ICUs). Among the main risk factors for acquiring *A. baumannii* is the use of artificial devices commonly employed in hospital settings, such as dialysis, mechanical ventilation, sutures or catheters, due to the notorious ability of *A. baumannii* to survive for extended periods on environmental surfaces.

*A. baumannii* can cause infections in virtually every organ system of the human body, including pneumonia, surgical site infections, skin and soft tissue infections, urinary tract infections, post-operative meningitis and catheter-related infections.

Hospital-acquired pneumonia is the most common life-threatening hospital-acquired infection, and is mainly associated with the use of mechanical ventilation, known as ventilator associated pneumonia (VAP). VAP infections caused by *Acinetobacter* are between 8% and 35% of total VAP cases.

Bloodstream infections (BSI) are also common nosocomial infections, which are also associated with increased morbidity, mortality and duration of hospital stay. Infections caused by *Acinetobacter* correspond to 2% of the total BSI cases, with a particular high incidence in ICU-acquired BSI.

Other reported hospital-acquired infections associated with *A. baumannii* are, for example, surgical site infections (SSI) and urinary tract infections, such as catheter-associated urinary tract infections (CAUTI) or hospitalized community-acquired urinary tract infections.

*A. baumannii* infections are currently treated with different broad- or semi-broad spectrum antibiotics or combinations, including, for example, the carbapenems imipenem, meropenem and doripenem, which are first choice drugs. However, treatment of *A. baumannii* infections is challenging since it has emerged as a highly drug-resistant pathogen, especially carbapenem-resistant, and therefore other alternative broad-spectrum antibacterials are also used in therapy, such as polymyxins (colistin, polymyxin E and polymyxin B), tigecycline, tetracyclines (minocycline and doxycycline) or aminoglycosides (amikacin and tobramycin). None of the currently used treatments are specific for *A. baumannii*.

The use of such broad-spectrum antibacterials entails important drawbacks, since they have a substantial impact on the normal flora, potentially diminishing the immunologic function of microbiota and potentially generating treatment-induced co-infections caused by resistant strains, as disclosed for example in Jernberg et al. *Long-term impacts of antibiotic exposure on the human intestinal microbiota*, Microbiology, 2010, 156(Pt 11), 3216-3223.

Moreover, in a retrospective study performed with 26, 107 patients, it was concluded that the use of broad-spectrum antibiotics may have a relationship with the development of irritable bowel syndrome (IBS), as disclosed in Villarreal et al. *Use of broad-spectrum antibiotics and the development of irritable bowel syndrome*, WMJ, 2012, 111(1), 17-20.

As previously commented, when broad-spectrum antibiotics are used, not only the pathogenic microorganism, but any other microorganisms present in the treated subject (be either human or animal) may develop resistance. This latter may happen if antibiotic is moderately active but not lethal for it. Moreover, it is known in the art that when a microorganism develops a resistance to a drug is able to transfer such resistance to other members of its specie or even transfer this resistance to other species, this is known as Horizontal Gene Transfer (HGT), as disclosed in Wintersdorff, et al. *Dissemination of Antimicrobial Resistance in Microbial Ecosystems through Horizontal Gene Transfer*, Front Microbiol. 2016, 7:173. Consequently, it is an advantage of pathogen-specific treatment that generation of resistance in the pathogenic species does not happen by this two-stage process, namely, first producing in other microorganisms and then transfer by HGT to pathogenic species.

In contrast, treatments using pathogen-specific antibacterials that kill exclusively the infecting bacteria would minimize the impact on normal flora and would avoid the selection of resistant strains of non-infecting bacteria of microbiota, thus minimizing any treatment-induced co-morbidities and reducing the Horizontal Gene Transfer of resistance between species.

The only antibacterial agents selective for *Acinetobacter baumannii* disclosed so far in the state of the art are a series of arylhydrazides containing a 2-pyridone moiety, as disclosed in the international patent application WO2016/016291-A1.

GB769482A discloses thiazolecarboxylic acid hydrazide as an antibacterial.

WO2013/153394 discloses compounds which can be arylhydrazides substituted by quinolones, as antibacterials.

WO2012/051708 discloses antibiotic compounds being phenylhydrazides substituted by bicycle-methyl (including indolyl-methyl).

Therefore, it would be desirable to provide novel compounds which are selective antibacterial agents against *Acinetobacter baumannii* bacteria, to thus increase the number of selective drugs currently available, which are both effective for treating the life-threatening infections caused by *A. baumannii* and highly selective for this bacteria, in order to avoid the disadvantages associated to the non-selective broad-spectrum antibiotics currently used in therapy.

OBJECT OF THE INVENTION

The object of the present invention is a compound of formula (I) as defined below.

A second aspect of the present invention relates to the compound of formula (I) for use as a medicament.

A third aspect of the present invention relates to a compound of formula (I) for use as antibacterial agent, particularly for treating or preventing *A. baumannii* infections.

A fourth aspect of the present invention relates to a pharmaceutical composition comprising a compound of formula (I) and at least one pharmaceutically acceptable excipient and/or carrier.

A fifth aspect of the present invention relates to a process for preparing compounds of formula (I).

DETAILED DESCRIPTION OF THE INVENTION

In a first aspect, the present invention relates to a compound of formula (I):

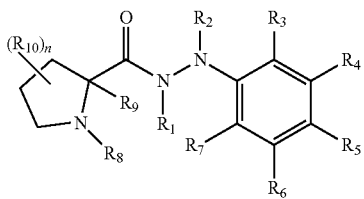

(I)

or a pharmaceutically acceptable salt or solvate thereof, wherein $R_1$ and $R_2$ are independently selected from hydrogen, $C_{1-4}$alkyl, halo$C_{1-4}$alkyl and hydroxy$C_{1-4}$alkyl;

$R_3$, $R_4$, $R_5$, $R_6$ and $R_7$ are independently selected from hydrogen, —OH, halogen, $C_{1-6}$alkoxy, halo$C_{1-4}$alkoxy, —O$C_{3-6}$cycloalkyl$C_{0-4}$alkyl, $C_{1-6}$alkyl, $C_{3-6}$cycloalkyl$C_{0-4}$alkyl, halo$C_{1-6}$alkyl, hydroxy$C_{1-6}$alkyl, $C_{1-4}$alkoxy$C_{1-6}$alkyl, $C_{1-4}$alkoxy$C_{1-4}$alkoxy, —OCOR$_{11}$, —OS(O$_2$)R$_{11}$, —NR$_{11}$R$_{12}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CONR$_{11}$R$_{12}$, —S(O$_2$)NR$_{11}$R$_{12}$, —S(O$_2$)R$_{11}$, —CN and —CO$_2$R$_{11}$; or two of $R_3$ to $R_7$ attached to adjacent carbon atoms are connected to form a 5- or 6-membered cycloalkyl, wherein 1 or 2 methylene groups of the cycloalkyl may be replaced by O, said cycloalkyl can be optionally substituted by one or more $C_{1-4}$alkyl or halo$C_{1-4}$alkyl;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, $C_{2-5}$acyl, —C(O)$C_{3-6}$cycloalkyl$C_{0-2}$alkyl, —CONR$_{13}$R$_{14}$, —C(NR$_{15}$)NR$_{11}$R$_{12}$ and —CO$_2$R$_{11}$;

$R_9$ is selected from hydrogen, $C_{1-4}$alkyl and halo$C_{1-4}$alkyl;

n is 0, 1, 2 or 3;

each $R_{10}$, if present, is independently selected from —OH, halogen, $C_{1-6}$alkyl, halo$C_{1-6}$alkyl, $C_{1-6}$alkoxy, $C_{1-4}$alkoxy$C_{1-6}$alkyl, —O$C_{3-6}$cycloalkyl$C_{0-4}$alkyl, —SR$_{11}$, —NR$_{11}$R$_{12}$, —OCOR$_{11}$, —OS(O$_2$)R$_{11}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CN, phenyl, 5- or 6-membered heteroaryl ring comprising 1 or 2 heteroatoms selected from N, O and S; wherein said phenyl and said heteroaryl ring may be optionally substituted by one or more $C_{1-4}$alkyl or halo$C_{1-4}$alkyl; or two $R_{10}$ attached to a common carbon atom form an oxo; or two $R_{10}$ attached to a common carbon atom form a spiro $C_{3-6}$cycloalkyl, or two $R_{10}$ attached to adjacent carbon atoms are connected to form a 3- to 6-membered cycloalkyl, said cycloalkyl can be optionally substituted by one or more substituents independently selected from $C_{1-4}$alkyl, halo$C_{1-4}$alkyl and halogen;

each $R_{11}$ and $R_{12}$ are independently selected from hydrogen, $C_{1-4}$alkyl, halo$C_{1-4}$alkyl and $C_{3-6}$cycloalkyl$C_{0-4}$alkyl;

each $R_{13}$ and $R_{14}$ are independently selected from hydrogen, $C_{1-4}$alkyl, $C_{3-6}$cycloalkyl$C_{0-4}$alkyl and Het$_{3-6}$, wherein each $C_{1-4}$alkyl and $C_{3-6}$cycloalkyl$C_{0-4}$alkyl may optionally be substituted by one or more $R_{16}$, and wherein each $C_{1-4}$alkyl may optionally be substituted by one or more Het$_{3-6}$; or $R_{13}$ and $R_{14}$ form, together with the N atom to which they are attached, a 4- to 6-membered saturated heterocycle, which can optionally contain one additional heteroatom selected from N, S and O, said heterocycle can be optionally substituted by one or more substituents independently selected from $C_{1-4}$alkyl, halo$C_{1-4}$alkyl and $C_{2-5}$acyl;

$R_{15}$ is selected from hydrogen, $C_{1-6}$alkyl, halo$C_{1-6}$alkyl, —CN, —CONR$_{11}$R$_{12}$, —S(O$_2$)R$_{11}$, —SOR$_{11}$ and —S(O$_2$)NR$_{11}$R$_{12}$;

each $R_{16}$ is independently selected from alkyl, halogen, —CN, —CO$_2$R$_{11}$, —OR$_{11}$, —SR$_{11}$, —NR$_{17}$R$_{18}$, —CONR$_{17}$R$_{18}$ and —OCOR$_{11}$;

Het$_{3-6}$ is a 3- to 6-membered saturated monocyclic heterocyclic ring containing one heteroatom selected from O, S and N, wherein said ring is bonded to the rest of the molecule through any available C atom and wherein said ring can be optionally substituted by one or more substituents independently selected from $C_{1-4}$alkyl or halo$C_{1-4}$alkyl; and each $R_{17}$ and $R_{18}$ are independently selected from hydrogen, $C_{1-4}$alkyl and halo$C_{1-4}$alkyl, or $R_{17}$ and $R_{18}$ form, together with the N atom to which they are attached, a 4- to 6-membered saturated heterocycle, which can optionally contain one additional heteroatom selected from N, S and O, said heterocycle can be optionally substituted by one or more substituents independently selected from $C_{1-4}$alkyl and halo$C_{1-4}$alkyl;

and wherein the following products are excluded:

1,2-pyrrolidinedicarboxylic acid, 1-(1,1-dimethylethyl) ester, 2-(2-phenylhydrazide), (2S)—, 1,2-pyrrolidinedicarboxylic acid, 1-(1,1-dimethylethyl) ester, 2-(1-methyl-2-phenylhydrazide), (2S)—, 1,2-pyrrolidinedicarboxylic acid, 4-mercapto-, 1-(1,1-dimethylethyl) ester, 2-[2-[3-(aminosulfonyl)phenyl]hydrazide], (2S,4S)—, 1,2-pyrrolidinedicarboxylic acid, 4-mercapto-, 1-(1,1-dimethylethyl) ester, 2-[2-(3-carboxyphenyl)hydrazide], (2S, 4S)—, 1,2-pyrrolidinedicarboxylic acid, 4-mercapto-, 1-(1,1-dimethylethyl) ester, 2-[2-[2-(trifluoromethyl)phenyl]hydrazide], (2S,4S)—, and 1,2-pyrrolidinedicarboxylic acid, 4-mercapto-, 1-(1,1-dimethylethyl) ester, 2-[2-[2-chloro-5-(trifluoromethyl)phenyl]hydrazide], (2S,4S)—.

The authors of the present invention have developed a group of phenylhydrazide compounds containing a 2-pyrrolidine moiety as depicted in formula (I) that, surprisingly, show selective antibacterial activity against the Gram-negative bacteria *Acinetobacter baumannii* (*A. baumannii*), providing therefore a new and safer therapeutic tool for treating the infections caused by this bacteria, while avoiding the damage to the intestinal flora and multiple resistances involved with the treatment with the broad-spectrum antibacterials.

Moreover, not only the compounds of formula (I) are highly active and selective antibacterials against *A. baumannii*, as determined in in vitro assays, but they are also highly stable in blood plasma, so they are expected to maintain their antibacterial activity in vivo, as well.

The following compounds are excluded from the first aspect of the present invention:

1,2-pyrrolidinedicarboxylic acid, 1-(1,1-dimethylethyl) ester, 2-(2-phenylhydrazide), (2S)— (CAS 474316-85-3)

1,2-Pyrrolidinedicarboxylic acid, 1-(1,1-dimethylethyl) ester, 2-(1-methyl-2-phenylhydrazide), (2S)— (CAS1361235-82-6)

1,2-Pyrrolidinedicarboxylic acid, 4-mercapto-, 1-(1,1-dimethylethyl) ester, 2-[2-[3-(aminosulfonyl)phenyl]hydrazide], (2S,4S)— (CAS1188957-98-3)

1,2-Pyrrolidinedicarboxylic acid, 4-mercapto-, 1-(1,1-dimethylethyl) ester, 2-[2-(3-carboxyphenyl)hydrazide], (2S,4S)— (CAS1188958-01-1)

1,2-Pyrrolidinedicarboxylic acid, 4-mercapto-, 1-(1,1-dimethylethyl) ester, 2-[2-[2-(trifluoromethyl)phenyl]hydrazide], (2S,4S)— (CAS1188958-02-2)

1,2-Pyrrolidinedicarboxylic acid, 4-mercapto-, 1-(1,1-dimethylethyl) ester, 2-[2-[2-chloro-5-(trifluoromethyl)phenyl]hydrazide], (2S,4S)— (CAS1188958-04-4)

These compounds have been disclosed in the following prior art documents: Liu et al., J. Med. Chem., 2012, 55(5), 1868-1897 (compounds 474316-85-3 and 1361235-82-6) and CN101525336-A (compounds 1188957-98-3, 1188958-01-1, 1188958-02-2 and 1188958-04-4). These compounds are disclosed only as reaction intermediates, but their medical use is not disclosed or suggested in the prior art.

Definitions

Within the meaning of the present invention, the term $C_{1-6}$alkyl, as a group or part of a group, means a straight or branched alkyl chain which contains from 1 to 6 carbon atoms and includes, among others, the groups methyl, ethyl, n-propyl, isopropyl, n-butyl, isobutyl, sec-butyl, tert-butyl, n-pentyl, isopentyl or n-hexyl. Similarly, the term $C_{1-4}$alkyl, as a group or part of a group, means a straight or branched alkyl chain which contains from 1 to 4 carbon atoms and is a subgroup of $C_{1-6}$alkyl which includes the groups methyl, ethyl, n-propyl, isopropyl, n-butyl, isobutyl, sec-butyl and tert-butyl. Similarly, the term $C_{1-2}$alkyl means an alkyl chain which contains 1 or 2 carbon atoms and includes the groups methyl and ethyl.

Halogen or its abbreviation halo means fluoro, chloro, bromo or iodo.

A halo$C_{1-6}$alkyl group means a group resulting from the replacement of one or more hydrogen atoms from a $C_{1-6}$alkyl group with one or more halogen atoms (i.e. fluoro, chloro, bromo or iodo), which can be the same or different. Examples include, among others, the groups fluoromethyl, difluoromethyl, trifluoromethyl, chloromethyl, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2-fluoropropyl, 3-fluoropropyl, 2,2-difluoropropyl, 2,3-difluoropropyl, 2-chloropropyl, 3-chloropropyl, 2,3-dichloropropyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl. Similarly, the halo$C_{1-4}$alkyl group means a group resulting from the replacement of one or more hydrogen atoms from a $C_{1-4}$alkyl group with one or more halogen atoms (i.e. fluoro, chloro, bromo or iodo), which can be the same or different, and is a subgroup of halo$C_{1-4}$alkyl. Examples include, among others, the groups fluoromethyl, difluoromethyl, trifluoromethyl, chloromethyl, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2-fluoropropyl, 3-fluoropropyl, 2,2-difluoropropyl, 2,3-difluoropropyl, 2-chloropropyl, 3-chloropropyl, 2,3-dichloropropyl, 4-fluorobutyl, 4-chlorobutyl, 4-bromobutyl and nonafluorobutyl.

A hydroxy$C_{1-6}$alkyl group means a group resulting from the replacement of one or more hydrogen atoms from a $C_{1-6}$alkyl group with one or more hydroxy groups. Examples include, among others, the groups hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl, 1-hydroxybutyl, 5-hydroxypentyl, 4-hydroxypentyl, 3-hydroxypentyl, 2-hydroxypentyl, 1-hydroxypentyl, 6-hydroxyhexyl, 5-hydroxyhexyl, 4-hydroxyhexyl, 3-hydroxyhexyl, 2-hydroxyhexyl, and 1-hydroxyhexyl. Similarly, a hydroxy$C_{1-4}$alkyl group means a group resulting from the replacement of one or more hydrogen atoms from a $C_{1-4}$alkyl group with one or more hydroxy groups, and is a subgroup of the hydroxy$C_{1-6}$alkyl group. Examples of hydroxy$C_{1-4}$alkyl group include, for example, hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl and 1-hydroxybutyl.

A $C_{2-5}$acyl group means a group of formula —C(O)$C_{1-4}$alkyl, wherein the $C_{1-4}$alkyl moiety has the same meaning as described above. Examples include, among other, acetyl, propanoyl, n-butanoyl, sec-butanoyl, tert-butanoyl, or n-pentanoyl. Similarly, a $C_{2-3}$acyl group means a group of formula —C(O)$C_{1-2}$alkyl, wherein the $C_{1-2}$alkyl moiety has the same meaning as described above. Examples include acetyl and propanoyl.

A $C_{1-6}$alkoxy group, as a group or part of a group, means a group of formula —O$C_{1-6}$alkyl, wherein the $C_{1-6}$alkyl moiety has the same meaning as described above. Examples include methoxy, ethoxy, propoxy, isopropoxy, n-butoxy, isobutoxy, sec-butoxy, tert-butoxy, n-pentoxy, isopentoxy, neopentoxy, or n-hexoxy, among others. Similarly, a $C_{1-4}$alkoxy group, as a group or part of a group, means a group of formula —O$C_{1-4}$alkyl, wherein the $C_{1-4}$alkyl moiety has the same meaning as described above and is a subgroup of the $C_{1-6}$alkoxy which includes, for example, methoxy, ethoxy, propoxy, isopropoxy, n-butoxy, isobutoxy, sec-butoxy and tert-butoxy.

A $C_{1-4}$alkoxy$C_{1-4}$alkoxy group means a group resulting from the replacement of one hydrogen atom from a $C_{1-4}$alkoxy group with one $C_{1-4}$alkoxy group, as defined above. Examples include, among others, methoxymethoxy, methoxy-1-ethoxy, methoxy-2-ethoxy, ethoxymethoxy, ethoxy-1-ethoxy, ethoxy-2-ethoxy, methoxy-3-propoxy, ethoxy-3-propoxy, and propoxy-3-propoxy.

A halo$C_{1-4}$alkoxy group means a group resulting from the replacement of one or more hydrogen atoms from a $C_{1-4}$alkoxy group with one or more halogen atoms (i.e. fluoro, chloro, bromo or iodo), which can be the same or different. Examples include, among others, the groups fluoromethoxy, difluoromethoxy, trifluoromethoxy, chloromethoxy, dichloromethoxy, trichloromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 4-fluorobutoxy, 4-chlorobutoxy, 4-bromobutoxy or nonafluorobutoxy.

A $C_{1-4}$alkoxy$C_{1-6}$alkyl group means a group resulting from the replacement of one or more hydrogen atoms from a $C_{1-6}$alkyl group with one or more $C_{1-4}$alkoxy groups as defined above, which can be the same or different. Examples include, among others, the groups methoxymethyl, ethoxymethyl, propoxymethyl, isopropoxymethyl, butoxymethyl, isobutoxymethyl, sec-butoxymethyl, tert-butoxymethyl, dimethoxymethyl, 1-methoxyethyl, 2-methoxyethyl, 2-ethoxyethyl, 1,2-diethoxyethyl, 1-butoxyethyl, 2-sec-butoxyethyl, 3-methoxypropyl, 2-butoxypropyl, 1-methoxy-2-ethoxypropyl, 3-tert-butoxypropyl, 4-methoxybutyl, 5-methoxypentyl, 4-ethoxypentyl and 2-methoxy-3-methylpenyl. Similarly, a $C_{1-4}$alkoxy$C_{1-4}$alkyl group means a group resulting from the replacement of one or more hydrogen atoms from a $C_{1-4}$alkyl group with one or more $C_{1-4}$alkoxy groups as defined above, and is a subgroup of the $C_{1-4}$alkoxy$C_{1-6}$alkyl group. Examples of $C_{1-4}$alkoxy$C_{1-4}$alkyl include, among others, methoxymethyl, ethoxymethyl, propoxymethyl, isopropoxymethyl, butoxymethyl, isobutoxymethyl, sec-butoxymethyl, tert-butoxymethyl, dimethoxymethyl, 1-methoxyethyl, 2-methoxyethyl, 2-ethoxyethyl, 1,2-diethoxyethyl, 1-butoxyethyl, 2-sec-butoxyethyl, 3-methoxypropyl, 2-butoxypropyl, 1-methoxy-2-ethoxypropyl, 3-tert-butoxypropyl and 4-methoxybutyl.

A $C_{3-6}$cycloalkyl group, as a group or as a part of a group, means a saturated, monocyclic, hydrocarbon ring group comprising 3 to 6 carbon atoms, which can be optionally substituted by one or more substituents independently selected from $C_{1-4}$alkyl, $C_{1-4}$alkoxy and halogen, i.e., one or more hydrogen atoms of the ring can be replaced by a $C_{1-4}$alkyl, a $C_{1-4}$alcoxy or a halogen. When there is more than one substitution, the substituents can be the same or different. Examples of $C_{3-6}$cycloalkyl groups include, for example, cyclopropyl, cyclobutyl, cyclopentyl and cyclohexyl.

A $C_{3-6}$cycloalkyl$C_{1-4}$alkyl group, as a group or as a part of a group, means a group resulting from the replacement of one hydrogen atom from a $C_{1-4}$alkyl group with one $C_{3-6}$cycloalkyl group, as defined above. Examples include, among others, cyclopropylmethyl, cyclobutylmethyl, cyclopentylmethyl, cyclohexylmethyl, cyclopropylethyl, 2-cyclopropylpropyl, 3-cyclopentylpropyl and 4-cyclopentylbutan-2-yl. Similarly, a $C_{3-6}$cycloalkyl$C_{1-2}$alkyl group, as a group or as a part of a group, means a group resulting from the replacement of one hydrogen atom from a $C_{1-2}$alkyl group with one $C_{3-6}$cycloalkyl group, as defined above, and is a subgroup of the $C_{3-6}$cycloalkyl$C_{1-4}$alkyl group, including among other the following examples: cyclopropylmethyl, cyclobutylmethyl, cyclopentylmethyl, cyclohexylmethyl, cyclopropylethyl, cyclobutylethyl, cyclopentylethyl, and cyclohexylethyl. Thus, for example, the —C(O)$C_{3-6}$cycloalkyl$C_{1-2}$alkyl group means a group resulting from the replacement of one hydrogen atom from a —C(O)$C_{1-2}$alkyl group with one $C_{3-6}$cycloalkyl group. Analogously, the —O$C_{3-6}$cycloalkyl$C_{1-4}$alkyl group means a group resulting from the replacement of one hydrogen atom from a —O$C_{1-4}$alkyl group with one $C_{3-6}$cycloalkyl group.

The term $C_0$alkyl indicates that the alkyl group is absent. Thus, for example, the term $C_{3-6}$cycloalkyl$C_{0-4}$alkyl includes $C_{3-6}$cycloalkyl and $C_{3-6}$cycloalkyl$C_{1-4}$alkyl, as defined above, and the term $C_{3-6}$cycloalkyl$C_{0-2}$alkyl includes $C_{3-6}$cycloalkyl and $C_{3-6}$cycloalkyl$C_{1-2}$alkyl. Analogously, the term—C(O)$C_{3-6}$cycloalkyl$C_{0-2}$alkyl includes —C(O)$C_{3-6}$cycloalkyl and —C(O)$C_{3-6}$cycloalkyl$C_{1-2}$alkyl and the term —O$C_{3-6}$cycloalkyl$C_{0-4}$alkyl includes —O$C_{3-6}$cycloalkyl and —O$C_{3-6}$cycloalkyl$C_{1-4}$alkyl.

Likewise, the term $C_{1-4}$alkoxy$C_{0-6}$alkyl includes $C_{1-4}$alkoxy and $C_{1-4}$alkoxy$C_{1-6}$alkyl as defined above.

An "oxo" group means =O.

A "methylene" group means —$CH_2$—.

The term "saturated" relates to groups that do not have any double or triple bonds.

Any carbon atom as well as any heteroatom with unsatisfied valences in the formulas and schemes depicted in the present description is assumed to have the sufficient number of hydrogen atoms to satisfy the valences.

The expression "optionally substituted by one or more" means that a group may be substituted with one or more substituents, preferably 1, 2, 3 or 4, more preferably 1, 2 or 3, and more preferably 1 or 2 substituents, provided that the group has enough positions available susceptible of being substituted, i.e., enough hydrogen atoms available for replacement by a substituent. When more than one substituent are present, they may be the same or different and may be located on any available position.

In the compounds of formula (I), the variable point of attachment depicted for the $R_{10}$ substituents means that, if present, each $R_{10}$ may be attached to any one of the three available positions of the pyrrolidine ring susceptible of being substituted, i.e., having hydrogen atoms available for replacement by a $R_{10}$, as shown with an asterisk (*) in the figure below. Each of the three marked carbon atoms of the pyrrolidine ring has two hydrogens, so each of the marked carbon atoms can have up to two $R_{10}$ substituents, or two $R_{10}$ attached to a common carbon may form an oxo group, or two $R_{10}$ attached to a common carbon atom form a spiro $C_{3-6}$cycloalkyl. If more than one $R_{10}$ is present, unless they form an oxo group or a spiro cycloalkyl, they are preferably not attached to the same carbon atom of the pyrrolidine ring.

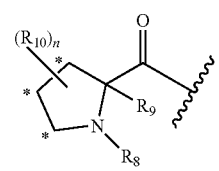

A 5- or 6- membered heteroaryl ring comprising 1 or 2 heteroatoms selected from N, O and S, as used in the present invention, includes, for example, pyridine, pyridazine, pyrimidine, pyrazine, furan, thiophene, pyrrole, imidazole and thiazole rings.

In the definition of formula (I) above, two groups of $R_3$ to $R_7$ attached to adjacent carbon atoms of the phenyl ring may be connected to form a 5- or 6-membered cycloalkyl, wherein 1 or 2 methylene groups of the cycloalkyl may be replaced by O. Said cycloalkyl is, therefore, fused to the phenyl ring in formula (I); examples of said fused cycloalkyl rings include, among others, the following:

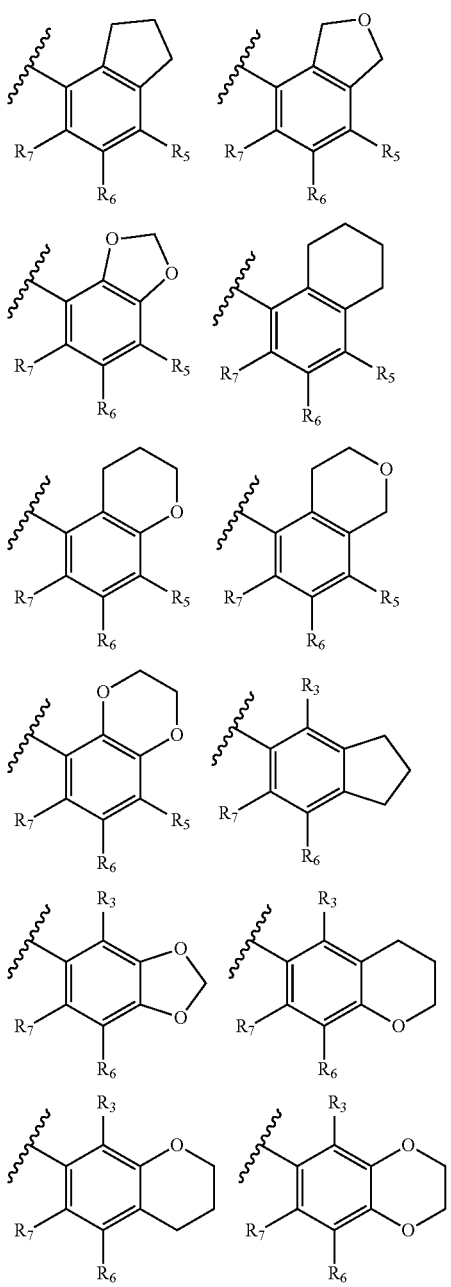

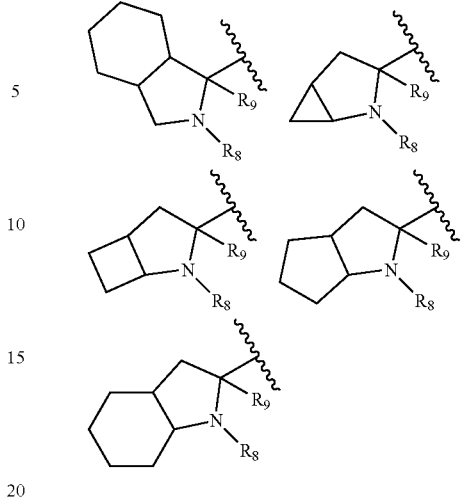

In the definition of formula (I) above two $R_{10}$ attached to adjacent carbon atoms of the pyrrolidine ring may be connected to form a 3- to 6-membered cycloalkyl. Said cycloalkyl is, therefore, fused to the pyrrolidine ring in formula (I); examples of said fused cycloalkyl rings include the following:

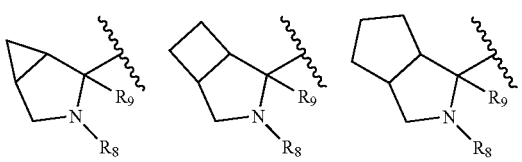

In the definition of formula (I) above $R_{13}$ and $R_{14}$ may form, together with the N atom to which they are attached, a 4- to 6-membered saturated heterocycle, which can optionally contain one additional heteroatom selected from N, S and O, said heterocycle can be optionally substituted with one or more substituents independently selected from $C_{1-4}$alkyl, halo$C_{1-4}$alkyl and $C_{2-5}$acyl, i.e., one or more hydrogen atoms of the ring can be replaced by a $C_{1-4}$alkyl, halo$C_{1-4}$alkyl or $C_{2-5}$acyl, the substitution may be on a C-atom or a N-atom, if present. Examples of such heterocycles include azetidine, pyrrolidine, piperidine, piperazine, morpholine or thiomorpholine, among other.

Similarly, $R_{17}$ and $R_{18}$ may form, together with the N atom to which they are attached, a 4- to 6-membered saturated heterocycle, which can optionally contain one additional heteroatom selected from N, S and O, said heterocycle can be optionally substituted with one or more substituents independently selected from $C_{1-4}$alkyl and halo$C_{1-4}$alkyl, i.e., one or more hydrogen atoms of the ring can be replaced by a $C_{1-4}$alkyl or halo$C_{1-4}$alkyl, the substitution may be on a C-atom or a N-atom, if present. Examples of such heterocycles include azetidine, pyrrolidine, piperidine, piperazine, morpholine or thiomorpholine, among other.

Thorough the description of the current invention, it is understood that when any variable (e.g. $C_{1-6}$alkyl, $C_{1-4}$alkyl, $C_{1-4}$alkoxy, etc.) occurs more than once in a compound of formula (I), its definition on each occurrence is independent of its definition at every each other occurrence, so that the variable may be the same or different on each occasion.

Likewise, when a variable group, such as $R_{10}$, $R_{11}$ or $R_{12}$, occurs more than once in a compound of formula (I), its definition on each occurrence is independent of its definition at every each other occurrence, so that the variable group is independently selected from its possible meanings at each occurrence, and may have the same meaning or different meaning on each occasion. It may be indicated by the expression "each independently selected from".

Similarly, the term "independently selected from" applied to the definition of a group of different variable groups (e.g. $R_3$, $R_4$, $R_5$, $R_6$ and $R_7$), means that the definition of each variable of that group is independently selected from the definition of the other variable of the same group, and may have the same meaning or different meanings.

Compounds of the Invention

Also included within the scope of the invention are the pharmaceutically acceptable salts, solvates, isotopes, stereoisomers and polymorphs of compounds of formula (I). Thus, any reference to a compound of formula (I) throughout the present specification includes a reference to any pharmaceutically acceptable salt, solvate, isotope or polymorph of such compound of formula (I).

The compounds of formula (I) have one or more asymmetric or chiral centres and therefore exist in different stereoisomeric forms. It is intended that all stereoisomeric forms of the compounds of formula (I), including diastereomers, enantiomers, as well as mixtures thereof such as racemic mixtures, form part of the invention.

The compounds of the present invention contain basic nitrogen atoms and may, therefore, form salts with organic or inorganic acids. The term "pharmaceutically acceptable salts" as used herein encompasses any salt with no limitation on the type of salt that can be used, provided that these are acceptable for administration to a patient, meaning that they do not induce undue toxicity, irritation, allergic responses, or the like. Pharmaceutically acceptable salts are well known in the art.

For example, the pharmaceutically acceptable salts suitable for being used in the present invention include those derived from the following acids: hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic and tartaric acids, and the like. Hydrochloric acid is preferred.

The salts of a compound of formula (I) can be obtained, for example, during the final isolation and purification of the compounds of the invention, or can be prepared by treating a compound of formula (I) with a sufficient amount of the desired acid to give the salt in the conventional manner.

The term "solvates" as used herein encompasses a combination of a compound of formula (I) with solvent molecules, bonded by a non-covalent bond. Well known solvent molecules which are able to form solvates include water, alcohols and other polar organic solvents. When the solvate is formed with water, it is also known as a hydrate.

The term "isotopes" as used herein encompasses any isotopically-labelled form of the compounds of formula (I), wherein one or more atoms are replaced by an atom having the same atomic number, but an atomic mass or mass number different from the atomic mass or mass number usually found in nature. Examples of isotopes that can be incorporated into compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulfur, such as $^{35}S$. Those isotopically-labelled compounds are useful, for example, in metabolic or kinetic studies, particularly those labelled with $^2H$, $^3H$, and $^{14}C$. Moreover, substitution with heavier isotopes such as deuterium, $^2H$, may afford certain therapeutic advantages resulting from greater metabolic stability, for example, increased in vivo half-life or reduced dosage requirements.

Isotopically-labelled compounds of the invention can generally be prepared by processes analogous to those described herein, by using an appropriate isotopically-labelled reagent in place of the non-labelled reagent otherwise employed.

The compounds of formula (I) may exist in different physical forms, i.e. amorphous and crystalline forms. Moreover, the compounds of the invention may have the ability to crystallize in more than one form, a characteristic which is known as polymorphism. Polymorphic forms can be distinguished by various physical properties well known in the art such as X-ray diffraction pattern, melting point or solubility. All such physical forms of the compounds of formula (I), including all polymorphic forms ("polymorphs") are included within the scope of the invention.

Furthermore, any formula given herein is also intended to represent the corresponding tautomeric forms. "Tautomer" refers to alternate forms of a molecule that differ in the position of a proton. Examples include, among others, the amide-imidic acid, amine-imine and keto-enol forms.

The first aspect of the invention is further defined by some specific and preferred embodiments as disclosed below.

In one embodiment, the invention relates to a compound of formula (I) or a pharmaceutically acceptable salt or solvate thereof, wherein:

$R_1$ and $R_2$ are independently selected from hydrogen and $C_{1-4}$alkyl;

$R_3$, $R_4$, $R_5$, $R_6$ and $R_7$ are independently selected from hydrogen, —OH, halogen, $C_{1-6}$alkyl, $C_{3-6}$cycloalkyl $C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$, and halo$C_{1-4}$alkoxy, or two of $R_3$ to $R_7$ attached to adjacent carbon atoms are connected to form a 5- or 6-membered cycloalkyl, wherein 1 or 2 methylene groups of the cycloalkyl may be replaced by O, said cycloalkyl can be optionally substituted by one or more $C_{1-4}$alkyl;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, $C_{2-6}$acyl, —$C(O)C_{3-6}$cycloalkyl$C_{0-2}$alkyl, —$CONR_{13}R_{14}$ and —$C(NR_{15})NR_{11}R_{12}$;

$R_9$ is selected from hydrogen and $C_{1-4}$alkyl;

n is 0, 1, 2 or 3;

each $R_{10}$, if present, is independently selected from OH, halogen, $C_{1-6}$alkyl, $C_{1-4}$alkoxy$C_{0-6}$alkyl, —$SR_{11}$ and —$NR_{11}R_{12}$; or two $R_{10}$ attached to a common carbon atom form an oxo; or two $R_{10}$ attached to adjacent carbon atoms are connected to form a 3- to 6-membered cycloalkyl, said cycloalkyl can be optionally substituted by one or more substituents independently selected from $C_{1-4}$alkyl and halogen;

each $R_{11}$ and $R_{12}$ are independently selected from hydrogen and $C_{1-4}$alkyl;

each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N and O, said heterocycle can be optionally substituted by one or more substituents independently selected from $C_{1-4}$alkyl and $C_{2-5}$acyl; and $R_{15}$ is selected from hydrogen, $C_{1-6}$alkyl, halo$C_{1-6}$alkyl, —CN, —$CONR_{11}R_{12}$, —$SO_2$—$R_{11}$, —SO—$R_{11}$ and —$SO_2$—$NR_{11}R_{12}$.

In one embodiment, the invention relates to the compounds of formula (I) wherein the phenyl ring has one, two or three substituents, i.e., at least one of $R_3$ to $R_7$ is not hydrogen and at least two of $R_3$ to $R_7$ are hydrogen.

In another embodiment, the invention relates to the compounds of formula (I) wherein $R_1$ and $R_2$ are independently selected from hydrogen and methyl.

In another embodiment, the invention relates to the compounds of formula (I) wherein $R_1$ and $R_2$ are hydrogen.

In another embodiment, the invention relates to the compounds of formula (I) wherein one of $R_1$ and $R_2$ is hydrogen and the other is $C_{1-4}$alkyl, preferably is methyl.

In another embodiment, the invention relates to the compounds of formula (I) wherein $R_1$ and $R_2$ are $C_{1-4}$alkyl, which are the same or different, preferably $R_1$ and $R_2$ are the same $C_{1-4}$alkyl, and more preferably $R_1$ and $R_2$ are both methyl.

In another embodiment, the invention relates to the compounds of formula (I) wherein $R_3$, $R_4$, $R_5$, $R_6$ and $R_7$ are independently selected from hydrogen, —OH, halogen, $C_{1-6}$alkyl, $C_{3-6}$cycloalkyl$C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy $C_{1-4}$alkoxy, —$CONR_{11}R_{12}$, —$SO_2$—$NR_{11}R_{12}$ and halo $C_{1-4}$alkoxy; preferably are independently selected from hydrogen, —OH, halogen, $C_{1-6}$alkyl, halo$C_{1-6}$alkyl, $C_{1-4}$alkoxy$C_{0-6}$alkyl, $C_{1-4}$alkoxy$C_{1-4}$alkoxy, —$SO_2$—$NR_{11}R_{12}$ and halo$C_{1-4}$alkoxy; more preferably are independently selected from hydrogen, halogen, $C_{1-4}$alkyl, halo$C_{1-4}$alkyl, $C_{1-4}$alkoxy, —$SO_2$—$NR_{11}R_{12}$ and halo $C_{1-4}$alkoxy; and still more preferably $R_3$, $R_4$, $R_5$, $R_6$ and $R_7$ are independently selected from hydrogen, fluoro, chloro, methyl, ethyl, methoxy, ethoxy, trifluoromethyl, trifluoromethoxy and —$SO_2$—$NH_2$.

In a preferred embodiment, the invention relates to the compounds of formula (I) wherein $R_5$ is selected from —OH, halogen, $C_{1-6}$alkyl, $C_{3-6}$cycloalkyl$C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$ and halo$C_{1-4}$alkoxy; preferably is selected from —OH, halogen, $C_{1-6}$alkyl, $C_{1-4}$alkoxy$C_{0-6}$alkyl, $C_{1-4}$alkoxy$C_{1-4}$alkoxy, —$SO_2$—$NR_{11}R_{12}$ and halo$C_{1-4}$alkoxyl; more preferably is selected from halogen, $C_{1-4}$alkyl, halo$C_{1-4}$alkyl, $C_{1-4}$alkoxy, —$SO_2$—$NR_{11}R_{12}$ and halo$C_{1-4}$alkoxy; still more preferably is selected from fluoro, chloro, methyl, ethyl, methoxy, ethoxy, trifluoromethyl, trifluoromethoxy and —$SO_2$—$NH_2$; and still more preferably $R_5$ is fluoro; $R_3$ is selected from hydrogen, halogen and $C_{1-6}$alkyl; more preferably $R_3$ is selected from hydrogen, halogen and $C_{1-4}$alkyl, still more preferably $R_3$ is selected from hydrogen, fluoro, chloro, ethyl and methyl; and still more preferably $R_3$ is hydrogen; and $R_4$, $R_6$ and $R_7$ are hydrogen.

In another preferred embodiment, the invention relates to the compounds of formula (I) wherein $R_4$ and $R_6$ are independently selected from —OH, halogen, $C_{1-6}$alkyl, $C_{3-6}$cycloalkyl$C_{0-4}$alkyl, —$NR_{11}R_{12}$, halo$C_{1-6}$alkyl, hydroxy $C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$ and halo$C_{1-4}$alkoxy; preferably are selected from —OH, halogen, $C_{1-6}$alkyl, $C_{1-4}$alkoxy$C_{0-6}$alkyl and halo$C_{1-4}$alkoxy; more preferably are selected from halogen, $C_{1-4}$alkyl, $C_{1-4}$alkoxy and halo$C_{1-4}$alkoxy; and still more preferably are selected from fluoro, chloro, methyl, ethyl, methoxy, ethoxy, trifluoromethyl and trifluoromethoxy; and $R_3$, $R_5$ and $R_7$ are hydrogen.

In another preferred embodiment two of $R_3$ to $R_7$ attached to adjacent carbon atoms are connected to form a 5- or 6-membered cycloalkyl, wherein 1 or 2 methylene groups of the cycloalkyl may be replaced by O, said cycloalkyl can be optionally substituted by one or more $C_{1-4}$alkyl; and preferably the other three of $R_3$ to $R_7$ are hydrogen; more preferably $R_4$ and $R_5$ are connected to form a 5- or 6-membered cycloalkyl, wherein 1 or 2 methylene groups of the cycloalkyl may be replaced by 0, said cycloalkyl can be optionally substituted by one or more $C_{1-4}$alkyl, and $R_3$, $R_6$ and $R_7$ are hydrogen; more preferably $R_4$ and $R_5$ are connected to form a saturated 6-membered cycloalkyl, wherein 1 or 2 methylene groups of the cycloalkyl may be replaced by O atoms, said cycloalkyl can be optionally substituted by one or more $C_{1-4}$alkyl, and $R_3$, $R_6$ and $R_7$ are hydrogen; and still more preferably $R_4$ and $R_5$ are connected to form a 1,4-dioxane, and $R_3$, $R_6$ and $R_7$ are hydrogen.

In another embodiment, the invention relates to the compounds of formula (I) wherein $R_8$ is selected from selected from —OH, $C_{1-6}$alkyl, $C_{3-6}$cycloalkyl$C_{0-4}$alkyl, $C_{2-5}$acyl, —$CONR_{13}R_{14}$ and —$C(NR_{15})NR_{11}R_{12}$; wherein each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}$alkyl and $C_{2-5}$acyl; more preferably $R_8$ is selected from —OH, $C_{1-4}$alkyl, $C_{3-6}$cycloalkyl$C_{1-4}$alkyl, $C_{2-5}$acyl, —$CONR_{13}R_{14}$ and —$C(NR_{15})NR_{11}R_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}$alkyl and $C_{2-3}$acyl;

In another embodiment, the invention relates to the compounds of formula (I) wherein $R_9$ is $C_{1-4}$alkyl, preferably is methyl.

In another embodiment, the invention relates to the compounds of formula (I) wherein $R_9$ is hydrogen.

In another embodiment, the invention relates to the compounds of formula (I) wherein n is 1, 2 or 3, preferably is 1 or 2, and each $R_{10}$ is independently selected from halogen, $C_{1-4}$alkyl and —$NR_{11}R_{12}$; or two $R_{10}$ attached to a common carbon atom form an oxo; or two $R_{10}$ attached to adjacent carbon atoms are connected to form a 3- to 6-membered cycloalkyl, more preferably a 3- to 5-membered cycloalkyl, and still more preferably a 3-membered cycloalkyl, said cycloalkyl can be optionally substituted by one or more substituents independently selected from $C_{1-4}$alkyl and halogen; more preferably, each $R_{10}$ is independently selected from chloro, fluoro, methyl, ethyl, and —$NH_2$, or two $R_{10}$ attached to a common carbon atom form an oxo; or two $R_{10}$ attached to adjacent carbon atoms are connected to form a 3-membered cycloalkyl.

In another embodiment, the invention relates to the compounds of formula (I) wherein n is 0.

In a preferred embodiment, the invention relates to the compounds of formula (I) wherein:

$R_1$ and $R_2$ are independently selected from hydrogen and $C_{1-4}$alkyl; preferably from hydrogen and methyl, and more preferably $R_1$ and $R_2$ are hydrogen;

$R_3$, $R_4$, $R_5$, $R_6$ and $R_7$ are independently selected from hydrogen, —OH, halogen, $C_{1-6}$alkyl, $C_{3-6}$cycloalkyl$C_{0-4}$alkyl, —$NR_{11}R_{12}$, halo$C_{1-6}$alkyl, hydroxy $C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$ and halo$C_{1-4}$alkoxy; preferably are independently selected from hydrogen, —OH, halogen, $C_{1-6}$alkyl, halo$C_{1-6}$alkyl, $C_{1-4}$alkoxy$C_{0-6}$alkyl, $C_{1-4}$alkoxy$C_{1-4}$alkoxy, —$SO_2$—$NR_{11}R_{12}$ and halo$C_{1-4}$alkoxy; more preferably are independently selected from hydrogen, halogen, $C_{1-4}$alkyl, halo$C_{1-4}$alkyl, $C_{1-4}$alkoxy, —$SO_2$—

$NR_{11}R_{12}$ and $haloC_{1-4}alkoxy$; and still more preferably $R_3$, $R_4$, $R_5$, $R_6$ and $R_7$ are independently selected from hydrogen, fluoro, chloro, methyl, ethyl, methoxy, ethoxy, trifluoromethyl, trifluoromethoxy and —SO$_2$—NH$_2$;

$R_8$ is selected from —OH, $C_{1-6}alkyl$, $haloC_{1-6}alkyl$, $hydroxyC_{1-4}alkyl$, $C_{1-4}alkoxyC_{0-4}alkyl$, $C_{3-6}cycloalkylC_{0-4}alkyl$, $C_{2-5}acyl$, —C(O)C$_{3-6}$cycloalkylC$_{0-2}$alkyl, —CONR$_{13}$R$_{14}$ and —C(NR$_{15}$)NR$_{11}$R$_{12}$; preferably selected from —OH, $C_{1-6}alkyl$, $C_{3-6}cycloalkyl$ $C_{0-4}alkyl$, $C_{2-5}acyl$, —CONR$_{13}$R$_{14}$ and —C(NR$_{15}$)NR$_{11}$R$_{12}$, wherein each $R_{13}$ and $R_{14}$ are independently selected from hydrogen and $C_{1-4}alkyl$, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}alkyl$ and $C_{2-5}acyl$; more preferably $R_8$ is selected from —OH, $C_{1-4}alkyl$, $C_{3-6}cycloalkylC_{1-4}alkyl$, $C_{2-5}acyl$, —CONR$_{13}$R$_{14}$ and —C(NR$_{15}$)NR$_{11}$R$_{12}$; wherein each $R_{13}$ and $R_{14}$ are independently selected from hydrogen and $C_{1-4}alkyl$, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}alkyl$ and $C_{2-3}acyl$;

$R_9$ is selected from hydrogen and $C_{1-4}alky$, preferably is selected from methyl and hydrogen, more preferably is hydrogen; and n is 1, 2 or 3, preferably is 1 or 2, and each $R_{10}$ is independently selected from —OH, halogen, $C_{1-6}alkyl$, $C_{1-4}alkoxyC_{0-6}alkyl$, —SR$_{11}$ and NR$_{11}$R$_{12}$; or two $R_{10}$ attached to a common carbon atom form an oxo; or two $R_{10}$ attached to adjacent carbon atoms are connected to form a 3- to 6-membered cycloalkyl, more preferably a 3- to 5-membered cycloalkyl, and still more preferably a 3-membered cycloalkyl, said cycloalkyl can be optionally substituted by one or more substituents independently selected from $C_{1-4}alkyl$ and halogen; more preferably, each $R_{10}$ is independently selected from halogen, $C_{1-4}alkyl$ and —NR$_{11}$R$_{12}$, or two $R_{10}$ attached to a common carbon atom form an oxo; or two $R_{10}$ attached to adjacent carbon atoms are connected to form a a 3- to 5-membered cycloalkyl, preferably a 3-membered cycloalkyl, said cycloalkyl can be optionally substituted by one or more substituents independently selected from $C_{1-4}alkyl$ and halogen; and still more preferably, each $R_{10}$ is independently selected from chloro, fluoro, methyl, ethyl, and —NH$_2$, or two $R_{10}$ attached to a common carbon atom form an oxo; or two $R_{10}$ attached to adjacent carbon atoms are connected to form a 3-membered cycloalkyl;

and wherein:

preferably at least one of $R_3$ to $R_7$ is not hydrogen and at least two of $R_3$ to $R_7$ are hydrogen;

each $R_{11}$ and $R_{12}$ are independently selected from hydrogen and $C_{1-4}alkyl$, and preferably are selected from hydrogen and methyl; and $R_{15}$ is selected from hydrogen, $C_{1-6}alkyl$, $haloC_{1-6}alkyl$, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and $C_{1-4}alkyl$; and more preferably $R_{15}$ is selected from hydrogen and $C_{1-4}alkyl$;

or a pharmaceutically acceptable salt or solvate thereof.

In another preferred embodiment, the invention relates to the compounds of formula (I) wherein:

$R_1$ and $R_2$ are independently selected from hydrogen and $C_{1-4}alkyl$; preferably from hydrogen and methyl, and more preferably $R_1$ and $R_2$ are hydrogen;

$R_5$ is selected from —OH, halogen, $C_{1-6}alkyl$, $C_{3-6}cycloalkylC_{0-4}alkyl$, —NR$_{11}$R$_{12}$, $haloC_{1-6}alkyl$, $hydroxyC_{1-6}alkyl$, $C_{1-4}alkoxyC_{0-6}alkyl$, $C_{1-4}alkoxy$ $C_{1-4}alkoxy$, —CONR$_{11}$R$_{12}$, —SO$_2$—NR$_{11}$R$_{12}$ and $haloC_{1-4}alkoxy$; preferably is selected from —OH, halogen, $C_{1-6}alkyl$, $haloC_{1-6}alkyl$, $C_{1-4}alkoxyC_{0-6}alkyl$, $C_{1-4}alkoxyC_{1-4}alkoxy$, —SO$_2$—NR$_{11}$R$_{12}$ and $haloC_{1-4}alkoxyl$; more preferably is selected from halogen, $C_{1-4}alkyl$, $haloC_{1-4}alkyl$, $C_{1-4}alkoxy$, —SO$_2$—NR$_{11}$R$_{12}$ and $haloC_{1-4}alkoxy$; still more preferably is selected from fluoro, chloro, methyl, ethyl, methoxy, ethoxy, trifluoromethyl, trifluoromethoxy and —SO$_2$—NH$_2$; and still more preferably $R_5$ is fluoro;

$R_3$ is selected from hydrogen, halogen and $C_{1-6}alkyl$; more preferably $R_3$ is selected from hydrogen, halogen and $C_{1-4}alkyl$, still more preferably $R_3$ is selected from hydrogen, fluoro, chloro, ethyl and methyl; and still more preferably $R_3$ is hydrogen;

$R_4$, $R_6$ and $R_7$ are hydrogen;

$R_8$ is selected from —OH, $C_{1-6}alkyl$, $haloC_{1-6}alkyl$, $hydroxyC_{1-4}alkyl$, $C_{1-4}alkoxyC_{0-4}alkyl$, $C_{3-6}cycloalkylC_{0-4}alkyl$, $C_{2-5}acyl$, —C(O)C$_{3-6}$cycloalkylC$_{0-2}$alkyl, —CONR$_{13}$R$_{14}$ and —C(NR$_{15}$)NR$_{11}$R$_{12}$; preferably selected from —OH, $C_{1-6}alkyl$, $C_{3-6}cycloalkyl$ $C_{0-4}alkyl$, $C_{2-5}acyl$, —CONR$_{13}$R$_{14}$ and —C(NR$_{15}$)NR$_{11}$R$_{12}$, wherein each $R_{13}$ and $R_{14}$ are independently selected from hydrogen and $C_{1-4}alkyl$, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}alkyl$ and $C_{2-5}acyl$; more preferably $R_8$ is selected from —OH, $C_{1-4}alkyl$, $C_{3-6}cycloalkylC_{1-4}alkyl$, $C_{2-5}acyl$, —CONR$_{13}$R$_{14}$ and —C(NR$_{15}$)NR$_{11}$R$_{12}$; wherein each $R_{13}$ and $R_{14}$ are independently selected from hydrogen and $C_{1-4}alkyl$, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}alkyl$ and $C_{2-3}acyl$;

$R_9$ is selected from hydrogen and $C_{1-4}alky$, preferably is selected from methyl and hydrogen, more preferably is hydrogen; and n is 1, 2 or 3, preferably is 1 or 2, and each $R_{10}$ is independently selected from —OH, halogen, $C_{1-6}alkyl$, $C_{1-4}alkoxyC_{0-6}alkyl$, —SR$_{11}$ and —NR$_{11}$R$_{12}$; or two $R_{10}$ attached to a common carbon atom form an oxo; or two $R_{10}$ attached to adjacent carbon atoms are connected to form a 3- to 6-membered cycloalkyl, more preferably a 3- to 5-membered cycloalkyl, and still more preferably a 3-membered cycloalkyl, said cycloalkyl can be optionally substituted by one or more substituents independently selected from $C_{1-4}alkyl$ and halogen; more preferably, each $R_{10}$ is independently selected from halogen, $C_{1-4}$alkyl and —$NR_{11}R_{12}$, or two $R_{10}$ attached to a common carbon atom form an oxo; or two $R_{10}$ attached to adjacent carbon atoms are connected to form a a 3- to 5-membered cycloalkyl, preferably a 3-membered cycloalkyl, said cycloalkyl can be optionally substituted by one or more substituents independently selected from $C_{1-4}$alkyl and halogen; and still more preferably, each $R_{10}$ is independently selected from chloro, fluoro, methyl, ethyl, and —$NH_2$, or two $R_{10}$ attached to a common carbon atom form an oxo; or two $R_{10}$ attached to adjacent carbon atoms are connected to form a 3-membered cycloalkyl;

and wherein:

each $R_{11}$ and $R_{12}$ are independently selected from hydrogen and $C_{1-4}$alkyl, and preferably are selected from hydrogen and methyl; and $R_{15}$ is selected from hydrogen, $C_{1-6}$alkyl, halo$C_{1-6}$alkyl, —CN, —$CONR_{11}R_{12}$, —$SO_2$—$R_{11}$, —SO—$R_{11}$ and —$SO_2$—$NR_{11}R_{12}$; preferably is selected from hydrogen, —CN and $C_{1-4}$alkyl; and more preferably $R_{15}$ is selected from hydrogen and $C_{1-4}$alkyl;

or a pharmaceutically acceptable salt or solvate thereof.

In another preferred embodiment, the invention relates to the compounds of formula (I) wherein:

$R_1$ and $R_2$ are independently selected from hydrogen and $C_{1-4}$alkyl; preferably from hydrogen and methyl, and more preferably $R_1$ and $R_2$ are hydrogen;

$R_4$ and $R_6$ are independently selected from —OH, halogen, $C_{1-6}$alkyl, $C_{3-6}$cycloalkyl$C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$ and halo$C_{1-4}$alkoxy; preferably are selected from —OH, halogen, $C_{1-6}$alkyl, halo$C_{1-6}$alkyl, $C_{1-4}$alkoxy$C_{0-6}$alkyl and halo$C_{1-4}$alkoxy; more preferably are selected from halogen, $C_{1-4}$alkyl, halo$C_{1-4}$alkyl, $C_{1-4}$alkoxy and halo$C_{1-4}$alkoxy; and still more preferably are selected from fluoro, chloro, methyl, ethyl, methoxy, ethoxy, trifluoromethyl and trifluoromethoxy;

$R_3$, $R_6$ and $R_7$ are hydrogen;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, $C_{2-5}$acyl, —C(O)$C_{3-6}$cycloalkyl$C_{0-2}$alkyl, —$CONR_{13}R_{14}$ and —C($NR_{15}$)$NR_{11}R_{12}$; preferably selected from —OH, $C_{1-6}$alkyl, $C_{3-6}$cycloalkyl$C_{0-4}$alkyl, $C_{2-5}$acyl, —$CONR_{13}R_{14}$ and —C($NR_{15}$)$NR_{11}R_{12}$, wherein each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}$alkyl and $C_{2-5}$acyl; more preferably $R_8$ is selected from —OH, $C_{1-4}$alkyl, $C_{3-6}$cycloalkyl$C_{1-4}$alkyl, $C_{2-5}$acyl, —$CONR_{13}R_{14}$ and —C($NR_{15}$)$NR_{11}R_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}$alkyl and $C_{2-3}$acyl;

$R_9$ is selected from hydrogen and $C_{1-4}$alky, preferably is selected from methyl and hydrogen, more preferably is hydrogen; and n is 1, 2 or 3, preferably is 1 or 2, and each $R_{10}$ is independently selected from —OH, halogen, $C_{1-6}$alkyl, $C_{1-4}$alkoxy$C_{0-6}$alkyl, —$SR_{11}$ and —$NR_{11}R_{12}$; or two $R_{10}$ attached to a common carbon atom form an oxo; or two $R_{10}$ attached to adjacent carbon atoms are connected to form a 3- to 6-membered cycloalkyl, more preferably a 3- to 5-membered cycloalkyl, and still more preferably a 3-membered cycloalkyl, said cycloalkyl can be optionally substituted by one or more substituents independently selected from $C_{1-4}$alkyl and halogen; more preferably, each $R_{10}$ is independently selected from halogen, $C_{1-4}$alkyl and —$NR_{11}R_{12}$, or two $R_{10}$ attached to a common carbon atom form an oxo; or two $R_{10}$ attached to adjacent carbon atoms are connected to form a a 3- to 5-membered cycloalkyl, preferably a 3-membered cycloalkyl, said cycloalkyl can be optionally substituted by one or more substituents independently selected from $C_{1-4}$alkyl and halogen; and still more preferably, each $R_{10}$ is independently selected from chloro, fluoro, methyl, ethyl, and —$NH_2$, or two $R_{10}$ attached to a common carbon atom form an oxo; or two $R_{10}$ attached to adjacent carbon atoms are connected to form a 3-membered cycloalkyl;

and wherein:

each $R_{11}$ and $R_{12}$ are independently selected from hydrogen and $C_{1-4}$alkyl, or preferably are selected from hydrogen and methyl; and $R_{15}$ is selected from hydrogen, $C_{1-6}$alkyl, halo$C_{1-6}$alkyl, —CN, —$CONR_{11}R_{12}$, —$SO_2$—$R_{11}$, —SO—$R_{11}$ and —$SO_2$—$NR_{11}R_{12}$; preferably is selected from hydrogen, —CN and $C_{1-4}$alkyl; and more preferably $R_{15}$ is selected from hydrogen and $C_{1-4}$alkyl;

or a pharmaceutically acceptable salt or solvate thereof.

In another preferred embodiment, the invention relates to the compounds of formula (I) wherein:

$R_1$ and $R_2$ are independently selected from hydrogen and $C_{1-4}$alkyl; preferably from hydrogen and methyl, and more preferably $R_1$ and $R_2$ are hydrogen;

two of $R_3$ to $R_7$ attached to adjacent carbon atoms are connected to form a 5- or 6-membered cycloalkyl, wherein 1 or 2 methylene groups of the cycloalkyl may be replaced by O, said cycloalkyl can be optionally substituted by one or more $C_{1-4}$alkyl; and preferably the other three of $R_3$ to $R_7$ are hydrogen; more preferably, $R_4$ and $R_5$ are connected to form a 5- or 6-membered cycloalkyl, wherein 1 or 2 methylene groups of the cycloalkyl may be replaced by O, said cycloalkyl can be optionally substituted by one or more $C_{1-4}$alkyl, and preferably $R_3$, $R_6$ and $R_7$ are hydrogen; still more preferably $R_4$ and $R_5$ are connected to form a saturated 6-membered cycloalkyl, wherein 1 or 2 methylene groups of the cycloalkyl may be replaced by O atoms, said cycloalkyl can be optionally substituted by one or more $C_{1-4}$alkyl, and $R_3$, $R_6$ and $R_7$ are hydrogen; and still more preferably $R_4$ and $R_5$ are connected to form a 1,4-dioxane, and $R_3$, $R_6$ and $R_7$ are hydrogen;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, $C_{2-5}$acyl, —C(O)$C_{3-6}$cycloalkyl$C_{0-2}$alkyl, —$CONR_{13}R_{14}$ and C($NR_{15}$)$NR_{11}R_{12}$; preferably selected from —OH, $C_{1-6}$alkyl, $C_{3-6}$cycloalkyl$C_{0-4}$alkyl, $C_{2-5}$acyl, —$CONR_{13}R_{14}$ and —C($NR_{15}$)$NR_{11}R_{12}$, wherein each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}$alkyl and $C_{2-5}$acyl; more preferably $R_8$ is selected from —OH, $C_{1-4}$alkyl, $C_{3-6}$cycloalkyl$C_{1-4}$alkyl, $C_{2-5}$acyl, —CONR$_{13}$R$_{14}$ and —C(NR$_{15}$)NR$_{11}$R$_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}$alkyl and $C_{2-3}$acyl;

$R_9$ is selected from hydrogen and $C_{1-4}$alky, preferably is selected from methyl and hydrogen, more preferably is hydrogen; and n is 1, 2 or 3, preferably is 1 or 2, and each $R_{10}$ is independently selected from —OH, halogen, $C_{1-6}$alkyl, $C_{1-4}$alkoxy$C_{0-6}$alkyl, —SR$_{11}$ and —NR$_{11}$R$_{12}$; or two $R_{10}$ attached to a common carbon atom form an oxo; or two $R_{10}$ attached to adjacent carbon atoms are connected to form a 3- to 6-membered cycloalkyl, more preferably a 3- to 5-membered cycloalkyl, and still more preferably a 3-membered cycloalkyl, said cycloalkyl can be optionally substituted by one or more substituents independently selected from $C_{1-4}$alkyl and halogen; more preferably, each $R_{10}$ is independently selected from halogen, $C_{1-4}$alkyl and —NR$_{11}$R$_{12}$, or two $R_{10}$ attached to a common carbon atom form an oxo; or two $R_{10}$ attached to adjacent carbon atoms are connected to form a a 3- to 5-membered cycloalkyl, preferably a 3-membered cycloalkyl, said cycloalkyl can be optionally substituted by one or more substituents independently selected from $C_{1-4}$alkyl and halogen; and still more preferably, each $R_{10}$ is independently selected from chloro, fluoro, methyl, ethyl, and —NH$_2$, or two $R_{10}$ attached to a common carbon atom form an oxo; or two $R_{10}$ attached to adjacent carbon atoms are connected to form a 3-membered cycloalkyl;

and wherein:

each $R_{11}$ and $R_{12}$ are independently selected from hydrogen and $C_{1-4}$alkyl, or preferably are selected from hydrogen and methyl; and $R_{15}$ is selected from hydrogen, $C_{1-6}$alkyl, halo$C_{1-6}$alkyl, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and $C_{1-4}$alkyl; and more preferably $R_{15}$ is selected from hydrogen and $C_{1-4}$alkyl; or a pharmaceutically acceptable salt or solvate thereof.

In a preferred embodiment, the invention relates to the compounds of formula (I) wherein:

$R_1$ and $R_2$ are independently selected from hydrogen and $C_{1-4}$alkyl; preferably from hydrogen and methyl, and more preferably $R_1$ and $R_2$ are hydrogen;

$R_3$, $R_4$, $R_5$, $R_6$ and $R_7$ are independently selected from hydrogen, —OH, halogen, $C_{1-6}$alkyl, $C_{3-6}$cycloalkyl$C_{0-4}$alkyl, —NR$_{11}$R$_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —CONR$_{11}$R$_{12}$, —SO$_2$—NR$_{11}$R$_{12}$ and halo$C_{1-4}$alkoxy; preferably are independently selected from hydrogen, —OH, halogen, $C_{1-6}$alkyl, halo$C_{1-6}$alkyl, $C_{1-4}$alkoxy$C_{0-6}$alkyl, $C_{1-4}$alkoxy$C_{1-4}$alkoxy, —SO$_2$—NR$_{11}$R$_{12}$ and halo$C_{1-4}$alkoxy; more preferably are independently selected from hydrogen, halogen, $C_{1-4}$alkyl, halo$C_{1-4}$alkyl, $C_{1-4}$alkoxy, —SO$_2$—NR$_{11}$R$_{12}$ and halo$C_{1-4}$alkoxy; and still more preferably $R_3$, $R_4$, $R_5$, $R_6$ and $R_7$ are independently selected from hydrogen, fluoro, chloro, methyl, ethyl, methoxy, ethoxy, trifluoromethyl, trifluoromethoxy and —SO$_2$—NH$_2$;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, $C_{2-5}$acyl, —C(O)$C_{3-6}$cycloalkyl$C_{0-2}$alkyl, —CONR$_{13}$R$_{14}$ and —C(NR$_{15}$)NR$_{11}$R$_{12}$; preferably selected from —OH, $C_{1-6}$alkyl, $C_{3-6}$cycloalkyl$C_{0-4}$alkyl, $C_{2-5}$acyl, —CONR$_{13}$R$_{14}$ and —C(NR$_{15}$)NR$_{11}$R$_{12}$, wherein each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from $C_{1-4}$alkyl and $C_{2-5}$acyl; more preferably $R_8$ is selected from —OH, $C_{1-4}$alkyl, $C_{3-6}$cycloalkyl$C_{1-4}$alkyl, $C_{2-5}$acyl, —CONR$_{13}$R$_{14}$ and —C(NR$_{15}$)NR$_{11}$R$_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from $C_{1-4}$alkyl and $C_{2-3}$acyl;

$R_9$ is selected from hydrogen and $C_{1-4}$alky, preferably is selected from methyl and hydrogen, more preferably is hydrogen; and n is 0;

and wherein:

preferably at least one of $R_3$ to $R_7$ is not hydrogen and at least two of $R_3$ to $R_7$ are hydrogen;

each $R_{11}$ and $R_{12}$ are independently selected from hydrogen and $C_{1-4}$alkyl, and preferably are selected from hydrogen and methyl; and $R_{15}$ is selected from hydrogen, $C_{1-6}$alkyl, halo$C_{1-6}$alkyl, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and $C_{1-4}$alkyl; and more preferably $R_{15}$ is selected from hydrogen and $C_{1-4}$alkyl;

or a pharmaceutically acceptable salt or solvate thereof.

In another preferred embodiment, the invention relates to the compounds of formula (I) wherein:

$R_1$ and $R_2$ are independently selected from hydrogen and $C_{1-4}$alkyl; preferably from hydrogen and methyl, and more preferably $R_1$ and $R_2$ are hydrogen;

$R_5$ is selected from —OH, halogen, $C_{1-6}$alkyl, $C_{3-6}$cycloalkyl$C_{0-4}$alkyl, —NR$_{11}$R$_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —CONR$_{11}$R$_{12}$, —SO$_2$—NR$_{11}$R$_{12}$ and halo$C_{1-4}$alkoxy; preferably is selected from —OH, halogen, $C_{1-6}$alkyl, halo$C_{1-6}$alkyl, $C_{1-4}$alkoxy$C_{0-6}$alkyl, $C_{1-4}$alkoxy$C_{1-4}$alkoxy, —SO$_2$—NR$_{11}$R$_{12}$ and halo$C_{1-4}$alkoxyl; more preferably is selected from halogen, $C_{1-4}$alkyl, halo$C_{1-4}$alkyl, $C_{1-4}$alkoxy, —SO$_2$—NR$_{11}$R$_{12}$ and halo$C_{1-4}$alkoxy; still more preferably is selected from fluoro, chloro, methyl, ethyl, methoxy, ethoxy, trifluoromethyl, trifluoromethoxy and —SO$_2$—NH$_2$; and still more preferably R$_5$ is fluoro;

R$_3$ is selected from hydrogen, halogen and C$_{1-6}$alkyl; more preferably R$_3$ is selected from hydrogen, halogen and C$_{1-4}$alkyl, still more preferably R$_3$ is selected from hydrogen, fluoro, chloro, ethyl and methyl; and still more preferably R$_3$ is hydrogen;

R$_4$, R$_6$ and R$_7$ are hydrogen;

R$_8$ is selected from —OH, C$_{1-6}$alkyl, haloC$_{1-6}$alkyl, hydroxyC$_{1-4}$alkyl, C$_{1-4}$alkoxyC$_{0-4}$alkyl, C$_{3-6}$cycloalkylC$_{0-4}$alkyl, C$_{2-5}$acyl, —C(O)C$_{3-6}$cycloalkylC$_{0-2}$alkyl, —CONR$_{13}$R$_{14}$ and —C(NR$_{15}$)NR$_{11}$R$_{12}$; preferably selected from —OH, C$_{1-6}$alkyl, C$_{3-6}$cycloalkylC$_{0-4}$alkyl, C$_{2-5}$acyl, —CONR$_{13}$R$_{14}$ and —C(NR$_{15}$)NR$_{11}$R$_{12}$; wherein each R$_{13}$ and R$_{14}$ are independently selected from hydrogen and C$_{1-4}$alkyl, or R$_{13}$ and R$_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from C$_{1-4}$alkyl and C$_{2-5}$acyl; more preferably R$_8$ is selected from —OH, C$_{1-4}$alkyl, C$_{3-6}$cycloalkylC$_{1-4}$alkyl, C$_{2-5}$acyl, —CONR$_{13}$R$_{14}$ and —C(NR$_{15}$)NR$_{11}$R$_{12}$; wherein each R$_{13}$ and R$_{14}$ are independently selected from hydrogen and C$_{1-4}$alkyl, or R$_{13}$ and R$_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from C$_{1-4}$alkyl and C$_{2-3}$acyl;

R$_9$ is selected from hydrogen and C$_{1-4}$alky, preferably is selected from methyl and hydrogen, more preferably is hydrogen; and n is 0;

and wherein:

each R$_{11}$ and R$_{12}$ are independently selected from hydrogen and C$_{1-4}$alkyl, and preferably are selected from hydrogen and methyl; and R$_{15}$ is selected from hydrogen, C$_{1-6}$alkyl, haloC$_{1-6}$alkyl, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and C$_{1-4}$alkyl; and more preferably R$_{15}$ is selected from hydrogen and C$_{1-4}$alkyl; or a pharmaceutically acceptable salt or solvate thereof.

In another preferred embodiment, the invention relates to the compounds of formula (I) wherein:

R$_1$ and R$_2$ are independently selected from hydrogen and C$_{1-4}$alkyl; preferably from hydrogen and methyl, and more preferably R$_1$ and R$_2$ are hydrogen;

R$_4$ and R$_6$ are independently selected from —OH, halogen, C$_{1-6}$alkyl, C$_{3-6}$cycloalkylC$_{0-4}$alkyl, —NR$_{11}$R$_{12}$, haloC$_{1-6}$alkyl, hydroxyC$_{1-6}$alkyl, C$_{1-4}$alkoxyC$_{0-6}$alkyl, C$_{1-4}$alkoxyC$_{1-4}$alkoxy, —CONR$_{11}$R$_{12}$, —SO$_2$—NR$_{11}$R$_{12}$ and haloC$_{1-4}$alkoxy; preferably are selected from —OH, halogen, C$_{1-6}$alkyl, haloC$_{1-6}$alkyl, C$_{1-4}$alkoxyC$_{0-6}$alkyl and haloC$_{1-4}$alkoxy; preferably are selected from halogen, C$_{1-4}$alkyl, haloC$_{1-4}$alkyl, C$_{1-4}$alkoxy and haloC$_{1-4}$alkoxy; more preferably are selected from fluoro, chloro, methyl, ethyl, methoxy, ethoxy, trifluoromethyl and trifluoromethoxy;

R$_3$, R$_6$ and R$_7$ are hydrogen;

R$_8$ is selected from —OH, C$_{1-6}$alkyl, haloC$_{1-6}$alkyl, hydroxyC$_{1-4}$alkyl, C$_{1-4}$alkoxyC$_{0-4}$alkyl, C$_{3-6}$cycloalkylC$_{0-4}$alkyl, C$_{2-5}$acyl, —C(O)C$_{3-6}$cycloalkylC$_{0-2}$alkyl, —CONR$_{13}$R$_{14}$ and —C(NR$_{15}$)NR$_{11}$R$_{12}$; preferably selected from —OH, C$_{1-6}$alkyl, C$_{3-6}$cycloalkyl C$_{0-4}$alkyl, C$_{2-5}$acyl, —CONR$_{13}$R$_{14}$ and —C(NR$_{15}$)NR$_{11}$R$_{12}$, wherein each R$_{13}$ and R$_{14}$ are independently selected from hydrogen and C$_{1-4}$alkyl, or R$_{13}$ and R$_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from C$_{1-4}$alkyl and C$_{2-5}$acyl; more preferably R$_8$ is selected from —OH, C$_{1-4}$alkyl, C$_{3-6}$cycloalkylC$_{1-4}$alkyl, C$_{2-5}$acyl, —CONR$_{13}$R$_{14}$ and —C(NR$_{15}$)NR$_{11}$R$_{12}$; wherein each R$_{13}$ and R$_{14}$ are independently selected from hydrogen and C$_{1-4}$alkyl, or R$_{13}$ and R$_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from C$_{1-4}$alkyl and C$_{2-3}$acyl;

R$_9$ is selected from hydrogen and C$_{1-4}$alky, preferably is selected from methyl and hydrogen, more preferably is hydrogen; and n is 0;

and wherein:

each R$_{11}$ and R$_{12}$ are independently selected from hydrogen and C$_{1-4}$alkyl, and preferably are selected from hydrogen and methyl; and R$_{15}$ is selected from hydrogen, C$_{1-6}$alkyl, haloC$_{1-6}$alkyl, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and C$_{1-4}$alkyl; and more preferably R$_{15}$ is selected from hydrogen and C$_{1-4}$alkyl;

or a pharmaceutically acceptable salt or solvate thereof.

In another preferred embodiment, the invention relates to the compounds of formula (I) wherein:

R$_1$ and R$_2$ are independently selected from hydrogen and C$_{1-4}$alkyl; preferably from hydrogen and methyl, and more preferably R$_1$ and R$_2$ are hydrogen;

two of R$_3$ to R$_7$ attached to adjacent carbon atoms are connected to form a 5- or 6-membered cycloalkyl, wherein 1 or 2 methylene groups of the cycloalkyl may be replaced by O, said cycloalkyl can be optionally substituted by one or more C$_{1-4}$alkyl; and preferably the other three of R$_3$ to R$_7$ are hydrogen; more preferably, R$_4$ and R$_5$ are connected to form a 5- or 6-membered cycloalkyl, wherein 1 or 2 methylene groups of the cycloalkyl may be replaced by O, said cycloalkyl can be optionally substituted by one or more C$_{1-4}$alkyl, and preferably R$_3$, R$_6$ and R$_7$ are hydrogen; still more preferably R$_4$ and R$_5$ are connected to form a saturated 6-membered cycloalkyl, wherein 1 or 2 methylene groups of the cycloalkyl may be replaced by O atoms, said cycloalkyl can be optionally substituted by one or more C$_{1-4}$alkyl, and R$_3$, R$_6$ and R$_7$ are hydrogen; and still more preferably R$_4$ and R$_5$ are connected to form a 1,4-dioxane, and R$_3$, R$_6$ and R$_7$ are hydrogen;

R$_8$ is selected from —OH, C$_{1-6}$alkyl, haloC$_{1-6}$alkyl, hydroxyC$_{1-4}$alkyl, C$_{1-4}$alkoxyC$_{0-4}$alkyl, C$_{3-6}$cycloalkylC$_{0-4}$alkyl, C$_{2-5}$acyl, —C(O)C$_{3-6}$cycloalkylC$_{0-2}$alkyl, —CONR$_{13}$R$_{14}$ and —C(NR$_{15}$)NR$_{11}$R$_{12}$; preferably selected from —OH, C$_{1-6}$alkyl, C$_{3-6}$cycloalkyl C$_{0-4}$alkyl, C$_{2-5}$acyl, —CONR$_{13}$R$_{14}$ and —C(NR$_{15}$)

NR$_{11}$R$_{12}$, wherein each R$_{13}$ and R$_{14}$ are independently selected from hydrogen and C$_{1-4}$alkyl, or R$_{13}$ and R$_{14}$ form, together with the N atom to which they are attached, a 4- to 6-membered saturated heterocycle, which can optionally contain one additional heteroatom selected from N, S and O, preferably selected from N and O, said heterocycle can be optionally substituted by one or more substituents independently selected from C$_{1-4}$alkyl and C$_{2-5}$acyl; more preferably R$_8$ is selected from —OH, C$_{1-4}$alkyl, C$_{3-6}$cycloalkylC$_{1-4}$alkyl, C$_{2-5}$acyl, —CONR$_{13}$R$_{14}$ and —C(NR$_{15}$)NR$_{11}$R$_{12}$; wherein each R$_{13}$ and R$_{14}$ are independently selected from hydrogen and C$_{1-4}$alkyl, or R$_{13}$ and R$_{14}$ form, together with the N atom to which they are attached, a 6-membered saturated heterocycle, which contains one additional heteroatom selected from N and O, preferably said heterocycle is piperazinyl or morpholinyl, said heterocycle can be optionally substituted by one or more substituents independently selected from C$_{1-4}$alkyl and C$_{2-3}$acyl;

R$_9$ is selected from hydrogen and C$_{1-4}$alky, preferably is selected from methyl and hydrogen, more preferably is hydrogen; and n is 0;

and wherein:

each R$_{11}$ and R$_{12}$ are independently selected from hydrogen and C$_{1-4}$alkyl, and preferably are selected from hydrogen and methyl; and R$_{15}$ is selected from hydrogen, C$_{1-6}$alkyl, haloC$_{1-6}$alkyl, —CN, —CONR$_{11}$R$_{12}$, —SO$_2$—R$_{11}$, —SO—R$_{11}$ and —SO$_2$—NR$_{11}$R$_{12}$; preferably is selected from hydrogen, —CN and C$_{1-4}$alkyl; and more preferably R$_{15}$ is selected from hydrogen and C$_{1-4}$alkyl;

or a pharmaceutically acceptable salt or solvate thereof.

In another preferred embodiment, compound of formula (I) is selected from the following list of compounds:

N'-(4-fluorophenyl)-1,5-dimethypyrrolidine-2-carbohydrazide (R)-2-(2-(4-fluorophenyl)hydrazinecarbonyl)pyrrolidine-1-carboxamide (S)-2-(2-(4-fluorophenyl)hydrazinecarbonyl)pyrrolidine-1-carboxamide 2-(2-(4-fluorophenyl)hydrazinecarbonyl)pyrrolidine-1-carboxamide 2-(2-(4-fluoro-2-methylphenyl)hydrazine-1-carbonyl)pyrrolidine-1-carboxamide 2-(2-(3,5-difluorophenyl)hydrazinecarbonyl)pyrrolidine-1-carboxamide 2-(2-(4-(trifluoromethoxy)phenyl)hydrazinecarbonyl)pyrrolidine-1-carboxamide 2-(2-(4-(trifluoromethyl)phenyl)hydrazinecarbonyl)pyrrolidine-1-carboxamide 2-(2-(4-chloro-2-fluorophenyl)hydrazinecarbonyl)pyrrolidine-1-carboxamide 2-(2-(4-methoxyphenyl)hydrazinecarbonyl)pyrrolidine-1-carboxamide 2-(2-(2,3-dihydrobenzo[b][1,4]dioxin-6-yl)hydrazinecarbonyl)pyrrolidine-1-carboxamide 2-(2-(4-sulfamoylphenyl)hydrazinecarbonyl)pyrrolidine-1-carboxamide (2S,4S)-4-fluoro-2-(2-(4-fluorophenyl)hydrazinecarbonyl)pyrrolidine-1-carboxamide (R)-1-acetyl-N'-(4-fluorophenyl)pyrrolidine-2-carbohydrazide N'-(4-fluorophenyl)-1-hydroxypyrrolidine-2-carbohydrazide N'-(4-fluorophenyl)-1,2-dimethylpyrrolidine-2-carbohydrazide 2-(2-(4-fluorophenyl)hydrazinecarbonyl)-N,N-dimethylpyrrolidine-1-carboxamide N'-(4-fluorophenyl)-1-(piperazine-1-carbonyl)pyrrolidine-2-carbohydrazide 1-(4-acetylpiperazine-1-carbonyl)-N'-(4-fluorophenyl)pyrrolidine-2-carbohydrazide N'-(4-fluorophenyl)-1-(morpholine-4-carbonyl)pyrrolidine-2-carbohydrazide N'-(4-fluorophenyl)-1-methyl-5-oxopyrrolidine-2-carbohydrazide N'-(4-fluorophenyl)-1-methylpyrrolidine-2-carbohydrazide 4-amino-N'-(4-fluorophenyl)-1-methylpyrrolidine-2-carbohydrazide 4-fluoro-N'-(4-fluorophenyl)-1-methylpyrrolidine-2-carbohydrazide (S)-1-(cyclopropylmethyl)-N'-(4-fluorophenyl)pyrrolidine-2-carbohydrazide N'-(4-fluorophenyl)-3-methyl-3-azabicyclo[3.1.0]hexane-2-carbohydrazide N'-(4-fluorophenyl)-1,4-dimethylpyrrolidine-2-carbohydrazide N'-(4-fluorophenyl)-1,3-dimethylpyrrolidine-2-carbohydrazide 1-ethyl-N'-(4-fluorophenyl)pyrrolidine-2-carbohydrazide 2-(2-(4-fluorophenyl)hydrazinecarbonyl)pyrrolidine-1-carboximidamide 2-(2-phenylhydrazine-1-carbonyl)pyrrolidine-1-carboxamide 2-(1-methyl-2-phenylhydrazine-1-carbonyl)pyrrolidine-1-carboxamide 2-(2-methyl-2-phenylhydrazine-1-carbonyl)pyrrolidine-1-carboxamide 2-(2-(4-fluorophenyl)hydrazine-1-carbonyl)pyrrolidine-1-carboxamide 2-(2-(3-fluorophenyl)hydrazine-1-carbonyl)pyrrolidine-1-carboxamide 2-(2-(2-fluorophenyl)hydrazine-1-carbonyl)pyrrolidine-1-carboxamide 2-(2-(4-chlorophenyl)hydrazine-1-carbonyl)pyrrolidine-1-carboxamide 2-(2-(3-chlorophenyl)hydrazine-1-carbonyl)pyrrolidine-1-carboxamide 2-(2-(2-chlorophenyl)hydrazine-1-carbonyl)pyrrolidine-1-carboxamide 2-(2-(4-methoxyphenyl)hydrazine-1-carbonyl)pyrrolidine-1-carboxamide 2-(2-(3-methoxyphenyl)hydrazine-1-carbonyl)pyrrolidine-1-carboxamide 2-(2-(2-methoxyphenyl)hydrazine-1-carbonyl)pyrrolidine-1-carboxamide 2-(2-(p-tolyl)hydrazine-1-carbonyl)pyrrolidine-1-carboxamide 2-(2-(m-tolyl)hydrazine-1-carbonyl)pyrrolidine-1-carboxamide 2-(2-(o-tolyl)hydrazine-1-carbonyl)pyrrolidine-1-carboxamide 2-(2-(4-(trifluoromethyl)phenyl)hydrazine-1-carbonyl)pyrrolidine-1-carboxamide 2-(2-(3-(trifluoromethyl)phenyl)hydrazine-1-carbonyl)pyrrolidine-1-carboxamide 2-(2-(2-(trifluoromethyl)phenyl)hydrazine-1-carbonyl)pyrrolidine-1-carboxamide ethyl 4-(2-(carbamoylprolyl)hydrazinyl)benzoate ethyl 3-(2-(carbamoylprolyl)hydrazinyl)benzoate ethyl 2-(2-(carbamoylprolyl)hydrazinyl)benzoate
2-(2-(4-cyanophenyl)hydrazine-1-carbonyl)pyrrolidine-1-carboxamide
2-(2-(3-cyanophenyl)hydrazine-1-carbonyl)pyrrolidine-1-carboxamide
2-(2-(2-cyanophenyl)hydrazine-1-carbonyl)pyrrolidine-1-carboxamide
4-(2-(carbamoylprolyl)hydrazinyl)benzoic acid
3-(2-(carbamoylprolyl)hydrazinyl)benzoic acid
2-(2-(carbamoylprolyl)hydrazinyl)benzoic acid
N-methyl-2-(2-phenylhydrazine-1-carbonyl)pyrrolidine-1-carboxamide
N-methyl-2-(1-methyl-2-phenylhydrazine-1-carbonyl)pyrrolidine-1-carboxamide
N-methyl-2-(2-methyl-2-phenylhydrazine-1-carbonyl)pyrrolidine-1-carboxamide
2-(2-(4-fluorophenyl)hydrazine-1-carbonyl)-N-methylpyrrolidine-1-carboxamide
2-(2-(3-fluorophenyl)hydrazine-1-carbonyl)-N-methylpyrrolidine-1-carboxamide
2-(2-(2-fluorophenyl)hydrazine-1-carbonyl)-N-methylpyrrolidine-1-carboxamide
2-(2-(4-chlorophenyl)hydrazine-1-carbonyl)-N-methylpyrrolidine-1-carboxamide
2-(2-(3-chlorophenyl)hydrazine-1-carbonyl)-N-methylpyrrolidine-1-carboxamide
2-(2-(2-chlorophenyl)hydrazine-1-carbonyl)-N-methylpyrrolidine-1-carboxamide
2-(2-(4-methoxyphenyl)hydrazine-1-carbonyl)-N-methylpyrrolidine-1-carboxamide
2-(2-(3-methoxyphenyl)hydrazine-1-carbonyl)-N-methylpyrrolidine-1-carboxamide
2-(2-(2-methoxyphenyl)hydrazine-1-carbonyl)-N-methylpyrrolidine-1-carboxamide
N-methyl-2-(2-(p-tolyl)hydrazine-1-carbonyl)pyrrolidine-1-carboxamide
N-methyl-2-(2-(m-tolyl)hydrazine-1-carbonyl)pyrrolidine-1-carboxamide
N-methyl-2-(2-(o-tolyl)hydrazine-1-carbonyl)pyrrolidine-1-carboxamide
N-methyl-2-(2-(4-(trifluoromethyl)phenyl)hydrazine-1-carbonyl)pyrrolidine-1-carboxamide
N-methyl-2-(2-(3-(trifluoromethyl)phenyl)hydrazine-1-carbonyl)pyrrolidine-1-carboxamide
N-methyl-2-(2-(2-(trifluoromethyl)phenyl)hydrazine-1-carbonyl)pyrrolidine-1-carboxamide
ethyl 4-(2-((methylcarbamoyl)prolyl)hydrazinyl)benzoate
ethyl 3-(2-((methylcarbamoyl)prolyl)hydrazinyl)benzoate
ethyl 2-(2-((methylcarbamoyl)prolyl)hydrazinyl)benzoate
2-(2-(4-cyanophenyl)hydrazine-1-carbonyl)-N-methylpyrrolidine-1-carboxamide
2-(2-(3-cyanophenyl)hydrazine-1-carbonyl)-N-methylpyrrolidine-1-carboxamide
2-(2-(2-cyanophenyl)hydrazine-1-carbonyl)-N-methylpyrrolidine-1-carboxamide
4-(2-((methylcarbamoyl)prolyl)hydrazinyl)benzoic acid
3-(2-((methylcarbamoyl)prolyl)hydrazinyl)benzoic acid
2-(2-((methylcarbamoyl)prolyl)hydrazinyl)benzoic acid
N-cyclopropyl-2-(2-phenylhydrazine-1-carbonyl)pyrrolidine-1-carboxamide
N-cyclopropyl-2-(1-methyl-2-phenylhydrazine-1-carbonyl)pyrrolidine-1-carboxamide
N-cyclopropyl-2-(2-methyl-2-phenylhydrazine-1-carbonyl)pyrrolidine-1-carboxamide
N-cyclopropyl-2-(2-(4-fluorophenyl)hydrazine-1-carbonyl)pyrrolidine-1-carboxamide
N-cyclopropyl-2-(2-(3-fluorophenyl)hydrazine-1-carbonyl)pyrrolidine-1-carboxamide
N-cyclopropyl-2-(2-(2-fluorophenyl)hydrazine-1-carbonyl)pyrrolidine-1-carboxamide
2-(2-(4-chlorophenyl)hydrazine-1-carbonyl)-N-cyclopropylpyrrolidine-1-carboxamide
2-(2-(3-chlorophenyl)hydrazine-1-carbonyl)-N-cyclopropylpyrrolidine-1-carboxamide
2-(2-(2-chlorophenyl)hydrazine-1-carbonyl)-N-cyclopropylpyrrolidine-1-carboxamide
N-cyclopropyl-2-(2-(4-methoxyphenyl)hydrazine-1-carbonyl)pyrrolidine-1-carboxamide
N-cyclopropyl-2-(2-(3-methoxyphenyl)hydrazine-1-carbonyl)pyrrolidine-1-carboxamide
N-cyclopropyl-2-(2-(2-methoxyphenyl)hydrazine-1-carbonyl)pyrrolidine-1-carboxamide
N-cyclopropyl-2-(2-(p-tolyl)hydrazine-1-carbonyl)pyrrolidine-1-carboxamide
N-cyclopropyl-2-(2-(m-tolyl)hydrazine-1-carbonyl)pyrrolidine-1-carboxamide
N-cyclopropyl-2-(2-(o-tolyl)hydrazine-1-carbonyl)pyrrolidine-1-carboxamide
N-cyclopropyl-2-(2-(4-(trifluoromethyl)phenyl)hydrazine-1-carbonyl)pyrrolidine-1-carboxamide
N-cyclopropyl-2-(2-(3-(trifluoromethyl)phenyl)hydrazine-1-carbonyl)pyrrolidine-1-carboxamide
N-cyclopropyl-2-(2-(2-(trifluoromethyl)phenyl)hydrazine-1-carbonyl)pyrrolidine-1-carboxamide
ethyl 4-(2-((cyclopropylcarbamoyl)prolyl)hydrazinyl)benzoate
ethyl 3-(2-((cyclopropylcarbamoyl)prolyl)hydrazinyl)benzoate
ethyl 2-(2-((cyclopropylcarbamoyl)prolyl)hydrazinyl)benzoate
2-(2-(4-cyanophenyl)hydrazine-1-carbonyl)-N-cyclopropylpyrrolidine-1-carboxamide
2-(2-(3-cyanophenyl)hydrazine-1-carbonyl)-N-cyclopropylpyrrolidine-1-carboxamide
2-(2-(2-cyanophenyl)hydrazine-1-carbonyl)-N-cyclopropylpyrrolidine-1-carboxamide
4-(2-((cyclopropylcarbamoyl)prolyl)hydrazinyl)benzoic acid
3-(2-((cyclopropylcarbamoyl)prolyl)hydrazinyl)benzoic acid
2-(2-((cyclopropylcarbamoyl)prolyl)hydrazinyl)benzoic acid
ethyl (2-(2-phenylhydrazine-1-carbonyl)pyrrolidine-1-carbonyl)alaninate
ethyl (2-(1-methyl-2-phenylhydrazine-1-carbonyl)pyrrolidine-1-carbonyl)alaninate
ethyl (2-(2-methyl-2-phenylhydrazine-1-carbonyl)pyrrolidine-1-carbonyl)alaninate
ethyl (2-(2-(4-fluorophenyl)hydrazine-1-carbonyl)pyrrolidine-1-carbonyl)alaninate
ethyl (2-(2-(3-fluorophenyl)hydrazine-1-carbonyl)pyrrolidine-1-carbonyl)alaninate
ethyl (2-(2-(2-fluorophenyl)hydrazine-1-carbonyl)pyrrolidine-1-carbonyl)alaninate
ethyl (2-(2-(4-chlorophenyl)hydrazine-1-carbonyl)pyrrolidine-1-carbonyl)alaninate
ethyl (2-(2-(3-chlorophenyl)hydrazine-1-carbonyl)pyrrolidine-1-carbonyl)alaninate
ethyl (2-(2-(2-chlorophenyl)hydrazine-1-carbonyl)pyrrolidine-1-carbonyl)alaninate ethyl (2-(2-(4-methoxyphenyl)hydrazine-1-carbonyl)pyrrolidine-1-carbonyl)alaninate
ethyl (2-(2-(3-methoxyphenyl)hydrazine-1-carbonyl)pyrrolidine-1-carbonyl)alaninate
ethyl (2-(2-(2-methoxyphenyl)hydrazine-1-carbonyl)pyrrolidine-1-carbonyl)alaninate
ethyl (2-(2-(p-tolyl)hydrazine-1-carbonyl)pyrrolidine-1-carbonyl)alaninate
ethyl (2-(2-(m-tolyl)hydrazine-1-carbonyl)pyrrolidine-1-carbonyl)alaninate
ethyl (2-(2-(o-tolyl)hydrazine-1-carbonyl)pyrrolidine-1-carbonyl)alaninate
ethyl (2-(2-(4-(trifluoromethyl)phenyl)hydrazine-1-carbonyl)pyrrolidine-1-carbonyl)alaninate
ethyl (2-(2-(3-(trifluoromethyl)phenyl)hydrazine-1-carbonyl)pyrrolidine-1-carbonyl)alaninate
ethyl (2-(2-(2-(trifluoromethyl)phenyl)hydrazine-1-carbonyl)pyrrolidine-1-carbonyl)alaninate
ethyl 4-(2-(((1-ethoxy-1-oxopropan-2-yl)carbamoyl)prolyl)hydrazinyl)benzoate
ethyl 3-(2-(((1-ethoxy-1-oxopropan-2-yl)carbamoyl)prolyl)hydrazinyl)benzoate
ethyl 2-(2-(((1-ethoxy-1-oxopropan-2-yl)carbamoyl)prolyl)hydrazinyl)benzoate
ethyl (2-(2-(4-cyanophenyl)hydrazine-1-carbonyl)pyrrolidine-1-carbonyl)alaninate
ethyl (2-(2-(3-cyanophenyl)hydrazine-1-carbonyl)pyrrolidine-1-carbonyl)alaninate
ethyl (2-(2-(2-cyanophenyl)hydrazine-1-carbonyl)pyrrolidine-1-carbonyl)alaninate
4-(2-(((1-ethoxy-1-oxopropan-2-yl)carbamoyl)prolyl)hydrazinyl)benzoic acid
3-(2-(((1-ethoxy-1-oxopropan-2-yl)carbamoyl)prolyl)hydrazinyl)benzoic acid
2-(2-(((1-ethoxy-1-oxopropan-2-yl)carbamoyl)prolyl)hydrazinyl)benzoic acid
methyl 2-(2-phenylhydrazine-1-carbonyl)pyrrolidine-1-carboxylate
methyl 2-(1-methyl-2-phenylhydrazine-1-carbonyl)pyrrolidine-1-carboxylate
methyl 2-(2-methyl-2-phenylhydrazine-1-carbonyl)pyrrolidine-1-carboxylate
methyl 2-(2-(4-fluorophenyl)hydrazine-1-carbonyl)pyrrolidine-1-carboxylate
methyl 2-(2-(3-fluorophenyl)hydrazine-1-carbonyl)pyrrolidine-1-carboxylate
methyl 2-(2-(2-fluorophenyl)hydrazine-1-carbonyl)pyrrolidine-1-carboxylate
methyl 2-(2-(4-chlorophenyl)hydrazine-1-carbonyl)pyrrolidine-1-carboxylate
methyl 2-(2-(3-chlorophenyl)hydrazine-1-carbonyl)pyrrolidine-1-carboxylate
methyl 2-(2-(2-chlorophenyl)hydrazine-1-carbonyl)pyrrolidine-1-carboxylate
methyl 2-(2-(4-methoxyphenyl)hydrazine-1-carbonyl)pyrrolidine-1-carboxylate
methyl 2-(2-(3-methoxyphenyl)hydrazine-1-carbonyl)pyrrolidine-1-carboxylate
methyl 2-(2-(2-methoxyphenyl)hydrazine-1-carbonyl)pyrrolidine-1-carboxylate
methyl 2-(2-(p-tolyl)hydrazine-1-carbonyl)pyrrolidine-1-carboxylate
methyl 2-(2-(m-tolyl)hydrazine-1-carbonyl)pyrrolidine-1-carboxylate
methyl 2-(2-(o-tolyl)hydrazine-1-carbonyl)pyrrolidine-1-carboxylate
methyl 2-(2-(4-(trifluoromethyl)phenyl)hydrazine-1-carbonyl)pyrrolidine-1-carboxylate
methyl 2-(2-(3-(trifluoromethyl)phenyl)hydrazine-1-carbonyl)pyrrolidine-1-carboxylate
methyl 2-(2-(2-(trifluoromethyl)phenyl)hydrazine-1-carbonyl)pyrrolidine-1-carboxylate
methyl 2-(2-(4-(ethoxycarbonyl)phenyl)hydrazine-1-carbonyl)pyrrolidine-1-carboxylate
methyl 2-(2-(3-(ethoxycarbonyl)phenyl)hydrazine-1-carbonyl)pyrrolidine-1-carboxylate
methyl 2-(2-(2-(ethoxycarbonyl)phenyl)hydrazine-1-carbonyl)pyrrolidine-1-carboxylate
methyl 2-(2-(4-cyanophenyl)hydrazine-1-carbonyl)pyrrolidine-1-carboxylate
methyl 2-(2-(3-cyanophenyl)hydrazine-1-carbonyl)pyrrolidine-1-carboxylate
methyl 2-(2-(2-cyanophenyl)hydrazine-1-carbonyl)pyrrolidine-1-carboxylate
4-(2-((methoxycarbonyl)prolyl)hydrazinyl)benzoic acid
3-(2-((methoxycarbonyl)prolyl)hydrazinyl)benzoic acid
2-(2-((methoxycarbonyl)prolyl)hydrazinyl)benzoic acid
2-(2-(4-fluorophenyl)hydrazine-1-carbonyl)pyrrolidine-1-carboxamide
2-(2-(4-fluorophenyl)hydrazine-1-carbonyl)-N-methylpyrrolidine-1-carboxamide
N-ethyl-2-(2-(4-fluorophenyl)hydrazine-1-carbonyl)pyrrolidine-1-carboxamide
2-(2-(4-fluorophenyl)hydrazine-1-carbonyl)-N-isopropylpyrrolidine-1-carboxamide
2-(2-(4-fluorophenyl)hydrazine-1-carbonyl)-N-(2-hydroxyethyl)pyrrolidine-1-carboxamide
2-(2-(4-fluorophenyl)hydrazine-1-carbonyl)-N-(2-methoxyethyl)pyrrolidine-1-carboxamide
N-(2-aminoethyl)-2-(2-(4-fluorophenyl)hydrazine-1-carbonyl)pyrrolidine-1-carboxamide
N-(2-(dimethylamino)ethyl)-2-(2-(4-fluorophenyl)hydrazine-1-carbonyl)pyrrolidine-1-carboxamide
2-(2-(4-fluorophenyl)hydrazine-1-carbonyl)-N-(2-(piperazin-1-yl)ethyl)pyrrolidine-1-carboxamide
2-(2-(4-fluorophenyl)hydrazine-1-carbonyl)-N-(2-(4-methylpiperazin-1-yl)ethyl)pyrrolidine-1-carboxamide
2-(2-(4-fluorophenyl)hydrazine-1-carbonyl)-N-(2-morpholinoethyl)pyrrolidine-1-carboxamide
N-cyclopropyl-2-(2-(4-fluorophenyl)hydrazine-1-carbonyl)pyrrolidine-1-carboxamide
N-cyclobutyl-2-(2-(4-fluorophenyl)hydrazine-1-carbonyl)pyrrolidine-1-carboxamide
N-cyclopentyl-2-(2-(4-fluorophenyl)hydrazine-1-carbonyl)pyrrolidine-1-carboxamide
2-(2-(4-fluorophenyl)hydrazine-1-carbonyl)-N-(tetrahydro-2H-pyran-4-yl)pyrrolidine-1-carboxamide
2-(2-(4-fluorophenyl)hydrazine-1-carbonyl)-N,N-dimethylpyrrolidine-1-carboxamide
N'-(4-fluorophenyl)-1-(piperazine-1-carbonyl)pyrrolidine-2-carbohydrazide
N'-(4-fluorophenyl)-1-(4-methylpiperazine-1-carbonyl)pyrrolidine-2-carbohydrazide
N'-(4-fluorophenyl)-1-(morpholine-4-carbonyl)pyrrolidine-2-carbohydrazide
N-(2-amino-2-oxoethyl)-2-(2-(4-fluorophenyl)hydrazine-1-carbonyl)pyrrolidine-1-carboxamide
N-(1-amino-1-oxopropan-2-yl)-2-(2-(4-fluorophenyl)hydrazine-1-carbonyl)pyrrolidine-1-carboxamide
N-(1-amino-3-hydroxy-1-oxobutan-2-yl)-2-(2-(4-fluorophenyl)hydrazine-1-carbonyl)pyrrolidine-1-carboxamide N-(1-amino-3-methoxy-1-oxobutan-2-yl)-2-(2-(4-fluorophenyl)hydrazine-1-carbonyl)pyrrolidine-1-carboxamide
4-amino-3-(2-(2-(4-fluorophenyl)hydrazine-1-carbonyl)pyrrolidine-1-carboxamido)-4-oxobutan-2-yl acetate
N-(1-amino-3-hydroxy-1-oxopropan-2-yl)-2-(2-(4-fluorophenyl)hydrazine-1-carbonyl)pyrrolidine-1-carboxamide
methyl 2-(2-(4-fluorophenyl)hydrazine-1-carbonyl)pyrrolidine-1-carboxylate
ethyl 2-(2-(4-fluorophenyl)hydrazine-1-carbonyl)pyrrolidine-1-carboxylate
isopropyl 2-(2-(4-fluorophenyl)hydrazine-1-carbonyl)pyrrolidine-1-carboxylate
cyclopentyl 2-(2-(4-fluorophenyl)hydrazine-1-carbonyl)pyrrolidine-1-carboxylate
2-(2-(4-methoxyphenyl)hydrazine-1-carbonyl)pyrrolidine-1-carboxamide
2-(2-(4-methoxyphenyl)hydrazine-1-carbonyl)-N-methylpyrrolidine-1-carboxamide
N-ethyl-2-(2-(4-methoxyphenyl)hydrazine-1-carbonyl)pyrrolidine-1-carboxamide
N-isopropyl-2-(2-(4-methoxyphenyl)hydrazine-1-carbonyl)pyrrolidine-1-carboxamide
N-(2-hydroxyethyl)-2-(2-(4-methoxyphenyl)hydrazine-1-carbonyl)pyrrolidine-1-carboxamide
N-(2-methoxyethyl)-2-(2-(4-methoxyphenyl)hydrazine-1-carbonyl)pyrrolidine-1-carboxamide
N-(2-aminoethyl)-2-(2-(4-methoxyphenyl)hydrazine-1-carbonyl)pyrrolidine-1-carboxamide
N-(2-(dimethylamino)ethyl)-2-(2-(4-methoxyphenyl)hydrazine-1-carbonyl)pyrrolidine-1-carboxamide
2-(2-(4-methoxyphenyl)hydrazine-1-carbonyl)-N-(2-(piperazin-1-yl)ethyl)pyrrolidine-1-carboxamide
2-(2-(4-methoxyphenyl)hydrazine-1-carbonyl)-N-(2-(4-methylpiperazin-1-yl)ethyl)pyrrolidine-1-carboxamide
2-(2-(4-methoxyphenyl)hydrazine-1-carbonyl)-N-(2-morpholinoethyl)pyrrolidine-1-carboxamide
N-cyclopropyl-2-(2-(4-methoxyphenyl)hydrazine-1-carbonyl)pyrrolidine-1-carboxamide
N-cyclobutyl-2-(2-(4-methoxyphenyl)hydrazine-1-carbonyl)pyrrolidine-1-carboxamide
N-cyclopentyl-2-(2-(4-methoxyphenyl)hydrazine-1-carbonyl)pyrrolidine-1-carboxamide
2-(2-(4-methoxyphenyl)hydrazine-1-carbonyl)-N-(tetrahydro-2H-pyran-4-yl)pyrrolidine-1-carboxamide
2-(2-(4-methoxyphenyl)hydrazine-1-carbonyl)-N,N-dimethylpyrrolidine-1-carboxamide
N'-(4-methoxyphenyl)-1-(piperazine-1-carbonyl)pyrrolidine-2-carbohydrazide
N'-(4-methoxyphenyl)-1-(4-methylpiperazine-1-carbonyl)pyrrolidine-2-carbohydrazide
N'-(4-methoxyphenyl)-1-(morpholine-4-carbonyl)pyrrolidine-2-carbohydrazide
N-(2-amino-2-oxoethyl)-2-(2-(4-methoxyphenyl)hydrazine-1-carbonyl)pyrrolidine-1-carboxamide
N-(1-amino-1-oxopropan-2-yl)-2-(2-(4-methoxyphenyl)hydrazine-1-carbonyl)pyrrolidine-1-carboxamide
N-(1-amino-3-hydroxy-1-oxobutan-2-yl)-2-(2-(4-methoxyphenyl)hydrazine-1-carbonyl)pyrrolidine-1-carboxamide
N-(1-amino-3-methoxy-1-oxobutan-2-yl)-2-(2-(4-methoxyphenyl)hydrazine-1-carbonyl)pyrrolidine-1-carboxamide
4-amino-3-(2-(2-(4-methoxyphenyl)hydrazine-1-carbonyl)pyrrolidine-1-carboxamido)-4-oxobutan-2-yl acetate
N-(1-amino-3-hydroxy-1-oxopropan-2-yl)-2-(2-(4-methoxyphenyl)hydrazine-1-carbonyl)pyrrolidine-1-carboxamide
methyl 2-(2-(4-methoxyphenyl)hydrazine-1-carbonyl)pyrrolidine-1-carboxylate
ethyl 2-(2-(4-methoxyphenyl)hydrazine-1-carbonyl)pyrrolidine-1-carboxylate
isopropyl 2-(2-(4-methoxyphenyl)hydrazine-1-carbonyl)pyrrolidine-1-carboxylate
cyclopentyl 2-(2-(4-methoxyphenyl)hydrazine-1-carbonyl)pyrrolidine-1-carboxylate
2-(2-(4-fluorophenyl)hydrazine-1-carbonyl)pyrrolidine-1-carboxamide
5-(2-(4-fluorophenyl)hydrazine-1-carbonyl)-2,2-dimethylpyrrolidine-1-carboxamide
2-(2-(4-fluorophenyl)hydrazine-1-carbonyl)-4-methylpyrrolidine-1-carboxamide
2-(2-(4-fluorophenyl)hydrazine-1-carbonyl)-4-isopropylpyrrolidine-1-carboxamide
6-(2-(4-fluorophenyl)hydrazine-1-carbonyl)-5-azaspiro[2.4]heptane-5-carboxamide
2-(2-(4-fluorophenyl)hydrazine-1-carbonyl)-4-hydroxypyrrolidine-1-carboxamide
2-(2-(4-fluorophenyl)hydrazine-1-carbonyl)-4-methoxypyrrolidine-1-carboxamide
1-carbamoyl-5-(2-(4-fluorophenyl)hydrazine-1-carbonyl)pyrrolidin-3-yl acetate
2-(2-(4-fluorophenyl)hydrazine-1-carbonyl)-4-fluoropyrrolidine-1-carboxamide
4,4-difluoro-2-(2-(4-fluorophenyl)hydrazine-1-carbonyl)pyrrolidine-1-carboxamide
2-(2-(4-fluorophenyl)hydrazine-1-carbonyl)-4-(trifluoromethyl)pyrrolidine-1-carboxamide
4-cyano-2-(2-(4-fluorophenyl)hydrazine-1-carbonyl)pyrrolidine-1-carboxamide
2-(2-(4-fluorophenyl)hydrazine-1-carbonyl)-3-phenylpyrrolidine-1-carboxamide
2-(2-(4-fluorophenyl)hydrazine-1-carbonyl)-3-hydroxypyrrolidine-1-carboxamide
2-(2-(4-fluorophenyl)hydrazine-1-carbonyl)-3-methoxypyrrolidine-1-carboxamide
1-carbamoyl-2-(2-(4-fluorophenyl)hydrazine-1-carbonyl)pyrrolidin-3-yl acetate
2-(2-(4-fluorophenyl)hydrazine-1-carbonyl)-3-azabicyclo[3.1.0]hexane-3-carboxamide
2-(2-(4-methoxyphenyl)hydrazine-1-carbonyl)pyrrolidine-1-carboxamide
5-(2-(4-methoxyphenyl)hydrazine-1-carbonyl)-2,2-dimethylpyrrolidine-1-carboxamide
2-(2-(4-methoxyphenyl)hydrazine-1-carbonyl)-4-methylpyrrolidine-1-carboxamide
4-isopropyl-2-(2-(4-methoxyphenyl)hydrazine-1-carbonyl)pyrrolidine-1-carboxamide
6-(2-(4-methoxyphenyl)hydrazine-1-carbonyl)-5-azaspiro[2.4]heptane-5-carboxamide
4-hydroxy-2-(2-(4-methoxyphenyl)hydrazine-1-carbonyl)pyrrolidine-1-carboxamide
4-methoxy-2-(2-(4-methoxyphenyl)hydrazine-1-carbonyl)pyrrolidine-1-carboxamide
1-carbamoyl-5-(2-(4-methoxyphenyl)hydrazine-1-carbonyl)pyrrolidin-3-yl acetate
4-fluoro-2-(2-(4-methoxyphenyl)hydrazine-1-carbonyl)pyrrolidine-1-carboxamide
4,4-difluoro-2-(2-(4-methoxyphenyl)hydrazine-1-carbonyl)pyrrolidine-1-carboxamide
2-(2-(4-methoxyphenyl)hydrazine-1-carbonyl)-4-(trifluoromethyl)pyrrolidine-1-carboxamide 4-cyano-2-(2-(4-methoxyphenyl)hydrazine-1-carbonyl)pyrrolidine-1-carboxamide 2-(2-(4-methoxyphenyl)hydrazine-1-carbonyl)-3-phenylpyrrolidine-1-carboxamide 3-hydroxy-2-(2-(4-methoxyphenyl)hydrazine-1-carbonyl)pyrrolidine-1-carboxamide 3-methoxy-2-(2-(4-methoxyphenyl)hydrazine-1-carbonyl)pyrrolidine-1-carboxamide 1-carbamoyl-2-(2-(4-methoxyphenyl)hydrazine-1-carbonyl)pyrrolidin-3-yl acetate 2-(2-(4-methoxyphenyl)hydrazine-1-carbonyl)-3-azabicyclo[3.1.0]hexane-3-carboxamide N-cyclopropyl-2-(2-(4-fluorophenyl)hydrazine-1-carbonyl)pyrrolidine-1-carboxamide N-cyclopropyl-5-(2-(4-fluorophenyl)hydrazine-1-carbonyl)-2,2-dimethylpyrrolidine-1-carboxamide N-cyclopropyl-2-(2-(4-fluorophenyl)hydrazine-1-carbonyl)-4-methylpyrrolidine-1-carboxamide N-cyclopropyl-2-(2-(4-fluorophenyl)hydrazine-1-carbonyl)-4-isopropylpyrrolidine-1-carboxamide N-cyclopropyl-6-(2-(4-fluorophenyl)hydrazine-1-carbonyl)-5-azaspiro[2.4]heptane-5-carboxamide N-cyclopropyl-2-(2-(4-fluorophenyl)hydrazine-1-carbonyl)-4-hydroxypyrrolidine-1-carboxamide N-cyclopropyl-2-(2-(4-fluorophenyl)hydrazine-1-carbonyl)-4-methoxypyrrolidine-1-carboxamide 1-(cyclopropylcarbamoyl)-5-(2-(4-fluorophenyl)hydrazine-1-carbonyl)pyrrolidin-3-yl acetate N-cyclopropyl-4-fluoro-2-(2-(4-fluorophenyl)hydrazine-1-carbonyl)pyrrolidine-1-carboxamide N-cyclopropyl-4,4-difluoro-2-(2-(4-fluorophenyl)hydrazine-1-carbonyl)pyrrolidine-1-carboxamide N-cyclopropyl-2-(2-(4-fluorophenyl)hydrazine-1-carbonyl)-4-(trifluoromethyl)pyrrolidine-1-carboxamide 4-cyano-N-cyclopropyl-2-(2-(4-fluorophenyl)hydrazine-1-carbonyl)pyrrolidine-1-carboxamide N-cyclopropyl-2-(2-(4-fluorophenyl)hydrazine-1-carbonyl)-3-phenylpyrrolidine-1-carboxamide N-cyclopropyl-2-(2-(4-fluorophenyl)hydrazine-1-carbonyl)-3-hydroxypyrrolidine-1-carboxamide N-cyclopropyl-2-(2-(4-fluorophenyl)hydrazine-1-carbonyl)-3-methoxypyrrolidine-1-carboxamide 1-(cyclopropylcarbamoyl)-2-(2-(4-fluorophenyl)hydrazine-1-carbonyl)pyrrolidin-3-yl acetate N-cyclopropyl-2-(2-(4-fluorophenyl)hydrazine-1-carbonyl)-3-azabicyclo[3.1.0]hexane-3-carboxamide N-cyclopropyl-2-(2-(4-methoxyphenyl)hydrazine-1-carbonyl)pyrrolidine-1-carboxamide and the pharmaceutically acceptable salts or solvates thereof.

In another embodiment, the invention relates to compounds of formula (I) having a minimal inhibitory concentration (MIC) against *Acinetobacter baumannii* of less than about 50 μg/mL, preferably of less than about 25 μg/mL, and more preferably of less than about 10 μg/mL, in an assay as the one described in Example 31.

In another embodiment, the invention relates to compounds of formula (I) having (a) a MIC against *Acinetobacter baumannii* of less than about 50 μg/mL, preferably of less than about 25 μg/mL, and more preferably of less than about 10 μg/mL; and (b) a MIC greater than about 100 μg/mL against at least one of the following bacteria: *Staphylococcus aureus*, *Streptococcus pneumoniae*, *Enterococcus faecium*, *Pseudomonas aeruginosa*, *Klebsiella pneumoniae* and *Escherichia coli*, preferably against at least two of these bacteria, and still more preferably against at least three of these bacteria; in an assay as the one described in Example 31.

Use of the Compounds

As shown in Example 31, surprisingly, the compounds of the present invention showed high antimicrobial activity against the bacteria *A. baumannii*, with minimal inhibitory concentration (MIC) values equal to or less than 25 μg/mL, or even lower, for all the assayed compounds, while they were inactive against the other bacteria tested, i.e. *Staphylococcus aureus* (*S. aureus*), *Streptococcus pneumoniae* (*S. pneumoniae*), *Enterococcus faecium* (*E. faecium*), *Pseudomonas aeruginosa* (*P. aeruginosa*), *Klebsiella pneumoniae* (*K. pneumoniae*) and *Escherichia coli* (*E. coli*), with MIC values greater than 128 for almost all the compounds.

Therefore, a second aspect of the present invention is a compound of formula (I), or a pharmaceutically acceptable salt or solvate thereof, for use as a medicament.

A third aspect of the present invention is a compound of formula (I), or a pharmaceutically acceptable salt or solvate thereof, for use as antibacterial agent, preferably for treating or preventing *A. baumannii* infections.

A preferred embodiment relates to any of the particular and preferred embodiments of compounds formula (I) above disclosed in relation with the first aspect of the present invention for use as antibacterial agents, preferably for treating or preventing *A. baumannii* infections.

This aspect of the present invention can be similarly reformulated as a method for treating bacterial infections in a subject in need thereof, comprising administering an effective amount of a compound of formula (I) as defined above, or a pharmaceutically acceptable salt or solvate thereof, to the subject.

Another aspect of the present invention relates to the use of a compound of formula (I) as defined above, or a pharmaceutically acceptable salt or solvate thereof, as antibacterial agent.

This aspect of the invention can particularly be reformulated as a method for treating a *A. baumannii* infection in a subject in need thereof, comprising administering an effective amount of a compound of formula (I) as defined above, or a pharmaceutically acceptable salt or solvate thereof, to the subject.

Still another aspect of the present invention relates to the use of a compound of formula (I) as defined above, or a pharmaceutically acceptable salt or solvate thereof, for treating *A. baumannii* infections.

The compounds of the present invention may be used without limitation for the treatment of all infections caused by *A. baumannii*. For example, they can be used for treating pneumonia, particularly ventilator-associated pneumonia; surgical site infections; wound infections; skin and soft tissue infections; urinary tract infections; post-operative meningitis; any kind of catheter-related infection, for example catheter-associated urinary tract infection; or bloodstream infection.

As used herein the terms "treatment" or "treating" refer to both prophylactic treatment and therapeutic treatment of *A. baumannii* infections i.e. to preventing or inhibiting the infection from occurring in a subject that may be predisposed to be infected but has not yet been diagnosed as having the infection, and to reducing or eliminating the infection after its onset in a subject, as well as to relieving and alleviating its associated symptoms.

Particularly, the terms "prevention" or "preventing" refer more specifically to prophylactic treatment of *A. baumannii* infections i.e. to preventing or inhibiting the infection from occurring in a subject that may be predisposed to be infected but has not yet been diagnosed as having the infection.

As used herein the term "subject" is referred to human beings.

As used herein the term "in a subject in need thereof" relates to both a subject who has not been infected but that may be predisposed to acquire the infection as well as to a subject who has been infected with *A. baumannii*.

The compounds of the present invention are administered in a dose which is therapeutically active for treating the infections, and the skilled in the art will have no difficulty for adjusting the exact dose to be administered based on the kind of patient, the specific infection to be treated and its severity.

Typically, the compounds of the invention are administered in an amount ranging from 1 to 20 mg/kg of body weight.

In another embodiment, due to the high activity of the compounds of formula (I) against *A. baumannii*, these compounds can be used in therapy in combination with other antibacterials, typically with broad-spectrum antibacterials, which may have less activity or be not active specifically against *A. baumannii*, to thus reinforce the antibacterial effectiveness of the therapy. The compounds of formula (I) may be combined with any kind of antibacterial agent used in therapy, for example, with β-lactam antibiotics, such as penicillins, cephalosporins, monobactams or carbapenems, among others.

The combination of the compound of formula (I) with an additional antibacterial agent may be performed by administering both substances as a fixed-dose combination in the form of a single pharmaceutical dosage form or, alternatively, both drugs can be administered independently, according to a therapeutic combination schedule.

Alternatively, the compound of formula (I) may be combined with another antibacterial agent by chemically bonding both compounds to form a single molecule. For example a compound of formula (I) may be attached to a carbapenem-type antibacterial compound, to form a dual compound, having, for example, the following formula:

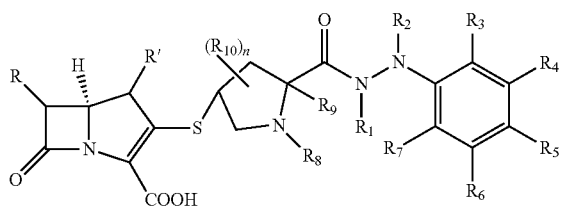

Pharmaceutical Compositions

A fourth aspect of the invention relates to a pharmaceutical composition which comprises a compound of formula (I) or a pharmaceutical acceptable salt or solvate thereof and at least one pharmaceutically acceptable excipient and/or carrier.

The pharmaceutical composition that is an aspect of the present invention can be adapted to any form of administration, for example for oral, parenteral, by inhalation, rectal, transdermal or topical administration. Likewise, depending on the intended route, the composition may be in solid, liquid, or semi-solid form, and all of them are encompassed within the scope of the present invention.

The excipients suitable to be used in the pharmaceutical composition as well as their preparation methods will vary depending on the form and intended route of administration.

Solid compositions for oral use include, for example, tablets, capsules, and granulates. They may contain excipients such, for example, anticaking agents, binders, diluents, disintegrating agents, glidants, lubricants, flavoring agents and sweetening agents. Tablets can be coated with diverse coating agents. Capsules can be either hard capsules or soft capsules as are well known in the art.

Liquid forms for oral administration include emulsions, solutions, suspensions and syrups and can incorporate diverse pharmaceutically acceptable carriers or excipients, such as a liquid vehicle, emulsifying agents, suspending agents, flavoring agents, coloring agents, buffering agents, preservative agents, and diluents.

Injectable preparations comprise sterile solutions, suspensions or emulsions in aqueous or non-aqueous solvents such as propylene glycol, polyethylene glycol or vegetable oils, and can be administered intravenously, subcutaneously or intramuscularly.

Compositions for rectal administration can be in the form of suppositories, for example on an oily base. They may contain other excipients such adsorbents, surface-active agents, antioxidants, preservatives and colorants.

Compositions for topical administration can be in form of creams, gels, ointments or pastes, for example. They may contain excipients such emulsifiers, viscosity-increasing agents, preservatives, antioxidants, and stabilizing agents.

In each case, the pharmaceutical compositions can be prepared using standard methods that are well known to the skilled in the art such as those described in handbooks of pharmaceutical technology, for example the book *Remington The Science and Practice of Pharmacy*, 20$^{th}$ edition, Lippincott, Williams & Wilkins, Philadelphia, 2000 [ISBN: 0-683-306472].

Also the excipients and/or carriers to be used in such compositions are well known, as disclosed for example, in the book R. C. Rowe, P. J. Sheskey and M. E. Quinn, *Handbook of Pharmaceutical Excipients*, 6$^{th}$ edition, Pharmaceutical Press, London, 2009 [ISBN: 978 0 85369 792 3].

Such compositions typically contain from 1 to 40% by weight of compound of formula (I) as active ingredient, the remainder of the composition being pharmaceutical carriers and/or excipients.

Optionally, the pharmaceutical composition can contain an additional active ingredient, in combination with the compound of formula (I), preferably the pharmaceutical composition can contain another antibacterial agent.

Process for Preparing the Compounds of the Invention

A fifth aspect of the present invention relates to a process for the preparation of a compound of formula (I) as defined above, or a pharmaceutically acceptable salt or solvate thereof, which comprises reacting a compound of formula (II)

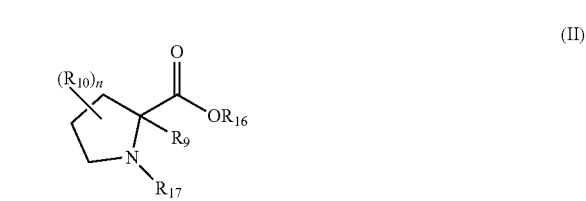

with a compound of formula (III) or a pharmaceutically acceptable salt or solvate thereof:

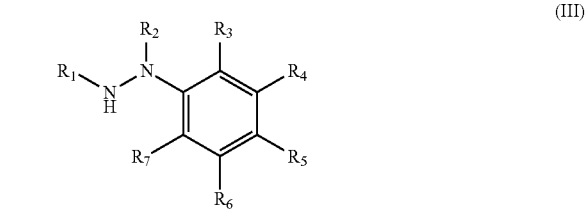

wherein $R_{16}$ is hydrogen or a $C_{1-4}$alkyl, $R_{17}$ is hydrogen or $R_8$, and wherein n and $R_1$ to $R_{15}$, have the same meaning as defined above in relation to compounds of formula (I).

The process can be represented according to the Scheme I:

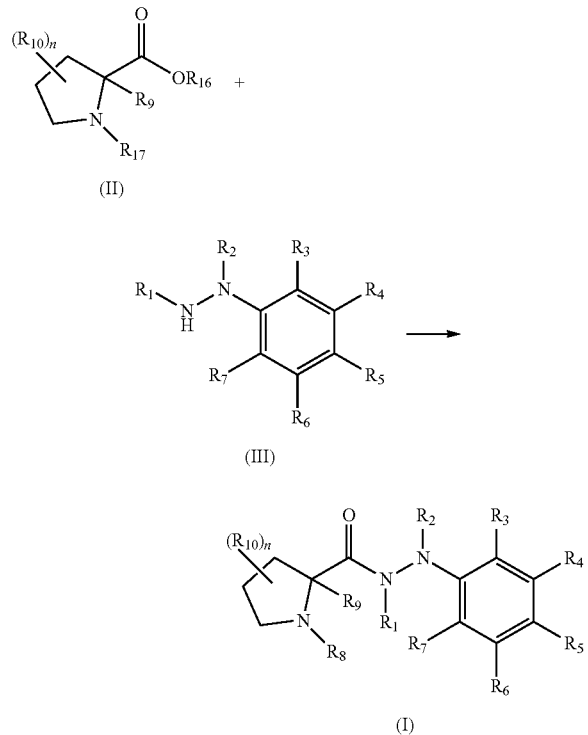

As it is well known to the skilled in the art, the use of conventional protecting groups may be necessary to prevent undesired reactions of some reactive or labile groups. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, "*Protecting Groups in Organic Synthesis*", Third Edition, Wiley, New York, 1999, and the references cited therein.

For example, the process may involve the reaction of an amino-protected form of the compound of formula (II), or/and an amino-protected form of the compound of formula (III), and the process may be followed, if necessary, by the removal of any protective groups that may be present.

In one embodiment $R_{17}$ is $R_8$ and the compound of formula II is a compound of formula ($II_a$). According to this embodiment, the compound of formula (I) can be directly obtained after the coupling reaction between the compound of formula ($II_a$) and the compound of formula (III), followed, if necessary, by the removal of any protective groups that may be present (Method-A).

In another embodiment $R_{17}$ is hydrogen and the compound of formula (II) is a compound of formula ($II_b$). According to this embodiment, the compound of formula ($II_b$), optionally in protected form, is first coupled with the compound of formula (III), to form a compound of formula (IV), and the group $R_8$ can be introduced after the coupling reaction (Method-B), as represented below in Scheme II.

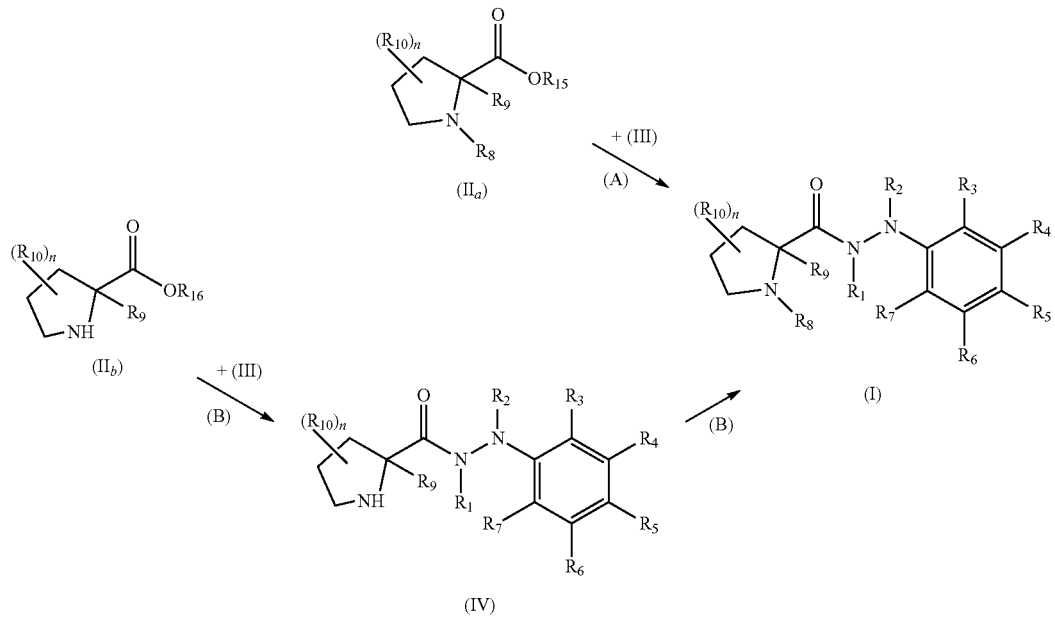

To protect the amine group of the pyrrolidine ring, as well as any other amine group which may need to be protected, any suitable protecting group may be used, for example, the tert-butoxycarbonyl protecting group (Boc) or the carboxybenzyl protecting group (Cbz, or Z) may be used.

In another embodiment, the compound of formula (I) obtained according to the process of Scheme I can be converted into another compound of formula (I) by converting one or more of the radicals $R_1$, $R_2$, $R_3$, $R_4$, $R_5$, $R_6$, $R_7$, $R_8$, $R_9$ and $R_{10}$ (if present) into other radicals $R_1$, $R_2$, $R_3$, $R_4$, $R_5$, $R_6$, $R_7$, $R_9$, and $R_{10}$ respectively, or adding a further $R_{10}$ radical, or removing an $R_{10}$ radical, using known procedures.

The coupling reaction between the compound of formula (II), either (II$_a$) or (II$_b$), and the compound of formula (III), to form an amide bond, is preferably performed in the presence of a coupling agent, as are well known to the skilled in medicinal chemistry. Among others, the following coupling agents may be used: ethyl-(N',N'-dimethylamino)propylcarbodiimide hydrochloride (also known as EDC.HCl), or (1-[bis(dimethylamino)methylene]-1H-1,2,3-triazolo[4,5-b]pyridinium-3-oxid hexafluorophosphate) (also known as HATU). Also, the coupling reaction can be performed using trimethylaluminium (AlMe$_3$) as coupling aid.

Compounds (II) and (III) are suitably reacted in the presence of a coupling agent and in the presence of a base. Suitable bases include, but are not limited to, N,N-diisopropylethylamine (DIPEA), triethylamine (TEA), 4-dimethylaminopyridine (DMAP), or mixtures thereof.

The coupling reaction can take place in an inert organic solvent. Suitable organic solvents are, for example, aromatic hydrocarbons such as benzene, toluene or xylene; halogenated hydrocarbons such as dichloromethane, chloroform or dichloroethane; ethers, such as tetrahydrofuran (THF), dioxane, diethylether or diisopropyl ether; nitriles such as acetonitrile or propionitrile; ketones such as acetone, methyl ethyl ketone or diethyl ketone; alcohols, such as methanol, ethanol, n-propanol, isopropanol or n-butanol; and also dimethylformamide (DMF) or dimethylsulfoxide (DMSO), or mixtures thereof. Preferred solvents are dichloromethane, toluene, tetrahydrofuran and dimethylformamide.

A preferred method for carrying out the coupling reaction of compound (II) with compound (III), as defined above, involves using the coupling agent HATU, more preferably in the presence of the base DIPEA. Preferably, the reaction is carried out using dimethylformamide as solvent, and at about room temperature.

Another preferred method for carrying out the coupling reaction of compound (II) with compound (III), as defined above, involves using the coupling agent EDC.HCl, more preferably in the presence of the base DMAP, and optionally in the presence of hydroxybenzotriazole (HOBt). Preferably, the reaction is carried out using dichloromethane as solvent, and at about room temperature.

Another preferred method for carrying out the coupling reaction of compound (II$_b$) with compound (III), for example when $R_{16}$ is methyl or ethyl, involves using trimethylaluminium as a coupling aid. Preferably, this reaction can be carried out in presence of triethylamine. The solvent is preferably selected from toluene, tetrahydrofuran or mixtures thereof. Preferably the solvent is toluene. The reaction is preferably carried out at a temperature in the range 50-130° C. For example, the reaction can be carried out in a microwave reactor.

It will be appreciated that while some preferred conditions are herewith disclosed for carrying out the processes, such as temperature, reagents, or solvents, for example, it will be matter of routine for the skilled in the art to adjust such conditions to each particular case to achieve optimized results.

Compounds of formula (II) and formula (III) are either commercially available or can be prepared using methods known to the skilled in the art.

For example, a compound of formula (II$_a$) can be obtained from a compound of formula (II$_b$) by attaching a group $R_8$ to the N atom of the pyrrolidine ring using known methods.

For example, when $R_8$ is a $C_{1-6}$alkyl the compound of formula (II$_a$) can be obtained by N-alkylation of pyrrolidine according to methods well known in the art, for example, using alkyl halides or alcohols as alkylating agents, or by reductive alkylation by means of an aldehyde or ketone in the presence of a reducing agent.

When $R_8$ is a —CONH$_2$ group, the compound of formula (II$_a$) can be obtained, for example, by reacting the corresponding compound of formula (IIb) with potassium cyanate (KOCN).

When $R_8$ is a —CONR$_{13}$R$_{14}$ group, the compound of formula (II$_a$) can be obtained, for example, by reacting the corresponding compound of formula (II$_b$) with ClCONR$_{13}$R$_{14}$.

Alternatively, when $R_8$ is a —CONR$_{13}$R$_{14}$ group, the compound of formula (II$_a$) can be obtained, for example, by a transacylation reaction promoted by carbonyldiimidazole, as represented in Scheme III:

SCHEME III

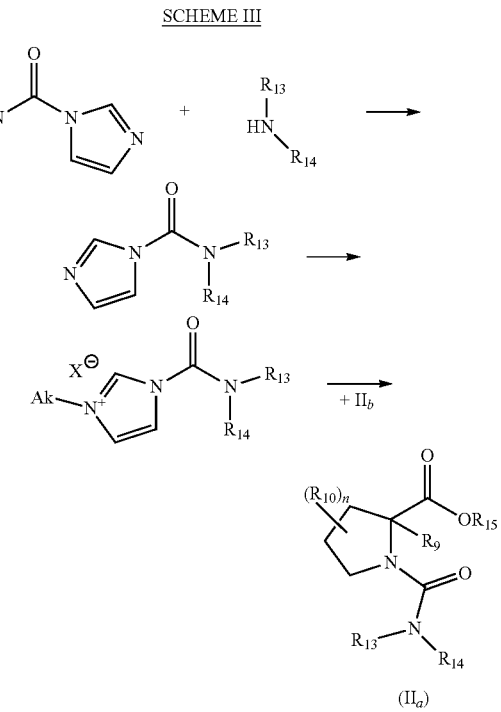

The compounds of the invention, as well as the intermediate products, can be prepared by the methods described herein, or small variations thereof, as well as using alternative methods, as will be matter of routine to the skilled in the art.

The following examples are provided by way of illustration and should not be construed as limiting the present invention.

EXAMPLES

Abbreviations:
Boc: tert-butoxycarbonyl
(Boc)$_2$O or Boc anhydride: di-tert-butyl dicarbonate
Cbz: carboxybenzyl
DCM: dichloromethane
DIPEA: N,N-diisopropylethylamine
DMF: dimethylformamide
EDC.HCl: ethyl-(N,N'-dimethylamino)propylcarbodiimide hydrochloride
EtOAc: ethyl acetate
HATU: (1-[bis(dimethylamino)methylene]-1H-1,2,3-triazolo[4,5-b]pyridinium-3-oxid hexafluorophosphate)
LiHMDS: lithium bis(trimethylsilyl)amide
mCPBA: meta-chloroperoxybenzoic acid
MeOH: methanol
Pd/C: palladium on activated charcoal
TEA: triethylamine
THF: tetrahydrofuran General Methods:

Moisture and oxygen sensitive reactions were conducted in dry glassware (Schlenk flasks sealed with rubber septa) under nitrogen.

Solvents

All solvents used were of analytical-grade quality and if not otherwise mentioned demineralised water was used.

Water-free solvents were freshly distilled under N$_2$ atmosphere prior to use.
Tetrahydrofuran (THF) from sodium-benzophenone ketyl,
Methanol form magnesium methanolate,
Dichloromethane (CH$_2$Cl$_2$) from calcium hydride.

HPLC solvents were of gradient-grade quality and double distilled water was used. All eluents were degassed by sonication prior to use.

Thin Layer Chromatography (TLC)

Thin layer chromatography was conducted with TLC silica gel 60 F$_{254}$ on aluminium sheets (Merck) in a saturated chamber at room temperature.

The spots were visualized under UV light (254 nm) and with reagents such as iodine vapour with additional heating.

As the R$_f$-value strongly depends on the exact ratio of the components of the eluent and some of these components are highly volatile, the given R$_f$-values represent just approximate values.

Flash Column Chromatography (fc)

Flash column chromatography (fc) was conducted with silica gel (100-200 µm) (Spectrochem) as stationary phase. Compressed air was used to push the solvent through the column.

HPLC Method
Model: Waters 2695 Separation Module
Column: Waters XTerra® MS C18 (5 µm) 2.1×250 mm Column
Solvent: A: acetonitrile with 0.05% (v/v) formic acid.
B: water with 0.05% (v/v) formic acid
Gradient:

| time [min] | solvent A [%] | solvent B [min] |
| --- | --- | --- |
| 0.0 | 5.0 | 95.0 |
| 3.0 | 5.0 | 95.0 |
| 10.0 | 100.0 | 0.0 |
| 15.0 | 100.0 | 0.0 |
| 17.0 | 5.0 | 95.0 |
| 18.0 | 5.0 | 95.0 |

Flow rate: 0.30 mL/min
Injection: volume: 2.0 µL
Wavelength: 210-240 nm
Baseline auto zero: 0.0 min
Calculation: use blank subtraction from same series
Integration: manual
Calculation method: area %

All HPLC methods were performed at room temperature.

Mass Spectrometry

The mass spectra were recorded with a Micromass Quatro micro™ API mass spectrometer. As all samples were measured in the positive and negative ion mode, all specified fragments display positively charged ions or radicals. The mass-to-charge ratios m/z and the relative signal intensities [%] of the ions are given.

NMR Spectroscopy $^1$H NMR (500 MHz) spectra were recorded on a Brucker UltraShield (500 MHz), operating at 23° C. Chemical shifts δ are reported in parts per million (ppm) against the reference compound tetramethylsilane and calculated using the chemical shift of the signal of the undeuterated solvent.

Abbreviations for the multiplicities of the signals:
s=singlet, d=doublet, t=triplet, q=quartet, quint=quintet, m=multiplet, dd=doublet of doublets etc.

Intermediate-1: Methyl 5-oxopyrrolidine-2-carboxylate

To a stirred solution of 5-oxopyrrolidine-2-carboxylic acid (10 g, 77.4 mmol) in MeOH (100 mL) thionyl chloride (6.7 mL, 92.9 mmol) was added at 0° C. and the reaction mixture was stirred at 70° C. for 16 h. The progress of the reaction was monitored by TLC. The excess of MeOH was evaporated, the residue was diluted with EtOAc (2×25 mL), the combined organic layer was stirred over K$_2$CO$_3$ (3 g), washed with water (20 mL) and brine (20 mL) and separated the organic layer, dried over anhydrous Na$_2$SO$_4$ and concentrated under reduced pressure. The crude compound was purified by column chromatography (silica gel, 100-200 mesh) to afford the title compound (4.3 g, 39% yield) as brown liquid.

$^1$H NMR (500 MHz, CDCl$_3$) δ: 6.12 (s, 1H), 4.27 (q, J=5.44 Hz, 1H), 3.79 (s, 3H), 2.51-2.41 (m, 1H), 2.43-2.37 (m, 2H), 2.34-2.24 (m, 1H).

Intermediate-2: 1-tert-butyl-2-methyl-5-oxopyrrolidine-1,2-dicarboxylate

To a stirred solution of methyl 5-oxopyrrolidine-2-carboxylate (Intermediate-1) (4.3 g, 30.06 mmol) in DCM (43 mL), DMAP (3.6 g 29.50 mmol) was added, followed by TEA (8.39 mL, 64.79 mmol) and Boc-anhydride (20.7 mL, 90.10 mmol) at 0° C. and the reaction mixture was stirred at room temperature for 1 h. The progress of the reaction was monitored by TLC. The reaction mixture was diluted with DCM (50 mL), washed with aqueous 1N HCl solution (20 mL) followed by brine (20 mL). The organic layer was separated, dried over anhydrous Na$_2$SO$_4$ and concentrated under reduced pressure. The crude compound was purified by column chromatography (silica gel, 100-200 mesh) to afford the title compound (6.8 g, 93% yield) as brown liquid.

$^1$H NMR (400 MHz, CDCl$_3$) δ 4.62 (dd, J=9.32, 2.68 Hz, 1H), 3.77 (s, 3H), 2.70-2.60 (m, 1H), 2.58-2.44 (m, 1H), 2.35-2.28 (m, 1H), 2.06-1.99 (m, 1H), 1.5 (s, 9H).

Intermediate-3: Methyl 1,5-dimethylpyrrolidine-2-carboxylate

The title intermediate was prepared from Intermediate-2 (1-tert-butyl-2-methyl-5-oxopyrrolidine-1,2-dicarboxylate) according to the procedure depicted in Scheme IV.

SCHEME IV

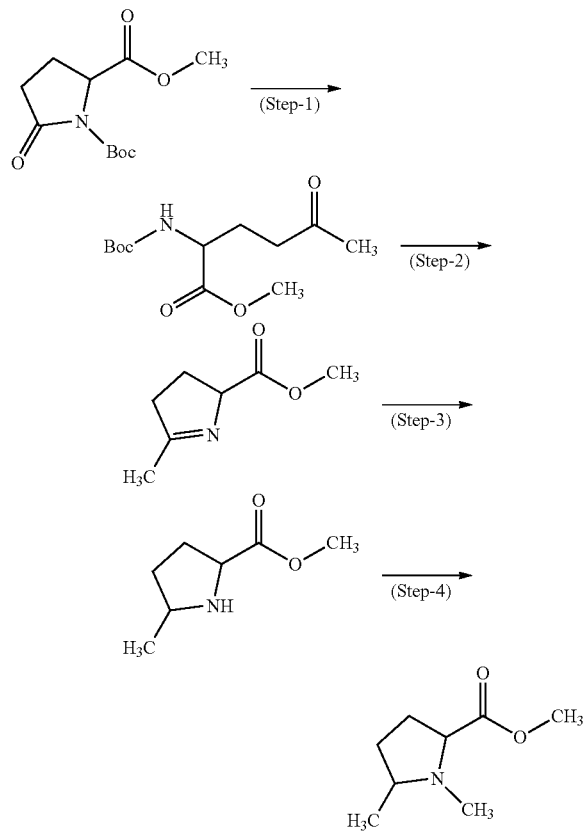

Step 1: Preparation of methyl 2-(tert-butoxycarbonylamino)-5-oxohexanoate

To a stirred solution of 1-tert-butyl-2-methyl-5-oxopyrrolidine-1,2-dicarboxylate (6.8 g, 27.89 mmol) in THF (68 mL), CH$_3$MgBr (3M in ether, 12.12 mL, 36.36 mmol) was added at 0° C. under inert atmosphere and the reaction mixture was stirred for 2 h at the same temperature. The progress of the reaction was monitored by TLC. The reaction mixture was quenched with aqueous NH$_4$Cl solution and the aqueous layer was extracted with EtOAc (2×50 mL). The combined organic layer was washed with water (20 mL) and brine (20 mL), dried over anhydrous Na$_2$SO$_4$ and concentrated under reduced pressure. The crude compound was purified by column chromatography (silica gel, 100-200 mesh) to afford the title compound (3.6 g, 49% yield) as yellow liquid.

$^1$H NMR (400 MHz, CDCl$_3$) δ 5.10 (bs, 1H), 4.25 (s, 1H), 4.12 (d, J=7.04 Hz, 1H), 3.73 (s, 3H), 2.59-2.47 (m, 2H), 2.1 (s, 2H), 2.03 (s, 1H), 1.89-1.84 (m, 1H), 1.4 (s, 9H)

Step 2: Preparation of methyl 5-methyl-3,4-dihydro-2H-pyrrole-2-carboxylate

To a stirred solution of methyl 2-(tert-butoxycarbonylamino)-5-oxohexanoate (6.8 g, 27.89 mmol) in DCM (36 mL), trifluoroacetic acid (5.3 mL, 40.9 mmol) at 0° C. was added and the reaction mixture was stirred for 2 h at room temperature. The progress of the reaction was monitored by TLC. The reaction mixture was concentrated under reduced pressure to afford the title compound (3.6 g, 28% yield) as yellow liquid. The crude compound was used in the next step without purification.

Step 3: Preparation of methyl 5-methylpyrrolidine-2-carboxylate

To a stirred solution of methyl 5-methyl-3,4-dihydro-2H-pyrrole-2-carboxylate (3.6 g, 25.53 mmol) in ethanol (36 mL), Pd/C (10% wet, 1 g) was added under nitrogen atmosphere and the reaction mixture was stirred under hydrogen atmosphere for 16 h at room temperature. The progress of the reaction was monitored by TLC. The reaction mixture was filtered through a pad of celite and the filtrate was concentrated under reduced pressure to afford the title compound (3.5 g, 95% yield) as brown liquid. The crude compound was used in the next step without purification.

Step 4: Preparation of methyl 1,5-dimethylpyrrolidine-2-carboxylate

To a stirred solution of methyl 5-methylpyrrolidine-2-carboxylate (2.2 g, 13.99 mmol) in MeOH (15.4 mL) NaHCO$_3$ (1.29 g, 15.38 mmol) was added at 0° C. After stirring the reaction mixture for 5 min, aqueous formaldehyde (37% wt, 1.14 mL, 30.76 mmol) was added and stirring was continued for 2 h followed by the addition of NaBH$_4$ (0.876 g, 23 mmol) at same temperature. The reaction mixture was stirred for another 1 h at room temperature. The progress of the reaction was monitored by TLC. Excess of MeOH was evaporated, the residue was diluted with water (20 mL), and extracted with EtOAc (2×20 mL). The combined organic layer was washed with water (10 mL) and brine (10 mL), dried over Na$_2$SO$_4$ and concentrated under reduced pressure. The crude compound was purified by column chromatography (silica gel, 100-200 mesh) to afford the title compound as pale brown liquid.

$^1$H NMR (400 MHz, CDCl$_3$) δ 3.75 (t, J=9.08 Hz, 3H), 2.92 (t, J=8.32 Hz, 1H), 2.32 (s, 3H), 2.04-1.92 (m, 1H), 1.87-1.85 (m, 3H), 1.28-1.25 (m, 1H), 1.15 (d, J=5.96 Hz, 3H)

Intermediate-4: (R)-1-carbamoylpyrrolidine-2-carboxylic acid

To a stirred solution of D-Proline (1 g, 8.69 mmol) in water (50 mL) concentrated HCl (pH~5) was added, followed by KOCN (2.11 g, 26.01 mmol) and the reaction mixture was stirred at 60° C. for 4 h. The progress of the reaction was monitored by TLC. The reaction mixture was cooled to room temperature, acidified with concentrated HCl (pH~4), the solid formed was filtered, washed with ice-cold water (2×100 mL) and dried under vacuum to afford the title compound (460 mg, 33% yield) as white solid.

Intermediate-5:
(S)-1-carbamoylpyrrolidine-2-carboxylic acid

The title compound (500 mg, 36% yield) was prepared following an analogous procedure as for Intermediate-4, but using L-Proline (1 g, 8.69 mmol), as starting material.

Intermediate-6:
1-carbamoylpyrrolidine-2-carboxylic acid

The title compound (500 mg, 14% yield) was prepared from DL-proline (2.5 g, 21.7 mmol), following an analogous procedure as for Intermediate-4.
$^1$H NMR (400 MHz, DMSO-$d_6$) δ 12.35 (s, 1H), 5.85 (s, 2H), 4.15 (d, J=8.44 Hz, 1H), 3.25 (m, 1H), 2.05 (m, 1H), 1.8 (d, J=5.2 Hz, 3H).

Intermediate-7: (2S,4S)-1-carbamoyl-4-fluoropyrrolidine-2-carboxylic acid

The title compound (260 mg, 79% yield) was prepared from (2S,4S)-4-fluoropyrrolidine-2-carboxylic acid (260 mg, 1.87 mmol), following an analogous procedure as for Intermediate-4.

Intermediate-8: Methyl pyrrolidine-2-carboxylate

To a stirred solution of pyrrolidine-2-carboxylic acid (1 g, 8.69 mmol) in MeOH (10 mL) thionyl chloride (0.75 mL, 10.43 mmol) was added and the reaction mixture was stirred at reflux temperature for 16 h. The progress of the reaction was monitored by TLC. The reaction mixture was concentrated, the residue was diluted with DCM (15 mL), the excess of thionyl chloride was quenched with solid NaHCO$_3$, filtered, and the filtrate was concentrated under reduced pressure to afford the title compound (1.1 g, 98% yield) as pale yellow solid.

Intermediate-9: 1-tert-butyl 2-methyl pyrrolidine-1,2-dicarboxylate

To a stirred solution of methyl pyrrolidine-2-carboxylate (Intermediate-8) (1 g, 7.74 mmol) in DCM (10 mL) TEA (2.7 mL) was added, followed by di-tert-butyl dicarbonate (Boc anhydride, (Boc)$_2$O) (1.86 g, 8.51 mmol) at 0° C. and the reaction mixture was stirred at room temperature for 16 h. The progress of the reaction was monitored by TLC. The reaction mixture was quenched with water (20 mL) and extracted with chloroform (2×20 mL). The combined organic layer was washed with water (10 mL) and brine (10 mL), dried over anhydrous Na$_2$SO$_4$ and concentrated under reduced pressure. The crude compound was purified by column chromatography (silica gel 100-200 mesh) to afford the title compound (1.3 g, 73% yield) as pale yellow liquid.

Intermediate-10: 1-tert-butyl 2-methyl 2-methylpyrrolidine-1,2-dicarboxylate

To a stirred solution of 1-tert-butyl 2-methyl pyrrolidine-1,2-dicarboxylate (Intermediate-9) (2.75 g, 12.00 mmol) in THF (5.5 mL), LiHMDS (Lithium bis(trimethylsilyl)amide) (1 M in n-hexane, 19.21 mL, 19.23 mmol) was added at −20° C. After stirring the reaction mixture for 1.5 h at same temperature, iodomethane (MeI) (2.72 g, 19.16 mmol) was added and stirring was continued at room temperature for 18 h. The progress of the reaction was monitored by TLC. The reaction mixture was quenched with NH$_4$Cl solution and extracted with EtOAc (2×30 mL). The combined organic layer was washed with water (15 mL) and brine (15 mL), dried over anhydrous Na$_2$SO$_4$ and concentrated under reduced pressure. The crude compound was purified by column chromatography (silica gel 100-200 mesh) to afford the title compound (1.5 g, 51% yield) as pale yellow liquid.
GCMS m/z: 243

Intermediate-11: Methyl 1-hydroxypyrrolidine-2-carboxylate

The title compound was prepared from methyl pyrrolidine-2-carboxylate (Intermediate-8) according to the procedure depicted in Scheme V:

SCHEME V

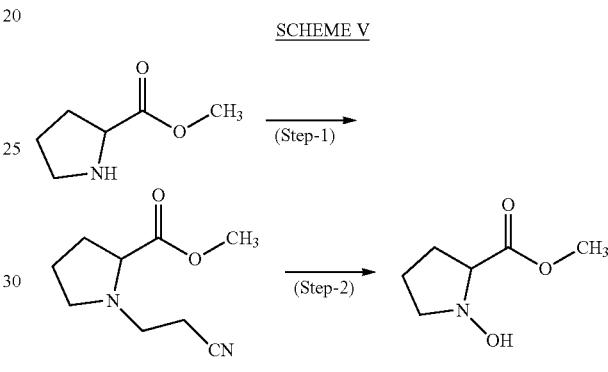

Step 1: Preparation methyl 1-(2-cyanoethyl)pyrrolidine-2-carboxylate

To a stirred solution of methyl pyrrolidine-2-carboxylate (Intermediate-8) (250 mg, 1.937 mmol) in MeOH (2 mL), acrylonitrile (0.15 mL, 2.264 mmol) was added and the reaction mixture was stirred at room temperature for 16 h. The progress of the reaction was monitored by TLC. The reaction mixture was concentrated under reduced pressure to afford the title compound (200 mg, 56% yield) as colourless liquid. The crude compound was used in the next step without purification.
$^1$H NMR (400 MHz, CDCl$_3$) δ 3.75 (s, 3H), 3.35 (bs, 1H), 3.22-3.20 (m, 1H), 3.19-3.10 (m, 1H), 2.86-2.81 (m, 1H), 2.58-2.55 (m, 3H), 2.15-2.13 (m, 1H), 2.00-1.85 (m, 3H).

Step 2: Preparation of methyl 1-hydroxypyrrolidine-2-carboxylate

To a stirred solution of methyl 1-(2-cyanoethyl)pyrrolidine-2-carboxylate (1 g, 5.49 mmol) in DCM (15 mL), mCPBA (1.9 g 8.715 mmol) was added at 0° C. and the reaction mixture was stirred at room temperature for 16 h. The progress of the reaction was monitored by TLC. The reaction mixture was concentrated under reduced pressure. The crude compound was purified by column chromatography (silica gel, 100-200 mesh) to afford the title compound (150 mg, 18% yield) as colourless liquid.
$^1$H NMR (400 MHz, DMSO-$d_6$) δ 8.1 (s, 1H), 3.6 (s, 3H), 3.4 (t, J=7.8 Hz, 1H), 3.03-3.08 (m, 1H), 2.7 (q, J=8.24 Hz, 1H), 2.05-1.98 (m, 1H), 1.77-1.71 (m, 3H).

Intermediate-12: Methyl 1-(dimethylcarbamoyl)pyrrolidine-2-carboxylate

To a stirred solution of methyl pyrrolidine-2-carboxylate (200 mg, 1.74 mmol) in DCM (10 mL) TEA (0.72 mL, 5.27 mmol) was added, followed by dimethylcarbamic chloride (0.19 mL, 2.08 mmol) and the reaction mixture was stirred at room temperature for 2 h. The progress of the reaction was monitored by TLC. The reaction mixture was diluted with water (10 mL) and extracted with DCM (2×15 mL). The combined organic layer was washed with water (10 mL) and brine (10 mL), dried over anhydrous $Na_2SO_4$ and concentrated under reduced pressure to afford the title compound (180 mg, 51% yield) as off-white solid.

Intermediate-13: tert-butyl 4-(2-(methoxycarbonyl) pyrrolidine-1-carbonyl)piperazine-1-carboxylate The title compound was prepared according to the procedure depicted in Scheme VI:

SCHEME VI

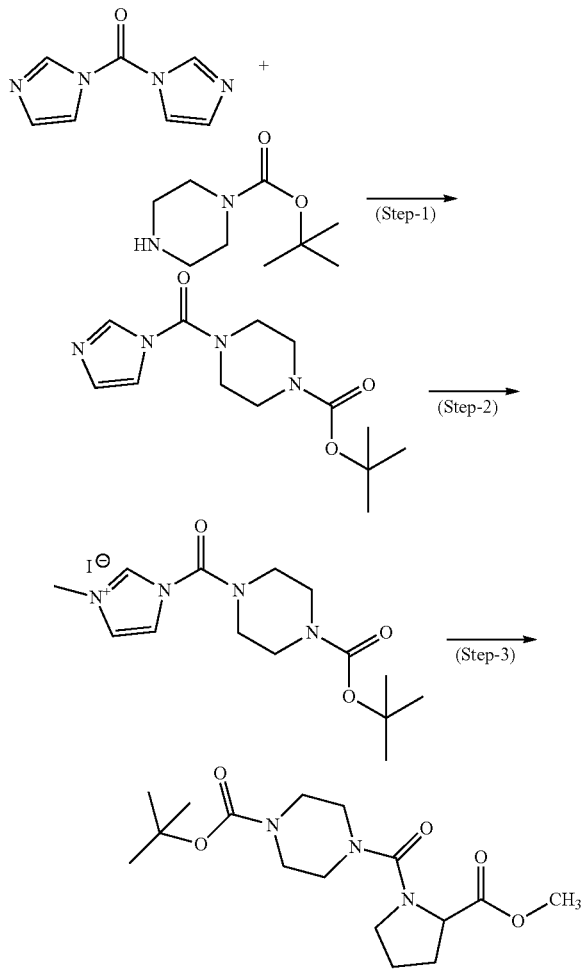

Step 1: Preparation tert-butyl 4-(1H-imidazole-1-carbonyl)piperazine-1-carboxylate To a stirred solution of carbonyldiimidazole (5 g, 30.84 mmol) in DCM (50 mL) TEA (4.33 mL, 30.83 mmol) and Boc-piperazine (5.74 g, 30.83 mmol) were added and the reaction mixture was stirred at room temperature for 16 h. The progress of the reaction was monitored by TLC. The reaction mixture was quenched with water (50 mL) and extracted with DCM (2×50 mL). The combined organic layer was dried over anhydrous $Na_2SO_4$ and concentrated under reduced pressure to afford the title compound (3 g, crude) as off-white solid. The crude compound was used in the next step without purification.

Step 2: Preparation of 1-(4-(tert-butoxycarbonyl) piperazine-1-carbonyl)-3-methyl-1H-imidazol-3-ium iodide To a stirred solution of tert-butyl 4-(1H-imidazole-1-carbonyl)piperazine-1-carboxylate (3 g, 10.67 mmol) in acetonitrile (15 mL), iodomethane (2.64 mL, 42.70 mmol) was added at 0° C. and the reaction mixture was stirred at room temperature for 16 h. The progress of the reaction was monitored by TLC. The solvent was evaporated under reduced pressure to afford the title compound (3 g, crude) as off-white solid. The crude compound was used in the next step without purification.

Step 3: Preparation tert-butyl 4-(2-(methoxycarbonyl)pyrrolidine-1-carbonyl)piperazine-1-carboxylate To a stirred solution of 1-(4-(tert-butoxycarbonyl)piperazine-1-carbonyl)-3-methyl-1H-imidazol-3-ium iodide (3 g, 10.16 mmol) in DCM (30 mL), TEA (1.42 mL, 50.84 mmol) and pyrrolidine-2-carboxylic acid methyl ester (2.62 g, 20.35 mmol) were added and the reaction mixture was stirred at room temperature for 16 h. The progress of the reaction was monitored by TLC. The reaction mixture was quenched with water (50 mL), and extracted with DCM (2×50 mL). The combined organic layer was dried over anhydrous $Na_2SO_4$ and concentrated under reduced pressure. The crude compound was purified by column chromatography to afford the title compound (1 g, 29% yield) as off-white solid.

Intermediate-14: Methyl 1-(morpholine-4-carbonyl)pyrrolidine-2-carboxylate

The title compound was prepared according to the procedure depicted in Scheme VII:

SCHEME VII

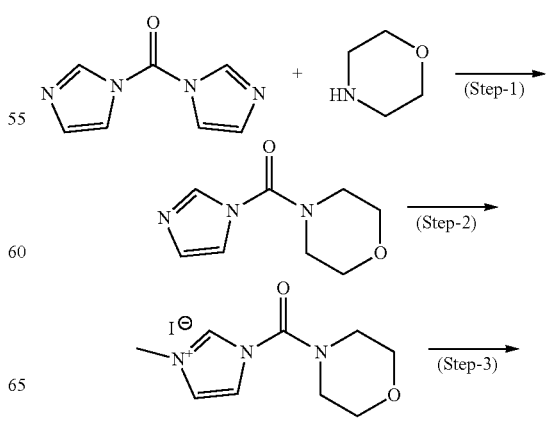

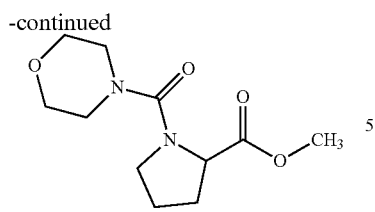

Step 1: Preparation of (1H-imidazol-1-yl)(morpholino)methanone

To a stirred solution of carbonyldiimidazole (5 g, 30.83 mmol) in DCM (50 mL), TEA (4.3 mL, 30.83 mmol), and morpholine (2.5 g, 29.06 mmol) were added and the reaction mixture was stirred at room temperature for 16 h. The progress of the reaction was monitored by TLC. The reaction mixture was quenched with water (20 mL) and extracted with DCM (2×50 mL). The combined organic layer was washed with water (20 mL) and brine (20 mL), dried over anhydrous $Na_2SO_4$ and concentrated under reduced pressure to afford the title compound (3 g, crude) as off-white solid. The crude compound was used in the next step without purification.

Step 2: Preparation of (3-methyl-1-(morpholine-4-carbonyl)-1H-imidazol-3-ium iodide To a stirred solution of (1H-imidazol-1-yl)(morpholino) methanone (3 g, 16.55 mmol) in acetonitrile (15 mL) iodomethane (4.1 mL, 66.22 mmol) was added at 0° C. and the reaction mixture was stirred at room temperature for 16 h. The progress of the reaction was monitored by TLC. The solvent was evaporated under reduced pressure to afford the title compound (2 g, crude) as off-white solid. The crude compound was used in the next step without purification.

Step 3: Preparation of methyl 1-(morpholine-4-carbonyl)pyrrolidine-2-carboxylate To a stirred solution of (3-methyl-1-(morpholine-4-carbonyl)-1H-imidazol-3-ium iodide (2 g, 10.16 mmol) in DCM (30 mL) TEA (7.1 mL, 50.84 mmol) and pyrrolidine-2-carboxylic acid methyl ester (2.62 g, 20.35 mmol) were added and the reaction mixture was stirred at room temperature for 16 h. The progress of the reaction was monitored by TLC. The reaction mixture was quenched with water (20 mL) and extracted with DCM (2×25 mL). The combined organic layer was washed with water (10 mL) and brine (10 mL), dried over anhydrous $Na_2SO_4$ and concentrated under reduced pressure. The crude compound was purified by column chromatography to afford the title compound (1 g, 41% yield) as off-white solid.

Intermediate-15: Ethyl 1-methyl-5-oxopyrrolidine-2-carboxylate

To a stirring solution of sodium hydride (2 equiv) in anhydrous DMF (2 mL) at ice cooled condition under argon atmosphere, a solution of ethyl 5-oxopyrrolidine-2-carboxylate (300 mg in 3 mL DMF) was added dropwise over a time period of 10 min, and the reaction mixture was stirred for 15 min at the same temperature. Next, iodomethane was added and allowed to stirring for 3 h. To quench the reaction a saturated solution of $NH_4Cl$ (5 mL) was added and extracted with DCM (2×10 mL). The combined organic portion was dried over anhydrous sodium sulfate and distilled out under reduced pressure to obtain the title compound (175 mg). LC-MS: 172.2 (M+H).

Intermediate-16: 1,2-dimethylpyrrolidine-2-carboxylic acid

The title compound was obtained by N-methylation of 2-methylpyrrolidine-2-carboxylic acid. Thus, to a stirred solution of 2-methylpyrrolidine-2-carboxylic acid (300 mg) in anhydrous MeOH (10 mL), 1 mL of formaldehyde was added dropwise at 0° C., followed by a catalytic amount of acetic acid, and the reaction mixture was stirred for 10 min at the same temperature. Next, 50 mg of 10% Pd/C was added and the reaction mixture was stirred at room temperature in presence of hydrogen atmosphere for 2 h. The progress of the reaction was monitored by TLC. After complete consumption of starting materials, the reaction mixture was filtered through a celite bed to remove the solid residue which was washed with MeOH for several times. The filtrate was collected and concentrated under reduced pressure to obtain the title compound (300 mg).

LC-MS: 144.18 (M+H)

Intermediate-17: 4-fluoro-1-methylpyrrolidine-2-carboxylic acid

The title compound was obtained by N-methylation of 4-fluoropyrrolidine-2-carboxylic acid, following an analogous procedure as disclosed above for the preparation of Intermediate-16. 150 mg of 4-fluoropyrrolidine-2-carboxylic acid afforded 120 mg of the title compound.

LC-MS: 148.2 (M+H).

Intermediate-18: 3-methyl-3-azabicyclo[3.1.0]hexane-2-carboxylic acid

The title compound was obtained by N-methylation of 3-azabicyclo[3.1.0]hexane-2-carboxylic acid, following an analogous procedure as disclosed above for the preparation of Intermediate-16. 300 mg of 3-azabicyclo[3.1.0]hexane-2-carboxylic acid afforded 300 mg of the title compound.

LC-MS: 144.18 (M+H).

Intermediate-19: 1,4-dimethylpyrrolidine-2-carboxylic acid

The title compound was obtained by N-methylation of 4-methylpyrrolidine-2-carboxylic acid, following an analogous procedure as disclosed above for the preparation of Intermediate-16. 250 mg of 4-methylpyrrolidine-2-carboxylic acid afforded 250 mg of the title compound.

LC-MS: 144.18 (M+H)

Intermediate-20: 1,3-dimethylpyrrolidine-2-carboxylic acid

The title compound was obtained by N-methylation of 3-methylpyrrolidine-2-carboxylic acid, following an analogous procedure as disclosed above for the preparation of Intermediate-16. 250 mg of 3-methylpyrrolidine-2-carboxylic acid afforded 250 mg of the title compound.

LC-MS: 144.18 (M+H)

Intermediate-21: 1-ethylpyrrolidine-2-carboxylic acid

The title compound was obtained by N-ethylation of pyrrolidine-2-carboxylic acid, following an analogous procedure as in the N-methylation disclosed above for the preparation of Intermediate-16, but using acetaldehyde instead of formaldehyde. 1 g of pyrrolidine-2-carboxylic acid afforded 187 mg of the title compound.

LC-MS: 144.18 (M+H)

Intermediate-22: 1-(benzyloxycarbonyl)pyrrolidine-2-carboxylic acid

A mixture of pyrrolidine-2-carboxylic acid (2.5 g, 21.7 mmol), NaOH (2 M solution, 10 mL) and carbobenzoxy chloride (3.7 g, 21.7 mmol) were stirred at room temperature for 6 h. The progress of the reaction was monitored by TLC. The reaction mixture was acidified with 2N HCl and extracted with EtOAc (2×50 mL). The combined organic layer was washed with water (15 mL) and brine (15 mL), dried over anhydrous $Na_2SO_4$ and concentrated under reduced pressure to afford the title compound (1.5 g, 27% yield) as colourless liquid.

Example 1

N'-(4-fluorophenyl)-1,5-dimethypyrrolidine-2-carbohydrazide

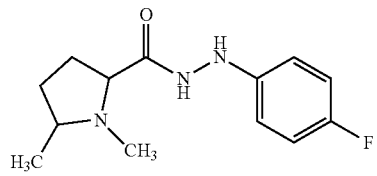

To a stirred solution of methyl 1,5-dimethylpyrrolidine-2-carboxylate (Intermediate-3) (0.3 g, 1.91 mmol) in toluene (6 mL) 4-fluorophenylhydrazine hydrochloride (0.31 g, 1.91 mmol), TEA (0.536 mL, 4.13 mmol) and trimethylaluminum (2M solution in toluene, 0.96 mL, 1.91 mmol) at 0° C. were added and the reaction mixture was stirred at 70° C. in microwave for 1 h. The progress of the reaction was monitored by TLC. The reaction mixture was quenched with ice-cold water (5 mL), extracted with EtOAc (2×20 mL). The combined organic layer was washed with water (5 mL) and brine (5 mL), dried over anhydrous $Na_2SO_4$ and concentrated under reduced pressure. The crude compound was purified by column chromatography (silica gel, 100-200 mesh) to afford the title compound (18 mg, 3% yield) as pale brown solid.

$^1$H NMR (400 MHz, DMSO-$d_6$) δ 9.98 (s, 1H), 7.64 (s, 1H), 6.95 (t, J=8.72 Hz, 2H), 6.7 (q, 4.68 Hz, 2H), 3.4 (s, 1H), 3.1 (s, 1H), 2.3 (s, 3H), 2.05-2.00 (m, 2H), 1.68-1.65 (m, 1H),1.40-1.30 (m, 1H), 0.93 (d, J=6 Hz, 3H)

LC-MS m/z (M+H): 252.2

Purity (HPLC): 99.3%

Example 2

(R)-2-(2-(4-fluorophenyl)hydrazinecarbonyl)pyrrolidine-1-carboxamide

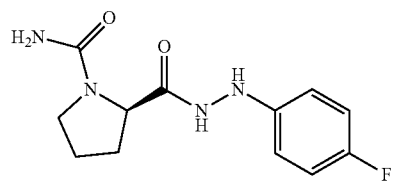 [SMILES: NC(=O)N1CCC[C@@H]1C(=O)NNc1ccc(F)cc1]

To a stirred solution of (R)-1-carbamoylpyrrolidine-2-carboxylic acid (Intermediate-4) (500 mg, 3.16 mmol) in DMF (5 mL) DIPEA (1.61 mL, 9.23 mmol), HATU (1.44 g 3.79 mmol) and 4-fluorophenylhydrazine hydrochloride (563 mg, 3.48 mmol) were added at 0° C. under nitrogen atmosphere and the reaction mixture was stirred at room temperature for 3 h. The progress of the reaction was monitored by TLC. The reaction mixture was quenched with ice-cold water (25 mL) and extracted with EtOAc (2×15 mL). The combined organic layer was washed with water (10 mL) and brine (10 mL), dried over anhydrous $Na_2SO_4$ and concentrated under reduced pressure. The crude compound was purified by column chromatography (silica gel, 100-200 mesh) to afford the title compound (28 mg) as off-white solid.

$^1$H NMR (400 MHz, DMSO-$d_6$) δ 9.61 (d, J=2.6 Hz, 1H), 7.59 (d, J=2.4 Hz, 1H), 6.91 (t, J=8.8 Hz, 2H), 6.75-6.72 (m, 2H), 5.85 (s, 2H), 4.21-4.18 (m, 1H), 3.41-3.30 (m, 1H), 3.25-3.19 (m, 1H), 2.09-1.97 (m, 1H), 1.94-1.78 (m, 3H)

LC-MS m/z (M−H): 265.1

Purity (HPLC): 99.8%

Example 3

(S)-2-(2-(4-fluorophenyl) hydrazinecarbonyl) pyrrolidine-1-carboxamide

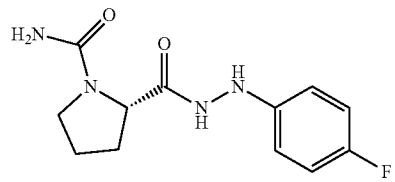 [SMILES: NC(=O)N1CCC[C@H]1C(=O)NNc1ccc(F)cc1]

The title compound was prepared following an analogous procedure as in Example 2, but using (S)-1-carbamoylpyrrolidine-2-carboxylic acid (Intermediate-5) as starting material. 500 mg of Intermediate-5 afforded 35 mg (4% yield) of the title compound as a off-white solid.

$^1$H NMR (400 MHz, DMSO-$d_6$) δ 9.62 (s, 1H), 7.60 (s, 1H), 6.91 (t, J=8.88 Hz, 2H), 6.75-6.72 (m, 2H), 5.86 (s, 2H), 4.21-4.18 (m, 1H), 3.38-3.31 (m, 1H), 3.25-3.19 (m, 1H), 2.06-1.91 (m, 1H), 1.89-1.79 (m, 3H)

LC-MS m/z (M−H): 265.0

Purity (HPLC): 99.6%

Examples 4-12

Examples 4-12 were prepared following analogous procedures as the one disclosed for Example 2, using 1-carbamoylpyrrolidine-2-carboxylic acid (Intermediate-6) and the suitable hydrazine as starting materials:

Example 4

2-(2-(4-fluorophenyl)hydrazinecarbonyl)pyrrolidine-1-carboxamide

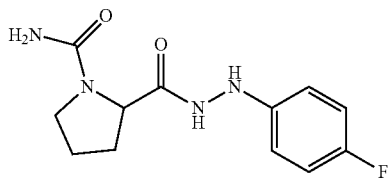 [SMILES: NC(=O)N1CCCC1C(=O)NNc1ccc(F)cc1]

$^1$H NMR (400 MHz, DMSO-d$_6$) δ 9.6 (s, 1H), 7.6 (s, 1H), 6.9 (t, J=8.88 Hz, 2H), 6.80-6.70 (m, 2H), 5.85 (s, 2H), 4.2 (dd, J=3.04 Hz, J=8.44 Hz, 1H), 3.4-3.3 (m, 1H), 3.3-3.2 (m, 1H), 2.1-2.0 (m, 1H), 1.90-1.70 (m, 3H)
LC-MS m/z (M−H): 265
Purity (HPLC): 99.0%
Melting point: 140-144° C.

Example 5

2-(2-(4-fluoro-2-methylphenyl)hydrazine-1-carbonyl)pyrrolidine-1-carboxamide

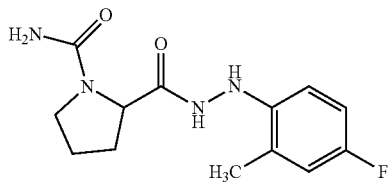 [SMILES: Cc1cc(F)ccc1NNC(=O)C1CCCN1C(N)=O]

$^1$H NMR (400 MHz, DMSO-d$_6$) δ 9.63 (d, J=2.3 Hz, 1H), 6.91(d, J=2.1 Hz, 1H), 6.85-6.72 (m, 3H), 5.85 (s, 2H), 4.25-4.22 (m, 1H), 3.42-3.38 (m, 1H), 3.29-3.20 (m, 1H), 2.12 (s, 3H), 2.07-1.97 (m, 1H), 1.96-1.83 (m, 3H)
LC-MS m/z (M−H): 279.2
Purity (HPLC): 99.8%

Example 6

2-(2-(3,5-difluorophenyl)hydrazinecarbonyl)pyrrolidine-1-carboxamide

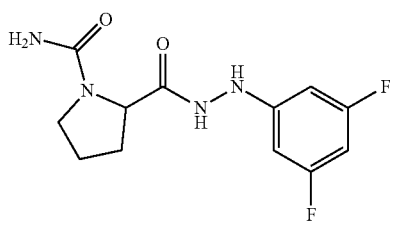 [SMILES: NC(=O)N1CCCC1C(=O)NNc1cc(F)cc(F)c1]

$^1$H NMR (400 MHz, DMSO-d$_6$) δ 9.73 (s, 1H), 8.22 (s, 1H), 6.40-6.33 (m, 3H), 5.90 (s, 2H), 4.19-4.16 (m, 1H), 3.41-3.36 (m, 1H), 3.24-3.20 (m, 1H), 2.09-2.02 (m, 1H), 1.95-1.80 (m, 3H)
LC-MS m/z (M−H): 283.1
Purity (HPLC): 99.6%

Example 7

2-(2-(4-(trifluoromethoxy)phenyl)hydrazinecarbonyl)pyrrolidine-1-carboxamide

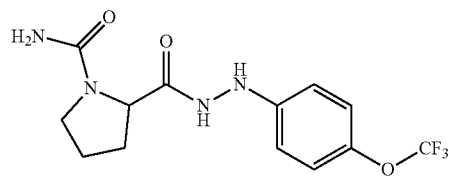

$^1$H NMR (400 MHz, DMSO-d$_6$) δ 9.67 (d, J=2.0 Hz, 1H), 7.89 (d, J=1.9 Hz, 1H), 7.06 (d, J=8.6 Hz, 2H), 6.79 (d, J=8.9 Hz, 2H), 5.86 (s, 2H), 4.22-4.19 (m, 1H), 3.41-3.36 (m, 1H), 3.29-3.20 (m, 1H), 2.08-2.01 (m, 1H), 1.92-1.78 (m, 3H)
LC-MS m/z (M−H): 331.1
Purity (HPLC): 99.3%

Example 8

2-(2-(4-(trifluoromethyl)phenyl)hydrazinecarbonyl)pyrrolidine-1-carboxamide

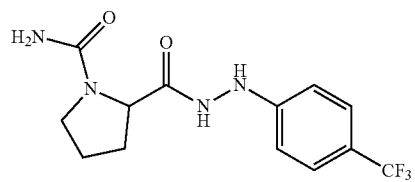 [SMILES: NC(=O)N1CCCC1C(=O)NNc1ccc(C(F)(F)F)cc1]

1H NMR (400 MHz, DMSO-d6) δ 9.77 (s, 1H), 8.29 (s, 1H), 7.38 (d, J=8.3 Hz, 2H), 6.84 (d, J=8.3 Hz, 2H), 5.86 (s, 2H), 4.23-4.20 (m, 1H), 3.39 (s, 1H), 3.29-3.20 (m, 1H), 2.12-2.03 (m, 1H), 1.95-1.81 (m, 3H)
LC-MS m/z (M−H): 315.2
Purity (HPLC): 99.8%

Example 9

2-(2-(4-chloro-2-fluorophenyl)hydrazinecarbonyl)pyrrolidine-1-carboxamide

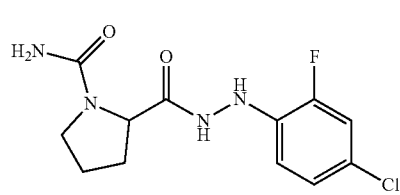 [SMILES: NC(=O)N1CCCC1C(=O)NNc1ccc(Cl)cc1F]

$^1$H NMR (400 MHz, DMSO-d$_6$) δ 9.72 (s, 1H), 7.75 (s, 1H), 7.21 (d, J=10.7 Hz, 1H), 7.19-6.92 (m, 2H), 5.87 (s,

2H), 4.22-4.19 (m, 1H), 3.41-3.35 (m, 1H), 3.29-3.20 (m, 1H), 2.07-2.00 (m, 1H), 1.95-1.79 (m, 3H)
LC-MS m/z (M−H): 299.1
Purity (HPLC): 99.9%

Example 10

2-(2-(4-methoxyphenyl)hydrazinecarbonyl)pyrrolidine-1-carboxamide

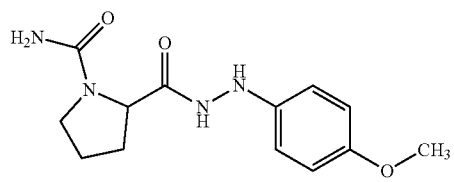 [SMILES: COc1ccc(NNC(=O)C2CCCN2C(N)=O)cc1]

¹H NMR (400 MHz, DMSO-d₆) δ 9.55 (d, J=2.7 Hz, 1H), 7.28 (s, 1H), 6.77 (s, 4H), 5.84 (s, 2H), 4.21-4.19 (m, 1H), 3.65 (s, 3H), 3.38-3.31 (m, 1H), 3.24-3.18 (m, 1H), 2.05-1.90 (m, 1H), 1.88-1.79 (m, 3H)
LC-MS m/z (M−H): 277.0
Purity (HPLC): 99.7%

Example 11

2-(2-(2,3-dihydrobenzo[b][1,4]dioxin-6-yl) hydrazinecarbonyl)pyrrolidine-1-carboxamide

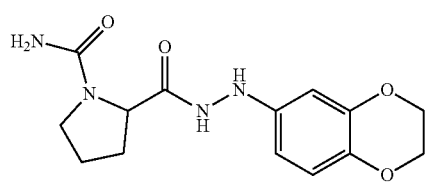 [SMILES: NC(=O)N1CCCC1C(=O)NNc1ccc2c(c1)OCCO2]

¹H NMR (400 MHz, DMSO-d₆) δ 9.51 (s, 1H), 7.21-6.95 (m, 1H), 6.58 (d, J=8.2 Hz, 1H), 6.25-6.23 (m, 2H), 5.82 (s, 2H), 4.21-4.10 (m, 5H), 3.37-3.25 (m, 1H), 3.22-3.15 (m, 1H), 2.10-1.95 (m, 1H), 1.87-1.81 (m, 3H)
LC-MS m/z (M+H): 306.2
Purity (HPLC): 99.7%

Example 12

2-(2-(4-sulfamoylphenyl)hydrazinecarbonyl)pyrrolidine-1-carboxamide

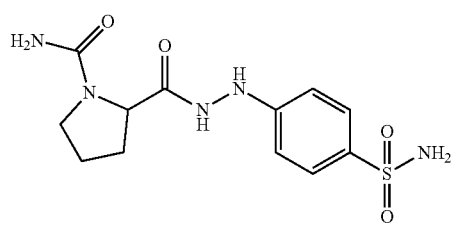 [SMILES: NC(=O)N1CCCC1C(=O)NNc1ccc(S(N)(=O)=O)cc1]

¹H NMR (400 MHz, DMSO-d₆) δ 9.77 (s, 1H), 8.29 (s, 1H), 7.51 (d, J=8.7 Hz, 2H), 6.99 (s, 2H), 6.80 (d, J=8.6 Hz, 2H), 5.88 (s, 2H), 4.23-4.20 (m, 1H), 3.41-3.36 (m, 1H), 3.26-3.20 (m, 1H), 2.09-2.02 (m, 1H), 1.94-1.80 (m, 3H)
LC-MS m/z (M−H): 326.1
Purity (HPLC): 98.2%

Example 13

(2S,4S)-4-fluoro-2-(2-(4-fluorophenyl)hydrazinecarbonyl)pyrrolidine-1-carboxamide

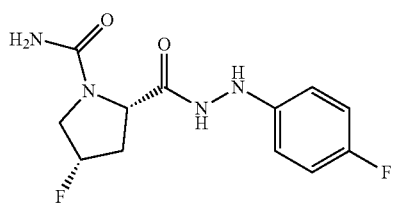 [SMILES: NC(=O)N1C[C@@H](F)C[C@H]1C(=O)NNc1ccc(F)cc1]

The title compound (30 mg) was prepared following an analogous procedure as in Example 2, but using (2S,4S)-1-carbamoyl-4-fluoropyrrolidine-2-carboxylic acid (Intermediate-7) (260 mg, 1.47 mmol) as starting material.

1H NMR (400 MHz, DMSO-d₆) δ 9.58 (s, 1H), 7.57 (s, 1H), 6.92-6.88 (m, 2H), 6.70-6.75 (m, 2H), 5.99 (s, 2H), 5.38-5.24 (m, 1H), 4.36 (d, J=9.6 Hz, 1H), 3.69-3.51 (m, 2H), 2.48-2.20 (m, 2H)

LC-MS m/z (M−H): 283.2

Purity (HPLC): 99.2%

Example 14

(R)-1-acetyl-N'-(4-fluorophenyl)pyrrolidine-2-carbohydrazide

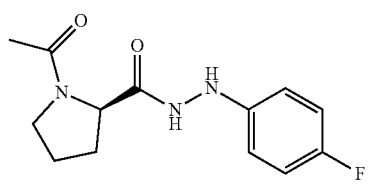 [SMILES: CC(=O)N1CCC[C@@H]1C(=O)NNc1ccc(F)cc1]

To a stirred solution of (R)-1-acetylpyrrolidine-2-carboxylic acid (50 mg, 0.31 mmol) in dry DMF (2 mL), DIPEA (82 mg, 0.63 mmol), HATU (181 mg, 0.47 mmol) and 4-fluorophenylhydrazine hydrochloride (65 mg, 0.37 mmol) were added at 0° C. and then the reaction mixture was stirred for 1 h at room temperature. The progress of the reaction was monitored by TLC. The reaction mixture was diluted with ice-cold water (10 mL), the solid formed was filtered and dried under vacuum to afford the title compound (30 mg, 35% yield) as off-white solid.

¹H NMR (400 MHz, CD₃OD) δ 6.95-6.84 (m, 4H), 4.45 (dd, J=3.8 Hz, J=8.6 Hz, 1H), 3.70-3.60 (m, 2H), 2.2-2.16 (m, 2H), 2.10 (s, 3H), 2.07-2.00 (m, 4H)

LC-MS m/z (M−H): 266.2

Purity (HPLC): 98.8%

Example 15

N'-(4-fluorophenyl)-1-hydroxypyrrolidine-2-carbohydrazide

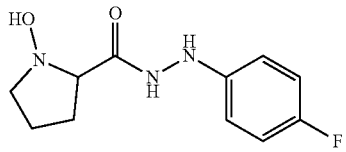 [SMILES: O=C(NNc1ccc(F)cc1)C1CCCN1O]

To a stirred solution of methyl 1-hydroxypyrrolidine-2-carboxylate (Intermediate-11) (250 mg, 1.373 mmol) in dry toluene (5 mL), 4-fluorophenylhydrazine hydrochloride (223 mg, 1.37 mmol), TEA (0.355 mL, 2.74 mmol) and trimethylaluminium (2 M in toluene, 0.69 mL, 1.37 mmol) were added at 0° C. and the reaction mixture was stirred at 70° C. for 1.5 h in microwave. The progress of the reaction was monitored by TLC. The reaction mixture was quenched with ice-cold water (20 mL); the aqueous layer was extracted with EtOAc (2×15 mL). The combined organic layer was washed with water (10 mL) and brine (10 mL), dried over anhydrous Na₂SO₄ and concentrated under reduced pressure. The crude compound was purified by column chromatography (silica gel, 100-200 mesh) to afford the title compound (30 mg, 7% yield) as off-white solid.

¹H NMR (400 MHz, DMSO-d₆) δ 9.4 (s, 1H), 8.15 (s, 1H), 7.65 (s, 1H), 6.95 (t, J=8.84 Hz, 2H), 6.7 (m, 2H), 3.3 (s, 1H), 3.15 (s, 1H), 2.7 (q, J=8.76 Hz, 1H), 2.1 (q, J=9.76 Hz, 1H), 1.81-1.65 (m, 3H)

LC-MS m/z (M+H): 240.2

Purity (HPLC): 98.8%

Example 16

N'-(4-fluorophenyl)-1,2-dimethylpyrrolidine-2-carbohydrazide

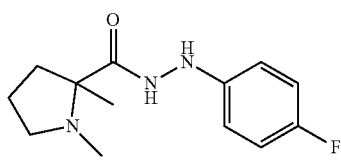 [SMILES: CN1CCCC1(C)C(=O)NNc1ccc(F)cc1]

Method A 1,2-Dimethylpyrrolidine-2-carboxylic acid (Intermediate-16) (200 mg, 1.40 mmol) was dissolved in 7 mL of dry DCM, and subsequently TEA (3 equiv.), EDC.HCl (1.5 equiv.) and DMAP (1.5 equiv.) were added. After 10 min stirring at 0° C., 4-fluorophenylhydrazine hydrochloride (1.5 equiv.) was added under argon atmosphere. After completion of the addition, the reaction mixture was stirred at room temperature overnight. The solvent was removed and the residue was dissolved with 5% MeOH in DCM (20 mL) and washed with water (2×10 mL). The collected organic phase was dried over anhydrous Na₂SO₄ and concentrated under reduced pressure to obtain the title compound, which was purified by column chromatography (DCM:MeOH=9.5:0.5) (42 mg, 12% yield).

¹H NMR (500 MHz, DMSO-d₆) δ 1.12 (s, 3H), 1.17-1.67 (m, 3H), 2.05 (s, 1H), 2.28 (s, 3H), 2.54-2.51 (m, 1H), 3.02 (d, J=1.5 Hz, 1H), 6.70-6.58 (m, 2H), 6.99-6.96 (m, 2H), 7.51 (d, J=2.9 Hz, 1H), 9.56 (d, J=2.8 Hz, 1H) ppm

LC-MS: 252.4 (M+H)

Purity (HPLC): 96.0%

Method B

The title compound was prepared by coupling N-Boc protected methyl 2-methylpyrrolidine-2-carboxylate (Intermediate-10) with 4-fluorophenylhydrazine, followed by deprotection and methylation of the N-atom of the pyrrolidine ring, according to the process depicted in Scheme VIII:

SCHEME VIII

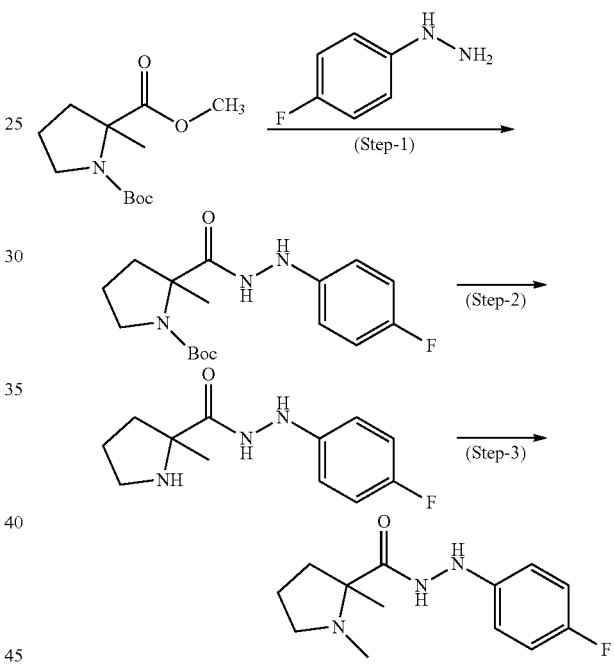

Step 1: Preparation of tert-butyl 2-(2-(4-fluorophenyl)hydrazinecarbonyl)-2-methylpyrrolidine-1-carboxylate To a stirred solution of 1-tert-butyl 2-methyl 2-methylpyrrolidine-1,2-dicarboxylate (Intermediate-10) (3 g, 12.34 mmol) in toluene (24 mL) 4-fluorophenylhydrazine hydrochloride (2.4 g, 14.81 mmol) was added, followed by TEA (3.1 g, 30.69 mmol) and trimethylaluminium (2 M in toluene, 2.65 g, 36.80 mmol) at room temperature and the reaction mixture was stirred at 60° C. in microwave for 1 h. The progress of the reaction was monitored by TLC. The reaction mixture was quenched with NH₄Cl solution and extracted with EtOAc (2×50 mL). The combined organic layer was washed with water (20 mL) and brine (20 mL), dried over anhydrous Na₂SO₄ and concentrated under reduced pressure. The crude compound was purified by column chromatography (silica gel 100-200 mesh) to afford the title compound (2.2 g, 53% yield) as off-white solid.

$^1$H NMR (400 MHz, CDCl$_3$) δ 9.13 (s, 1H), 6.94-6.92 (m, 2H), 6.81 (s, 2H), 6.00 (s, 1H), 3.51 (bs, 2H), 2.66 (s, 1H), 1.80 (s, 3H), 1.68 (s, 3H), 1.49 (s, 9H) LC-MS m/z (M−H): 336.2

Step 2: Preparation of N'-(4-fluorophenyl)-2-methylpyrrolidine-2-carbohydrazide To a stirred solution of tert-butyl 2-(2-(4-fluorophenyl)hydrazinecarbonyl)-2-methylpyrrolidine-1-carboxylate (2.2 g, 6.52 mmol) in DCM (4 mL), trifluoroacetic acid (4.4 mL) was added at 0° C. and the reaction mixture was stirred at room temperature for 4 h. The progress of the reaction was monitored by TLC. The reaction mixture was concentrated, the residue was co-distilled with DCM (3×10 mL). The crude compound was neutralized with saturated NaHCO$_3$ solution (3 mL) and extracted with 10% MeOH/chloroform (2×30 mL). The combined organic layer was washed with water (20 mL) and brine (20 mL), dried over anhydrous Na$_2$SO$_4$ and concentrated under reduced pressure to afford the title compound (1 g, 64% yield) as brown solid.

Step 3: Preparation of N'-(4-fluorophenyl)-1,2-dimethylpyrrolidine-2-carbohydrazide To a stirred solution of N'-(4-fluorophenyl)-2-methylpyrrolidine-2-carbohydrazide (1 g, 4.21 mmol) in acetonitrile (50 mL), K$_2$CO$_3$ (1.43 g, 10.51 mmol) was added, followed by iodomethane (0.313 mL, 5.07 mmol) at 0° C. and the reaction mixture was stirred at room temperature for 12 h. The progress of the reaction was monitored by TLC. The reaction mixture was quenched with water (30 mL) and extracted with EtOAc (2×20 mL). The combined organic layer was washed with water (10 mL) and brine (10 mL), dried over anhydrous Na$_2$SO$_4$ and concentrated under reduced pressure. The crude compound was purified by column chromatography (silica gel 100-200 mesh) to afford the title compound (350 mg, 33% yield) as brick red solid.

$^1$H NMR (400 MHz, CDCl$_3$) δ 9.14 (s, 1H), 6.95-6.920 (m, 2H), 6.79-6.76 (m, 2H), 5.97 (s, 1H), 3.19-3.08 (m, 1H), 2.59-2.53 (m, 1H), 2.37 (s, 3H), 2.20 (s, 1H), 1.85-1.77 (m, 3H), 1.23 (s, 3H)

LC-MS m/z (M+H): 252.2

Example 17

2-(2-(4-fluorophenyl)hydrazinecarbonyl)-N,N-dimethylpyrrolidine-1-carboxamide

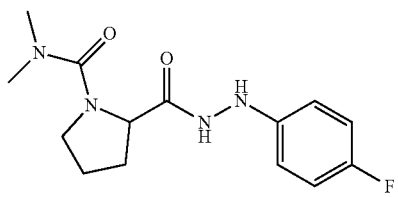 [SMILES: CN(C)C(=O)N1CCCC1C(=O)NNc1ccc(F)cc1]

The title compound was prepared following an analogous procedure as in Example 15, using methyl 1-(dimethylcarbamoyl)pyrrolidine-2-carboxylate (Intermediate-12) (100 mg, 0.49 mmol) as starting material. In this case, the reaction was carried out at 90° C. for 60 min, and the reaction mixture was quenched with NH$_4$Cl. The crude compound was purified by preparative TLC to afford the title compound (30 mg, 20% yield) as off-white solid.

$^1$H NMR (400 MHz, DMSO-d$_6$) δ 8.44 (d, J=3.9 Hz, 1H), 6.97-6.90 (m, 2H), 6.88-6.75 (m, 2H), 5.97 (d, J=4.3 Hz, 1H), 4.62 (t, J=7.9 Hz, 1H), 3.50-3.40 (m, 2H), 2.90 (s, 6H), 2.32-2.24 (m, 1H), 2.22-2.10 (m, 1H), 2.09-1.94 (m, 1H), 1.86-1.74 (m, 1H)

LC-MS m/z (M−H): 293.2

Purity (HPLC): 98.2%

Example 18

N'-(4-fluorophenyl)-1-(piperazine-1-carbonyl)pyrrolidine-2-carbohydrazide hydrochloride

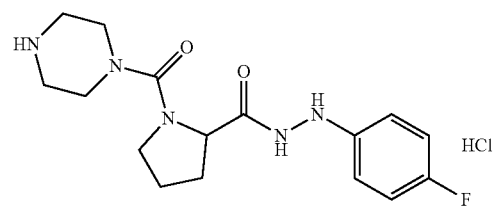 [SMILES: O=C(NNc1ccc(F)cc1)C1CCCN1C(=O)N1CCNCC1 ; Cl]

The title compound was prepared by coupling the corresponding pyrrolidine intermediate (Intermediate-13), which carries a Boc protecting group on the piperazine ring, with 4-fluorophenylhydrazine, and subsequent deprotection, according to the process depicted in Scheme IX:

SCHEME IX

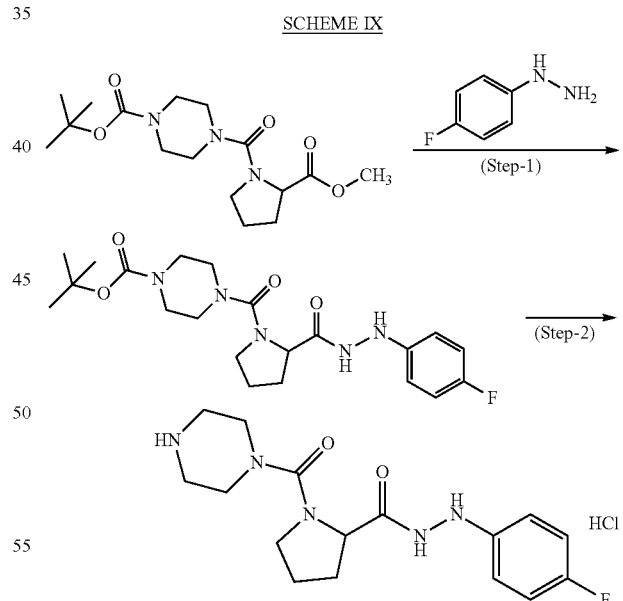

Step 1: Preparation of tert-butyl 4-(2-(2-(4-fluorophenyl)hydrazinecarbonyl)pyrrolidine-1-carbonyl)piperazine-1-carboxylate The coupling reaction was performed following an analogous procedure as disclosed in Example 2, using tert-butyl 4-(2-(methoxycarbonyl)pyrrolidine-1-carbonyl)piperazine- 1-carboxylate (Intermediate-13) (1 g, 2.92 mmol) as starting material, to afford the title compound (100 mg, 8% yield) as yellow solid.

Step 2: Preparation of N'-(4-fluorophenyl)-1-(piperazine-1-carbonyl)pyrrolidine-2-carbohydrazide hydrochloride For the deprotection, a mixture of tert-butyl 4-(2-(2-(4-fluorophenyl)hydrazinecarbonyl)pyrrolidine-1-carbonyl)piperazine-1-carboxylate (100 mg, 0.22 mmol) in dioxane.HCl (1 mL) was stirred at room temperature for 5 h. The progress of the reaction was monitored by TLC. The solvent was evaporated under reduced pressure. The crude compound was washed with diethyl ether (5 mL) to afford the title compound (30 mg, 36% yield) as pale yellow solid.

$^1$H NMR (400 MHz, DMSO-$d_6$) δ 9.68 (s, 1H), 8.91 (bs, 2H), 7.66 (s, 1H), 6.97-6.93 (m, 2H), 6.70-6.67 (m, 2H), 4.32 (t, J=8.8 Hz, 1H), 3.47-3.31 (m, 5H), 3.08-3.02 (m, 4H), 2.21 (s, 1H), 1.91 (s, 1H), 1.74-1.69 (m, 2H)

LC-MS m/z (M+H): 373.0

Purity (HPLC): 99.5%

Example 19

1-(4-acetylpiperazine-1-carbonyl)-N'-(4-fluorophenyl)pyrrolidine-2-carbohydrazide hydrochloride

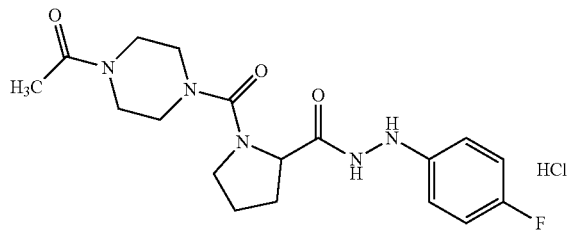 [SMILES: CC(=O)N1CCN(C(=O)N2CCCC2C(=O)NNc2ccc(F)cc2)CC1 ; Cl]

To a stirred solution of N'-(4-fluorophenyl)-1-(piperazine-1-carbonyl)pyrrolidine-2-carbohydrazide hydrochloride (Example 18) (200 mg, 0.53 mmol) in pyridine (2 mL) acetyl chloride (42 mg, 053 mmol) was added at 0° C. dropwise and the reaction mixture was stirred at room temperature for 2 h. The progress of the reaction was monitored by TLC. The reaction mixture was evaporated, the residue was quenched with ice cold-water (15 mL) and extracted with 10% MeOH/DCM (2×10 mL). The combined organic layer was washed with water (10 mL), brine (10 mL), dried over anhydrous $Na_2SO_4$ and concentrated under reduced pressure. The crude compound was dissolved in dioxane.HCl (10 mL) at room temperature and stirred for 10 min, the solvent was evaporated and washed with EtOAc (5 mL) to afford the title compound (50 mg, 22% yield) as white solid.

$^1$H NMR (400 MHz, DMSO-$d_6$) δ 9.63 (d, J=2.4 Hz, 1H), 7.64 (d, J=2.0 Hz, 1H), 6.93 (t, J=8.8 Hz, 2H), 6.70-6.66 (m, 2H), 4.33 (t, J=4.4 Hz, 1H), 3.46-3.44 (m, 3H), 3.39-3.35 (m, 3H), 3.29-3.20 (m, 1H), 3.19-3.14 (m, 3H), 2.18 (s, 1H), 1.97 (s, 3H), 1.91 (s, 1H), 1.74-1.61 (m, 2H)

LC-MS m/z (M+H): 415.1

Purity (HPLC): 99.8%

Example 20

N'-(4-fluorophenyl)-1-(morpholine-4-carbonyl)pyrrolidine-2-carbohydrazide hydrochloride

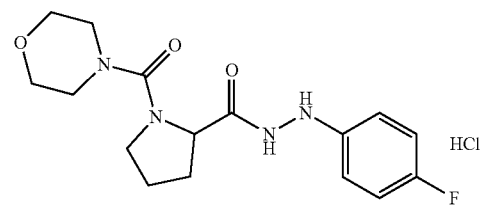 [SMILES: O=C(NNc1ccc(F)cc1)C1CCCN1C(=O)N1CCOCC1 ; Cl]

The title compound was prepared following an analogous procedure as in Example 15, using methyl 1-(morpholine-4-carbonyl)pyrrolidine-2-carboxylate (Intermediate-14) (1 g, 4.12 mmol) as starting material. The crude compound obtained was purified by column chromatography and the resulting compound was treated with dioxane hydrochloride for 15 min at room temperature and the solvent was evaporated to afford the title compound (30 mg) as off-white solid.

1H NMR (400 MHz, DMSO-$d_6$) δ 9.62 (d, J=2.5 Hz, 1H), 7.65 (d, J=2.5 Hz, 1H), 6.96-6.92 (m, 2H), 6.70-6.67 (m, 2H), 4.32 (t, J=7.9 Hz, 1H), 3.61-3.51 (m, 4H), 3.50-3.44 (m, 1H), 3.42-3.30 (m, 1H), 3.28-3.24 (m, 2H), 3.15-3.10 (m, 2H), 2.19-2.15 (m, 1H), 1.89 (s, 1H), 1.75-1.68 (m, 2H)

LC-MS m/z (M−H): 374.0

Purity (HPLC): 99.7%

Example 21

N'-(4-fluorophenyl)-1-methyl-5-oxopyrrolidine-2-carbohydrazide

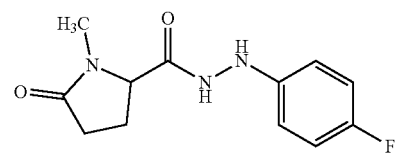 [SMILES: CN1C(=O)CCC1C(=O)NNc1ccc(F)cc1]

To a solution of ethyl 1-methyl-5-oxopyrrolidine-2-carboxylate (Intermediate-15) (500 mg in 5 mL of toluene), trimethylaluminium (3 equiv.) was added at ice cold condition and stirred under argon atmosphere for 15 min. Then 4-fluorophenylhydrazine hydrochloride (1 equiv.) in 2 mL of toluene was added to the reaction mixture and refluxed at 120° C. for 4 h. After the completion of the reaction, the reaction mixture was quenched with saturated $NH_4Cl$ solution and extracted with EtOAc (3×15 mL). The collected organic phase was dried over anhydrous $Na_2SO_4$ and concentrated under reduced pressure. The crude product was purified by column chromatography (DCM:MeOH=9.7:0.3) and recrystallized with DCM and diethyl ether to obtain the title compound (25 mg, 3.15% yield).

$^1$H NMR (500 MHz, DMSO-d$_6$) δ 2.01 (s, 1H), 2.21 (s, 2H), 2.37 (s, 1H), 2.69 (s, 3H), 5.08 (d, J=7.7 Hz, 1H), 5.41 (s, 2H), 7.22 (brs, 2H), 7.60 (brs, 2H) ppm

LC-MS (M+H): 252.2

Purity (HPLC): 95%

Example 22

N'-(4-fluorophenyl)-1-methylpyrrolidine-2-carbohydrazide

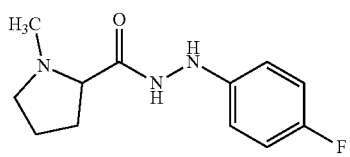 [SMILES: CN1CCCC1C(=O)NNc1ccc(F)cc1]

The title compound was prepared using an analogous procedure as disclosed for Example 16 (method A), employing 1-methylpyrrolidine-2-carboxylic acid (400 mg) as starting product. The crude product obtained in the reaction was purified by column chromatography (DCM:MeOH=9.5:0.5) to afford 27 mg of the title compound (3.7% yield).

$^1$H NMR (500 MHz, DMSO-d$_6$) δ 1.79-1.73 (m, 3H), 2.09 (s, 1H), 2.27-2.25 (m, 1H), 2.34 (s, 3H), 2.86-2.83 (m, 1H), 3.03 (s, 1H), 6.71-6.67 (m, 2H), 7.00-6.96 (m, 2H), 7.62 (s, 1H), 9.61 (s, 1H) ppm

LC-MS (M+H): 238.8

Purity (HPLC): 95.0%

Example 23

4-amino-N'-(4-fluorophenyl)-1-methylpyrrolidine-2-carbohydrazide

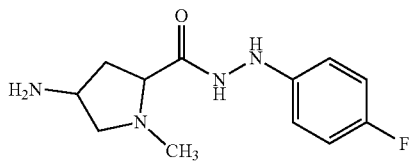

The title compound was obtained by coupling 4-fluorophenylhydrazine with 4-amino-1-methylpyrrolidine-2-carboxylic acid, previously protecting the amine of the latter with a Boc protecting group, and deprotecting it after the coupling reaction, as depicted in Scheme X:

SCHEME X

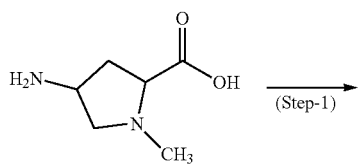

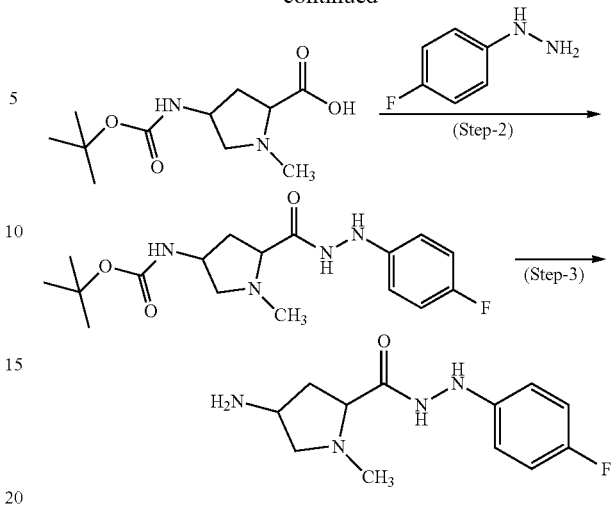

Step 1: Preparation of 4-((tert-butoxycarbonyl)amino)-1-methylpyrrolidine-2-carboxylic acid To solution of 4-amino-1-methylpyrrolidine-2-carboxylic acid (1 equiv.) in 60 mL dioxane:H$_2$O (2:3), Na$_2$CO$_3$ (3 equiv.) was added and stirred for 10 min at 0° C. Then, to this reaction mixture Boc anhydride (1.1 equiv.) was added dropwise at the same temperature and allowed for stirring at room temperature overnight. After completion of the reaction, the reaction mixture was acidified with 1 N HCl to bring the pH at 3 and it was extracted with 10% MeOH in DCM (60 mL). The organic layer was dried over anhydride Na$_2$SO$_4$. The organic solvent was distilled out at reduced pressure to obtain the crude title compound which was purified by column chromatography (DCM:MeOH=9.6:0.4) to afford the purified title compound (9.8% yield).

LC-MS (M+H): 245.3

Step 2: Preparation of tert-butyl (5-(2-(4-fluorophenyl)hydrazinecarbonyl)-1-methylpyrrolidin-3-yl)carbamate The title compound was prepared using an analogous procedure as disclosed for Example 16 (method A), employing 4-((tert-butoxycarbonyl)amino)-1-methylpyrrolidine-2-carboxylic acid (100 mg) as starting product. The crude product obtained in the reaction was purified by column chromatography (DCM:MeOH=9.5:0.5) to afford 50 mg of the title compound (34.71% yield).

LC-MS (M+H): 353.4

Purity (HPLC): 92.14%

Step 3: Preparation of 4-amino-N'-(4-fluorophenyl)-1-methylpyrrolidine-2-carbohydrazide For deprotection, 5 mL of 5 N HCL was added dropwise at 0° C. to a solution of tert-butyl (5-(2-(4-fluorophenyl)hydrazinecarbonyl)-1-methylpyrrolidin-3-yl)carbamate (1 equiv.) in 5 mL DCM, and the mixture was allowed to stirring for 4 h. After complete consumption of starting material, the solvent was distilled out under reduced pressure to obtain a sticky solid which was dissolved in 10% MeOH in DCM and washed with saturated solution of NaHCO$_3$. The organic portion was collected and dried over Na$_2$SO$_4$, the organic portion was distilled out under reduced pressure to obtain the title compound (25 mg, 69.4%).

$^1$H NMR (500 MHz, DMSO-d$_6$) δ 1.65-1.4 (m, 1H), 2.37 (s, 3H), 2.1-2.41 (m, 3H), 2.77 (d, J=9.05 Hz, 1H), 2.82 (t, J=6.35 Hz, 1H), 6.74-6.71 (m, 2H), 6.99-6.96 (m, 2H), 7.62 (s, 1H), 9.75 (brs, 1H) ppm; The NH$_2$ protons remain unsolved.

LC-MS (M+H): 253.4

Purity (HPLC): 95.0%

Example 24

4-fluoro-N'-(4-fluorophenyl)-1-methylpyrrolidine-2-carbohydrazide

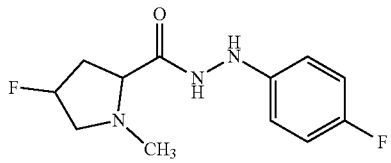 [SMILES: CN1CC(F)CC1C(=O)NNc1ccc(F)cc1]

The title compound was prepared using an analogous procedure as disclosed for Example 21, employing 4-fluoro-1-methylpyrrolidine-2-carboxylic acid acid (Intermediate-17) as starting material. 90 mg of 4-fluoro-1-methylpyrrolidine-2-carboxylic acid afforded the title compound as crude product. The crude product was purified by column chromatography using DCM as eluent to afford 20 mg of the title compound (13% yield).

1H NMR (500 MHz, DMSO-d6) δ 2.35-2.25 (m, 1H), 2.57 (s, 3H), 2.64-2.62 (m, 1H), 3.21 (d, J=7.5 Hz, 1H), 3.47-3.45 (m, 1H), 5.22 (m, 1H), 5.97 (d, J=3.5 Hz, 1H), 6.82-6.80 (m, 2H), 6.95-6.91 (m, 2H), 8.94 (s, 1H) ppm

LC-MS (M+H): 256.4

Purity (HPLC): 95.0%

Example 25

(S)-1-(cyclopropylmethyl)-N'-(4-fluorophenyl)pyrrolidine-2-carbohydrazide

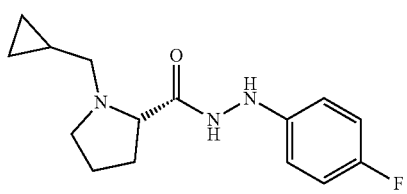

The title compound was prepared using an analogous procedure as disclosed for Example 16 (method A), employing (R)-1-(cyclopropylmethyl)pyrrolidine-2-carboxylic acid (120 mg) as starting material. The crude product was purified by column chromatography using DCM as eluent to afford 30 mg of the title compound (12.2% yield).

$^1$H NMR (500 MHz, DMSO-d$_6$) δ 0.11 (s, 1H), 0.49-0.44 (m, 2H), 0.9-1.1 (m, 1H), 1.78-1.76 (m, 3H), 1.99-2.05 (m, 1H), 2.42-2.28 (m, 2H), 3.05 (s, 1H), 3.31 (s, 1H), 6.71-6.67 (m, 2H), 6.99-6.96 (m, 2H), 7.60 (s, 1H), 9.51 (s, 1H) ppm;

LC-MS (M+H): 278.2

Purity (HPLC): 96.2%

Example 26

N'-(4-fluorophenyl)-3-methyl-3-azabicyclo[3.1.0]hexane-2-carbohydrazide

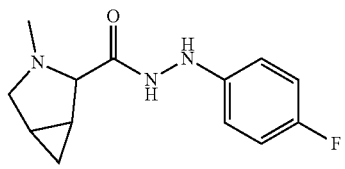 [SMILES: CN1CC2CC2C1C(=O)NNc1ccc(F)cc1]

The title compound was prepared using an analogous procedure as disclosed for Example 16 (method A), employing 3-methyl-3-azabicyclo[3.1.0]hexane-2-carboxylic acid (Intermediate-18) (25 mg, 0.18 mmol) as starting material, which afforded 3 mg of the final product (7% yield).

$^1$H NMR (500 MHz, CDCl$_3$) δ 0.52 (d, J=5.4 Hz, 1H), 0.78 (s, 1H), 1.16 (d, J=4.0 Hz, 1H), 1.43 (t, J=6.5 Hz, 1H), 2.73 (s, 3H), 2.59 (d, J=6.4 Hz, 1H), 3.23-3.16 (m, 2H), 6.01 (s, 1H), 6.83-6.80 (m, 2H), 6.95-6.92 (m, 2H), 8.38 (s, 1H) ppm

LC-MS (M+H): 250.2

Purity (HPLC): 98.2%

Example 27

N'-(4-fluorophenyl)-1,4-dimethylpyrrolidine-2-carbohydrazide

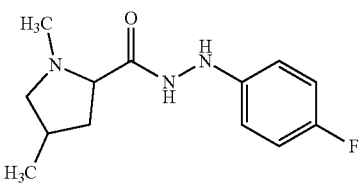 [SMILES: CC1CC(C(=O)NNc2ccc(F)cc2)N(C)C1]

The title compound was prepared using an analogous procedure as disclosed for Example 16 (method A), employing 1,4-dimethylpyrrolidine-2-carboxylic acid (Intermediate-19) (100 mg, 0.70 mmol) as starting material, which afforded 14 mg of the final product (9% yield).

$^1$H NMR (500 MHz, CDCl$_3$) δ 1.13 (s, 3H), 1.63 (brs, 3H), 2.42 (s, 1H), 2.82 (s, 3H), 2.97 (s, 1H), 6.27 (s, 1H), 6.83-6.80 (m, 2H), 6.93-6.89 (m, 2H) ppm, one NH-proton remained unsolved

LC-MS (M+H): 252.4

Purity (HPLC): 95.1%

Example 28

N'-(4-fluorophenyl)-1,3-dimethylpyrrolidine-2-carbohydrazide

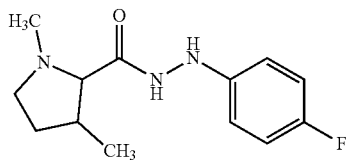

The title compound was prepared using an analogous procedure as disclosed for Example 16 (method A), employing 1,3-dimethylpyrrolidine-2-carboxylic acid (Intermediate-20) (200 mg, 1.4 mmol) as starting material, which afforded 48 mg of crude product which was purified by column chromatography using 2% MeOH in DCM as eluent to afford 29 mg of the title compound (8% yield).

$^1$H NMR (500 MHz, DMSO-$d_6$) δ 1.06 (s, 3H), 1.38 (s, 1H), 2.06-2.03 (m, 1H), 2.20 (s, 1H), 2.30 (s, 3H), 2.35-2.31 (m, 1H), 3.04 (t, J=3.8 Hz, 1H), 6.71-6.58 (m, 2H), 7.00-6.96 (m, 2H), 7.63 (s, 1H), 9.63 (s, 1H) ppm;

LC-MS (M+H): 252.4

Purity (HPLC): 96.78%

Example 29

1-ethyl-N'-(4-fluorophenyl)pyrrolidine-2-carbohydrazide

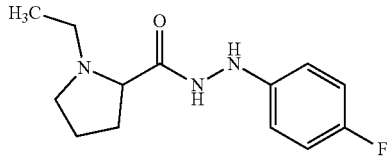 [SMILES: CCN1CCCC1C(=O)NNc1ccc(F)cc1]

The title compound was prepared using an analogous procedure as disclosed for Example 16 (method A), employing 1-ethylpyrrolidine-2-carboxylic acid (Intermediate-21) (100 mg, 0.70 mmol) as starting material, which afforded 30 mg of crude product which was purified by column chromatography using 9.5:0.5 (v/v) MeOH:DCM as eluent to yield 30 mg of the title compound (17% yield).

$^1$H NMR (500 MHz, CDCl$_3$) δ 1.17 (t, J=7.2 Hz, 3H), 1.88-1.85 (m, 2H), 1.96 (d, J=4.0 Hz, 1H), 2.22-2.20 (m, 1H), 2.45 (brs, 1H), 2.62 (s, 1H), 2.78 (t, J=7.3 Hz, 1H), 3.24 (d, J=6.5 Hz, 1H), 3.31 (s, 1H), 6.11 (s, 1H), 6.79-6.69 (m, 2H), 6.95-6.90 (m, 2H), 9.21 (brs, 1H) ppm

LC-MS (M+H): 252.5

Purity (HPLC): 96.45%

Example 30

2-(2-(4-fluorophenyl)hydrazinecarbonyl)pyrrolidine-1-carboximidamide hydrochloride

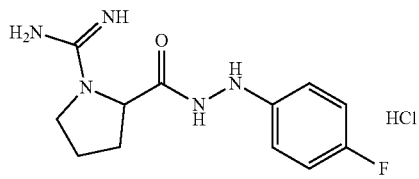 [SMILES: N=C(N)N1CCCC1C(=O)NNc1ccc(F)cc1 ; Cl]

The title compound was prepared according to the general method B (Scheme II) by coupling N-Cbz protected pyrrolidine-2-carboxylic acid (Intermediate-22) with N-Boc protected 4-fluorophenylhydrazine, followed by deprotection of the N-atom of the pyrrolidine, introduction of the amidine group, and removal of the remaining protecting groups, according to the process depicted in Scheme XI:

SCHEME XI

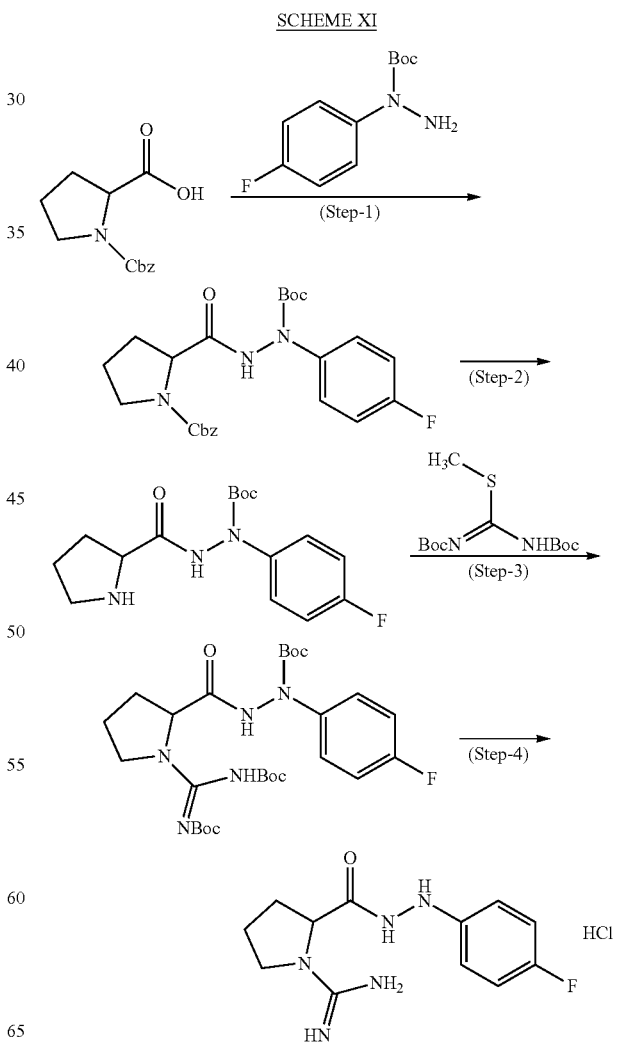

Step 1: Preparation of benzyl 2-(2-(tert-butoxycarbonyl)-2-(4-fluorophenyl)hydrazinecarbonyl)pyrrolidine-1-carboxylate To a stirred solution of 1-(benzyloxycarbonyl)pyrrolidine-2-carboxylic acid (Intermediate-22) (1 g, 4.01 mmol) in DMF (15 mL) DIPEA (1.55 g, 12.01 mmol), HATU (1.9 g, 5.0 mmol) and tert-butyl 1-(4-fluorophenyl)hydrazinecarboxylate (1.15 g, 4.38 mmol) were added at 0° C. and the reaction mixture was stirred at room temperature for 2 h. The progress of the reaction was monitored by TLC. The reaction mixture was poured into ice-cold water (25 mL) and extracted with EtOAc (2×25 mL). The combined organic layer was washed with water (15 mL) and brine (15 mL), dried over anhydrous $Na_2SO_4$ and concentrated under reduced pressure. The crude compound was purified by column chromatography (silica gel, 100-200 mesh) to afford the title compound (500 mg, 27% yield) as pale yellow semi-solid.

Step 2: Preparation of tert-butyl 1-(4-fluorophenyl)-2-(pyrrolidine-2-carbonyl)hydrazinecarboxylate To a stirred solution of 2-(2-(tert-butoxycarbonyl)-2-(4-fluorophenyl)hydrazinecarbonyl)pyrrolidine-1-carboxylate (500 mg, 1.09 mmol) in MeOH (10 mL) Pd/C (10% wet, 100 mg 20% wt/wt) was added and the reaction mixture was stirred under hydrogen atmosphere at room temperature for 16 h. The progress of the reaction was monitored by TLC. The reaction mixture was filtered through a pad of celite; and the filtrate was evaporated under reduced pressure. The crude compound was purified by column chromatography (silica gel, 100-200 mesh) to afford the title compound (200 mg, 28% yield) as off white solid.

$^1H$ NMR (400 MHz, DMSO-$d_6$) δ 10.42 (s, 1H), 7.34 (q, J=3.8 Hz, 2H), 7.16-7.11 (m, 2H), 3.62 (q, J=3.1 Hz, 1H), 2.83 (t, J=6.5 Hz, 2H), 1.98-1.94 (m, 1H), 1.76-1.70 (m, 2H), 1.67-1.57 (m, 2H), 1.38 (s, 9H)

LC-MS m/z (M+H): 324.11

Step 3: Preparation of tert-butyl 2-(1-(N,N'-bis(tert-butoxycarbonyl)carbamimidoyl)pyrrolidine-2-carbonyl)-1-(4-fluorophenyl)hydrazinecarboxylate To a stirred solution of tert-butyl 1-(4-fluorophenyl)-2-(pyrrolidine-2-carbonyl) hydrazinecarboxylate (300 mg, 0.928 mmol) in DMF (3 mL) 1,3-bis(tert-butoxycarbonyl)-2-methyl-2-thiopseudourea (294 mg, 1.01 mmol), TEA (234 mg, 2.314 mmol), and $HgCl_2$ (251 mg, 0.926 mmol) were added at 0° C. and the reaction mixture was stirred at room temperature for 4 h. The progress of the reaction was monitored by TLC. The reaction mixture was poured into water (20 mL), extracted with EtOAc (2×10 mL). The combined organic layer was washed with water (5 mL) and brine (5 mL), dried over anhydrous $Na_2SO_4$ and concentrated under reduced pressure. The crude compound was purified by column chromatography (silica gel, 60-120 mesh) to afford the title compound (200 mg, 38% yield) as white solid.

LC-MS (M+H): 566.3

Step 4: Preparation of 2-(2-(4-fluorophenyl)hydrazinecarbonyl)pyrrolidine-1-carboximidamide hydrochloride A solution of tert-butyl 2-(1-(N,N'-bis(tert-butoxycarbonyl)carbamimidoyl) pyrrolidine-2-carbonyl)-1-(4-fluorophenyl)hydrazinecarboxylate (200 mg, 0.35 mmol) in 1,4-dioxane.HCl (4 mL) was stirred at room temperature for 2 h. The progress of the reaction was monitored by TLC. The reaction mixture was concentrated under reduced pressure; the residue was co-distilled with DCM to afford the title compound (25 mg, 26% yield) as pale yellow liquid.

$^1H$ NMR (400 MHz, DMSO-$d_6$) δ 9.92 (s, 1H), 7.32 (s, 4H), 6.96 (t, J=8.8 Hz, 2H), 6.73 (q, J=4.2 Hz, 2H), 4.62 (d, J=6.2 Hz, 1H), 3.69-3.61 (m, 2H), 3.54-3.50 (m, 2H), 3.42 (q, J=7 Hz, 2H)

LC-MS m/z (M+H): 301.75

Purity (HPLC): 94.0%

Example 31

Antimicrobial Activity

The products of the present invention were tested for their activity against *Acinetobacter baumannii* (*A. baumannii*) as well as against the following bacteria: *Staphylococcus aureus* (*S. aureus*), *Streptococcus pneumoniae* (*S. pneumoniae*), *Enterococcus faecium* (*E. faecium*), *Pseudomonas aeruginosa* (*P. aeruginosa*), *Klebsiella pneumoniae* (*K. pneumoniae*) and *Escherichia coli* (*E. coli*).

Minimal inhibitory concentrations (MICs) were determined using a standard microtiter dilution method, according to the Clinical and Laboratory Standards Institute (CLSI) procedures, in particular according to M07-A9: "*Methods for Dilution Antimicrobial Susceptibility Tests for Bacteria That Grow Aerobically; Approved Standard—Ninth Edition*".

Briefly, compounds were dissolved with dimethyl sulfoxide (DMSO) at 12.8 mg/mL. Serial two-fold dilutions of compounds were performed in DMSO and 1 μl of each dilution were transferred into microtiter culture plates, followed by 100 μl of inoculated culture media to give a final microorganism concentration of $5×10^5$ colony-forming units/mL. Plates were incubated at 37° C. for 24 hours and MICs determined as the lowest compound concentration that inhibited growth. Media used in determinations were Cation adjusted Mueller-Hinton Broth for all the microorganisms except for *S. pneumoniae* and *E. faecium* whose culture media were supplemented with 2.5% of lysed horse blood. Incubations were performed at air atmosphere except *S. pneumoniae* cultures that were incubated with 5% $CO_2$ atmosphere.

The MIC values found (in μg/mL) for the tested compounds are given in Table 1 below.

TABLE 1

| Ex. | A. baumannii | S. aureus | S. pneumoniae | E. faecium | P. aeruginosa | K. pneumoniae | E. coli |
|---|---|---|---|---|---|---|---|
| 2 | 4 | >128 | >128 | >128 | >128 | >128 | >128 |
| 3 | 4 | >128 | >128 | >128 | >128 | >128 | >128 |
| 4 | 2 | >128 | >128 | >128 | >128 | >128 | >128 |
| 7 | 8 | 128 | >128 | >128 | >128 | >128 | >128 |
| 9 | 8 | >128 | >128 | >128 | >128 | >128 | >128 |

TABLE 1-continued

| Ex. | A. baumannii | S. aureus | S. pneumoniae | E. faecium | P. aeruginosa | K. pneumoniae | E. coli |
|---|---|---|---|---|---|---|---|
| 10 | 2 | >128 | >128 | >128 | >128 | >128 | >128 |
| 11 | 8 | >128 | >128 | >128 | >128 | >128 | >128 |
| 14 | 2 | >128 | >128 | >128 | >128 | >128 | >128 |
| 15 | 1 | >128 | >128 | >128 | >128 | >128 | >128 |
| 16 | 0.25 | >128 | >128 | >128 | >128 | >128 | >128 |
| 18 | 8 | 128 | >128 | >128 | >128 | >128 | >128 |
| 25 | 0.25 | >128 | >128 | >128 | >128 | >128 | >128 |
| 26 | 0.25 | >128 | >128 | >128 | >128 | >128 | >128 |
| 30 | 2 | >128 | >128 | >128 | >128 | >128 | >128 |

As shown in Table 1, compounds of formula (I) according to the present invention are highly effective antibacterials against A. baumannii. Particularly, the MIC values obtained in the assay were of 8 µg/mL or lower for the tested compounds. Surprisingly, all the compounds showed a great selectivity for A. baumannii, since they were virtually inactive against the other bacteria tested.

Example 32

In Vitro Stability Assay in Mouse Plasma

Several compounds of the present invention were tested for their stability in mouse plasma, by LC-MS/MS detection. The concentration of the tested compounds in the assay was 1 µM and the % remaining of each tested compound was calculated at the following time points: 0, 15, 30 and 60 minutes.

The frozen mouse plasma was thawed at room temperature and centrifuged at 1400×RCF, at 4° C., for 15 minutes. Approximately 90% of the clear supernatant fraction was transferred to a separate tube and was used for the assay.

1 mM stock of test compound was prepared in acetonitrile:water by diluting from 10 mM stock (i.e. 10 µL of 10 mM stock solution was added to 90 µL of acetonitrile: water (50:50)). 25 µM stock of test compound was prepared in acetonitrile: water by diluting from 1 mM stock (i.e. 2.5 µL of 1 mM stock solution was added to 97.5 µL of acetonitrile: water (50:50)).

For 0 min samples, plasma was heat inactivated at 56° C. To 72 µL of heat inactivated plasma 3 µL of 25 µM test compound was added. A 50 µL aliquot of the mixture was taken and crashed with 200 µL of acetonitrile containing internal standard and was further processed along with other time points.

Final working stock of 1 µM was prepared by diluting in plasma ((i.e. 10 µL of 25 µM acetonitrile:water stock was added to 240 µL of plasma). 250 µL of plasma containing the test compound was incubated for 60 min at 37° C. in shaker water bath with gentle shaking. 50 µL aliquot of sample at 15, 30 and 60 min was precipitated immediately with 200 µL of acetonitrile containing internal standard and centrifuged at 4000×RCF, 4° C. for 20 minutes. 150 µL of supernatant was diluted with 150 µL of water and analyzed by LC-MS/MS.

The percent remaining of the test substance was calculated as ratio of peak area at each time point to peak area ratio at zero min, multiplied by 100.

The LC/MS/MS method used is defined by the following parameters: API4000 (MS), Shimadzu Prominance (LC), 20 µL injection volume; Column: Waters Xbridge, C18, 50*4.6 mm, 3.5 µm; eluent A: 0.1% formic acid in water, eluent B: acetonitrile; gradient: 0-0.80 min 95% A, 5% B; 0.08-1.6 min 5% A, 95% B; 1.6-2.5 min 95% A, 5% B; flow rate: 1 mL ml/min.

The compounds of formula (I) were found highly stable in this assay, with percentages remaining in the mouse plasma after 1 hour of 80% or superior, in most cases of more than 90%.

This data is highly relevant for the use of the compounds of the present invention as drugs, since a long stability in plasma is desirable to obtain good pharmacokinetic exposure of the drug and to maintain the activity in-vivo and is therefore significant in order to achieve a good therapeutic antibacterial efficacy.

The invention claimed is:
1. A compound of formula (I):

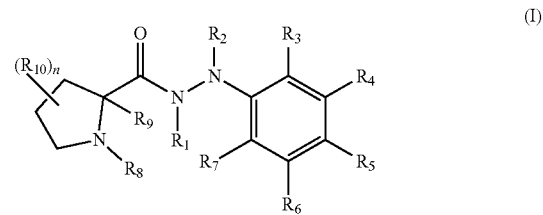

or a pharmaceutically acceptable salt or solvate thereof, wherein $R_1$ and $R_2$ are independently selected from hydrogen, $C_{1-4}$alkyl, halo$C_{1-4}$alkyl and hydroxy$C_{1-4}$alkyl;

$R_3$, $R_4$, $R_5$, $R_6$ and $R_7$ are independently selected from hydrogen, —OH, halogen, $C_{1-6}$alkoxy, halo$C_{1-4}$alkoxy, —O$C_{3-6}$cycloalkyl$C_{0-4}$alkyl, $C_{1-6}$alkyl, $C_{3-6}$cycloalkyl$C_{0-4}$alkyl, halo$C_{1-6}$alkyl, hydroxy$C_{1-6}$alkyl, $C_{1-4}$alkoxy$C_{1-6}$alkyl, $C_{1-4}$alkoxy$C_{1-4}$alkoxy, —OCOR$_{11}$, —OS(O$_2$)R$_{11}$, —NR$_{11}$R$_{12}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CONR$_{11}$R$_{12}$, —S(O$_2$)NR$_{11}$R$_{12}$, —S(O$_2$)R$_{11}$, —CN and —CO$_2$R$_{11}$; or two of $R_3$ to $R_7$ attached to adjacent carbon atoms are connected to form a 5- or 6-membered cycloalkyl, wherein 1 or 2 methylene groups of the cycloalkyl are optionally replaced by O, said cycloalkyl can be optionally substituted by one or more $C_{1-4}$alkyl or halo$C_{1-4}$alkyl;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, —C(O)$C_{1-4}$alkyl, —C(O)$C_{3-6}$cycloalkyl$C_{0-2}$alkyl, —CONR$_{13}$R$_{14}$, —C(NR$_{15}$)NR$_{11}$R$_{12}$ and —CO$_2$R$_{11}$;

$R_9$ is selected from hydrogen, $C_{1-4}$alkyl and halo$C_{1-4}$alkyl;

n is 0, 1, 2 or 3;

each $R_{10}$, if present, is independently selected from —OH, halogen, $C_{1-6}$alkyl, halo$C_{1-6}$alkyl, $C_{1-6}$alkoxy, $C_{1-4}$alkoxy$C_{1-6}$alkyl, —O$C_{3-6}$cycloalkyl$C_{0-4}$alkyl, —SR$_{11}$, —NR$_{11}$R$_{12}$, —OCOR$_{11}$, —OS(O$_2$)R$_{11}$, —NR$_{11}$COR$_{12}$, —$NR_{11}CO_2R_{12}$, —$NR_{11}S(O_2)R_{12}$, —$OCONR_{11}R_{12}$, —CN, phenyl, 5- or 6-membered heteroaryl ring comprising 1 or 2 heteroatoms selected from N, O and S; wherein said phenyl and said heteroaryl rings are optionally substituted by one or more $C_{1-4}$alkyl or halo$C_{1-4}$alkyl; or two $R_{10}$ attached to a common carbon atom form an oxo; or two $R_{10}$ attached to a common carbon atom form a spiro $C_{3-6}$cycloalkyl, or two $R_{10}$ attached to adjacent carbon atoms are connected to form a 3- to 6-membered cycloalkyl, said cycloalkyl is optionally substituted by one or more substituents independently selected from $C_{1-4}$alkyl, halo$C_{1-4}$alkoxy, halo$C_{1-4}$alkyl and halogen;

each $R_{11}$ and $R_{12}$ are independently selected from hydrogen, $C_{1-4}$alkyl, halo$C_{1-4}$alkyl and $C_{3-6}$cycloalkyl$C_{0-4}$alkyl;

each $R_{13}$ and $R_{14}$ are independently selected from hydrogen, $C_{1-4}$alkyl, $C_{3-6}$cycloalkyl$C_{0-4}$alkyl and Het$_{3-6}$, wherein each $C_{1-4}$alkyl and $C_{3-6}$cycloalkyl$C_{0-4}$alkyl are optionally substituted by one or more $R_{16}$, and wherein each $C_{1-4}$alkyl are optionally substituted by one or more Het$_{3-6}$; or $R_{13}$ and $R_{14}$ form, together with the N atom to which they are attached, a 4- to 6-membered saturated heterocycle, which optionally contain one additional heteroatom selected from N, S and O, said heterocycle can be optionally substituted by one or more substituents independently selected from $C_{1-4}$alkyl, halo$C_{1-4}$alkyl and —$C(O)C_{1-4}$alkyl;

$R_{15}$ is selected from hydrogen, $C_{1-6}$alkyl, halo$C_{1-6}$alkyl, —CN, —$CONR_{11}R_{12}$, —$S(O_2)R_{11}$, —$SOR_{11}$ and —$S(O_2)NR_{11}R_{12}$;

each $R_{16}$ is independently selected from alkyl, halogen, —CN, —$CO_2R_{11}$, —$OR_{11}$, —$SR_{11}$, —$NR_{17}R_{18}$, —$CONR_{17}R_{18}$ and —$OCOR_{11}$;

Het$_{3-6}$ is a 3- to 6-membered saturated monocyclic heterocyclic ring containing one heteroatom selected from O, S and N, wherein said ring is bonded to the rest of the molecule through any available C atom and wherein said ring is optionally substituted by one or more substituents independently selected from $C_{1-4}$alkyl and halo$C_{1-4}$alkyl; and each $R_{17}$ and $R_{18}$ are independently selected from hydrogen, $C_{1-4}$alkyl and halo$C_{1-4}$alkyl, or $R_{17}$ and $R_{18}$ form, together with the N atom to which they are attached, a 4-to 6-membered saturated heterocycle, which can optionally contain one additional heteroatom selected from N, S and O, said heterocycle can be optionally substituted by one or more substituents independently selected from $C_{1-4}$alkyl and halo$C_{1-4}$alkyl;

and wherein the following are excluded:
tert-butyl (S)-2-(2-phenylhydrazine-1-carbonyl)pyrrolidine-1-carboxylate,
tert-butyl (R)-2-(1-methyl-2-phenylhydrazine-1-carbonyl)pyrrolidine-1-carboxylate,
tert-butyl (2S,4S)-4-mercapto-2-(2-(3-sulfamoylphenyl)hydrazine-1-carbonyl) pyrrolidine-1-carboxylate,
3-(2-((2S,4S)-1-(tert-butoxycarbonyl)-4-mercaptopyrrolidine-2-carbonyl)hydrazinyl) benzoic acid,
tert-butyl (2S,4S)-4-mercapto-2-(2-(2-(trifluoromethyl)phenyl)hydrazine-1-carbonyl) pyrrolidine-1-carboxylate, and
tert-butyl (2S,4S)-2-(2-(2-chloro-5-(trifluoromethyl)phenyl)hydrazine-1-carbonyl)-4-mercaptopyrrolidine-1-carboxylate.

2. The compound according to claim 1, wherein
$R_1$ and $R_2$ are independently selected from hydrogen and $C_{1-4}$alkyl;
$R_3$, $R_4$, $R_5$, $R_6$ and $R_7$ are independently selected from hydrogen, —OH, halogen, $C_{1-6}$alkyl, $C_{3-6}$cycloalkyl$C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$, and halo$C_{1-4}$alkoxy, or two of $R_3$ to $R_7$ attached to adjacent carbon atoms are connected to form a 5- or 6-membered cycloalkyl, wherein 1 or 2 methylene groups of the cycloalkyl are optionally replaced by O, said cycloalkyl is optionally substituted by one or more $C_{1-4}$alkyl;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, —$C(O)C_{1-4}$alkyl, —$C(O)C_{3-6}$cycloalkyl$C_{0-2}$alkyl, —$CONR_{13}R_{14}$ and —$C(NR_{15})NR_{11}R_{12}$;

$R_9$ is selected from hydrogen and $C_{1-4}$alkyl;

n is 0, 1, 2 or 3;

each $R_{10}$, if present, is independently selected from —OH, halogen, $C_{1-6}$alkyl, $C_{1-4}$alkoxy$C_{0-6}$alkyl, —$SR_{11}$ and —$NR_{11}R_{12}$; or two $R_{10}$ attached to a common carbon atom form an oxo; or two $R_{10}$ attached to adjacent carbon atoms are connected to form a 3-to 6-membered cycloalkyl, said cycloalkyl is optionally substituted by one or more substituents independently selected from $C_{1-4}$alkyl and halogen;

each $R_{11}$ and $R_{12}$ are independently selected from hydrogen and $C_{1-4}$alkyl;

each $R_{13}$ and $R_{14}$ are independently selected from hydrogen and $C_{1-4}$alkyl, or $R_{13}$ and $R_{14}$ form, together with the N atom to which they are attached, a 4- to 6-membered saturated heterocycle, which can optionally contain one additional heteroatom selected from N, S and O, said heterocycle is optionally substituted by one or more substituents independently selected from $C_{1-4}$alkyl and —$C(O)C_{1-4}$alkyl; and $R_{15}$ is selected from hydrogen, $C_{1-6}$alkyl, halo$C_{1-6}$alkyl, —CN, —$CONR_{11}R_{12}$, —$SO_2$—$R_{11}$, —SO—$R_{11}$ and —$SO_2$—$NR_{11}R_{12}$.

3. The compound according to claim 1, wherein at least one of $R_3$ to $R_7$ is not hydrogen and at least two of $R_3$ to $R_7$ are hydrogen.

4. The compound according to claim 1, wherein $R_3$, $R_4$, $R_5$, $R_6$ and $R_7$ are independently selected from hydrogen, —OH, halogen, $C_{1-6}$ alkyl, halo$C_{1-6}$ alkyl, $C_{1-4}$alkoxy$C_{0-6}$alkyl, $C_{1-4}$alkoxy$C_{1-4}$alkoxy, —$SO_2$—$NR_{11}R_{12}$ and halo$C_{1-4}$alkoxy.

5. The compound according to claim 4, wherein $R_3$, $R_4$, $R_5$, $R_6$ and $R_7$ are independently selected from hydrogen, halogen, $C_{1-4}$alkyl, halo$C_{1-4}$alkyl, $C_{1-4}$alkoxy, —$SO_2$—$NR_{11}R_{12}$ and halo$C_{1-4}$alkoxy.

6. The compound according to claim 5, wherein $R_5$ is selected from halogen, $C_{1-4}$alkyl, halo$C_{1-4}$alkyl, $C_{1-4}$alkoxy, —$SO_2$—$NR_{11}R_{12}$ and halo$C_{1-4}$alkoxy; $R_3$ is selected from hydrogen, halogen and $C_{1-4}$alkyl; and $R_4$, $R_6$ and $R_7$ are hydrogen.

7. The compound according to claim 1, wherein $R_4$ and $R_5$ are connected to form a 5- or 6-membered cycloalkyl, wherein 1 or 2 methylene groups of the cycloalkyl are optionally replaced by O, said cycloalkyl is optionally substituted by one or more $C_{1-4}$alkyl, and $R_3$, $R_6$ and $R_7$ are hydrogen.

8. The compound according to claim 1, wherein $R_1$, $R_2$ and $R_9$ are hydrogen.

9. The compound according to claim 1, wherein $R_8$ is selected from —OH, $C_{1-4}$alkyl, $C_{3-6}$cycloalkyl$C_{1-4}$alkyl, —$C(O)C_{1-4}$alkyl, —$CONR_{13}R_{14}$ and —$C(NR_{15})NR_{11}R_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, said heterocycle is optionally substituted by one or more substituents independently selected from $C_{1-4}$alkyl and —$C(O)C_{1-2}$alkyl.

10. The compound according to claim 1, wherein n is 1 or 2 and each $R_{10}$ is independently selected from halogen, $C_{1-4}$alkyl and —$NR_{11}R_{12}$; or two $R_{10}$ attached to a common carbon atom form an oxo; or two $R_{10}$ attached to adjacent carbon atoms are connected to form a 3- to 5-membered cycloalkyl, said cycloalkyl is optionally substituted by one or more substituents independently selected from $C_{1-4}$alkyl and halogen.

11. The compound according to claim 1, wherein n is 0.

12. The compound according to claim 1, which is selected from the group consisting of:
N'-(4-fluorophenyl)-1,5-dimethypyrrolidine-2-carbohydrazide
(R)-2-(2-(4-fluorophenyl)hydrazinecarbonyl)pyrrolidine-1-carboxamide
(S)-2-(2-(4-fluorophenyl)hydrazinecarbonyl)pyrrolidine-1-carboxamide
2-(2-(4-fluorophenyl)hydrazinecarbonyl)pyrrolidine-1-carboxamide
2-(2-(4-fluoro-2-methylphenyl)hydrazine-1-carbonyl)pyrrolidine-1-carboxamide
2-(2-(3,5-difluorophenyl)hydrazinecarbonyl)pyrrolidine-1-carboxamide
2-(2-(4-(trifluoromethoxy)phenyl)hydrazinecarbonyl)pyrrolidine-1-carboxamide
2-(2-(4-(trifluoromethyl)phenyl)hydrazinecarbonyl)pyrrolidine-1-carboxamide
2-(2-(4-chloro-2-fluorophenyl)hydrazinecarbonyl)pyrrolidine-1-carboxamide
2-(2-(4-methoxyphenyl)hydrazinecarbonyl)pyrrolidine-1-carboxamide
2-(2-(2,3-dihydrobenzo[b][1,4]dioxin-6-yl)hydrazinecarbonyl)pyrrolidine-1-carboxamide
2-(2-(4-sulfamoylphenyl)hydrazinecarbonyl)pyrrolidine-1-carboxamide
(2S,4S)-4-fluoro-2-(2-(4-fluorophenyl)hydrazinecarbonyl)pyrrolidine-1-carboxamide
(R)-1-acetyl-N'-(4-fluorophenyl)pyrrolidine-2-carbohydrazide
N'-(4-fluorophenyl)-1-hydroxypyrrolidine-2-carbohydrazide
N'-(4-fluorophenyl)-1,2-dimethylpyrrolidine-2-carbohydrazide
2-(2-(4-fluorophenyl)hydrazinecarbonyl)-N,N-dimethylpyrrolidine-1-carboxamide
N'-(4-fluorophenyl)-1-(piperazine-1-carbonyl)pyrrolidine-2-carbohydrazide
1-(4-acetylpiperazine-1-carbonyl)-N'-(4-fluorophenyl)pyrrolidine-2-carbohydrazide
N'-(4-fluorophenyl)-1-(morpholine-4-carbonyl)pyrrolidine-2-carbohydrazide
N'-(4-fluorophenyl)-1-methyl-5-oxopyrrolidine-2-carbohydrazide
N'-(4-fluorophenyl)-1-methylpyrrolidine-2-carbohydrazide
4-amino-N'-(4-fluorophenyl)-1-methylpyrrolidine-2-carbohydrazide
4-fluoro-N'-(4-fluorophenyl)-1-methylpyrrolidine-2-carbohydrazide
(S)-1-(cyclopropylmethyl)-N'-(4-fluorophenyl)pyrrolidine-2-carbohydrazide
N'-(4-fluorophenyl)-3-methyl-3-azabicyclo[3.1.0]hexane-2-carbohydrazide
N'-(4-fluorophenyl)-1,4-dimethylpyrrolidine-2-carbohydrazide
N'-(4-fluorophenyl)-1,3-dimethylpyrrolidine-2-carbohydrazide
1-ethyl-N'-(4-fluorophenyl)pyrrolidine-2-carbohydrazide
2-(2-(4-fluorophenyl)hydrazinecarbonyl)pyrrolidine-1-carboximidamide or a pharmaceutically acceptable salt, or solvate thereof.

13. A method for treating an *A. baumannii* bacterial infection in a subject who has been infected with an *A. baumannii* infection, comprising administering to the subject an effective amount of a compound of formula (I):

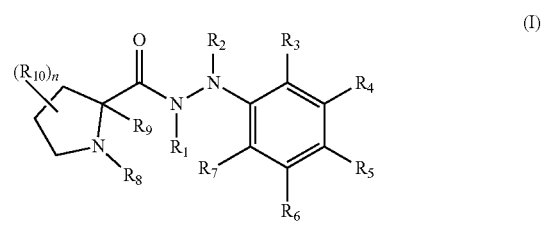

or a pharmaceutically acceptable salt or solvate thereof, wherein
$R_1$ and $R_2$ are independently selected from hydrogen, $C_{1-4}$alkyl, halo$C_{1-4}$alkyl and hydroxy$C_{1-4}$alkyl;
$R_3$, $R_4$, $R_5$, $R_6$ and $R_7$ are independently selected from hydrogen, —OH, halogen, $C_{1-6}$alkoxy, halo$C_{1-4}$alkoxy, —O$C_{3-6}$cycloalkyl$C_{0-4}$alkyl, $C_{1-6}$alkyl, $C_{3-6}$cycloalkyl$C_{0-4}$alkyl, halo$C_{1-6}$alkyl, hydroxy$C_{1-6}$alkyl, $C_{1-4}$alkoxy$C_{1-6}$alkyl, $C_{1-4}$alkoxy$C_{1-4}$alkoxy, —OCOR$_{11}$, —OS(O$_2$)R$_{11}$, —NR$_{11}$R$_{12}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CONR$_{11}$R$_{12}$, —S(O$_2$)NR$_{11}$R$_{12}$, —S(O$_2$)R$_{11}$, —CN and —CO$_2$R$_{11}$; or two of $R_3$ to $R_7$ attached to adjacent carbon atoms are connected to form a 5- or 6-membered cycloalkyl, wherein 1 or 2 methylene groups of the cycloalkyl are optionally replaced by O, said cycloalkyl is optionally substituted by one or more $C_{1-4}$alkyl or halo$C_{1-4}$alkyl;
$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl$C_{0-4}$alkyl, —C(O)$C_{1-4}$alkyl, —C(O)$C_{3-6}$cycloalkyl$C_{0-2}$alkyl, —CONR$_{13}$R$_{14}$, —C(NR$_{15}$)NR$_{11}$R$_{12}$ and —CO$_2$R$_{11}$;
$R_9$ is selected from hydrogen, $C_{1-4}$alkyl and halo$C_{1-4}$alkyl;
n is 0, 1, 2 or 3;
each $R_{10}$, if present, is independently selected from —OH, halogen, $C_{1-6}$alkyl, halo$C_{1-6}$alkyl, $C_{1-6}$alkoxy, $C_{1-4}$alkoxy$C_{1-6}$alkyl, —O$C_{3-6}$cycloalkyl$C_{0-4}$alkyl, —SR$_{11}$, —NR$_{11}$R$_{12}$, —OCOR$_{11}$, —OS(O$_2$)R$_{11}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CN, phenyl, 5- or 6-membered heteroaryl ring comprising 1 or 2 heteroatoms selected from N, O and S; wherein said phenyl and said heteroaryl ring are optionally substituted by one or more $C_{1-4}$alkyl or halo$C_{1-4}$alkyl; or two $R_{10}$ attached to a common carbon atom form an oxo; or two $R_{10}$ attached to a common carbon atom form a spiro $C_{3-6}$cycloalkyl, or two $R_{10}$ attached to adjacent carbon atoms are connected to form a 3- to 6-membered cycloalkyl, said cycloalkyl is optionally substituted by one or more substituents independently selected from $C_{1-4}$alkyl, $C_{1-4}$alkoxy, halo$C_{1-4}$alkyl and halogen;
each $R_{11}$ and $R_{12}$ are independently selected from hydrogen, $C_{1-4}$alkyl, halo$C_{1-4}$alkyl and $C_{3-6}$cycloalkyl$C_{0-4}$alkyl;
each $R_{13}$ and $R_{14}$ are independently selected from hydrogen, $C_{1-4}$alkyl, $C_{3-6}$cycloalkyl$C_{0-4}$alkyl and Het$_{3-6}$, wherein each $C_{1-4}$alkyl and $C_{3-6}$cycloalkyl$C_{0-4}$alkyl are optionally substituted by one or more $R_{16}$, and wherein each $C_{1-4}$alkyl are optionally substituted by one or more Het$_{3-6}$; or $R_{13}$ and $R_{14}$ form, together with the N atom to which they are attached, a 4- to 6-membered saturated heterocycle, which optionally contain one additional heteroatom selected from N, S and O, said heterocycle is optionally substituted by one or more substituents independently selected from $C_{1-4}$alkyl, halo$C_{1-4}$alkyl and —C(O)$C_{1-4}$alkyl;

$R_{15}$ is selected from hydrogen, $C_{1-6}$alkyl, halo$C_{1-6}$alkyl, —CN, —CONR$_{11}$R$_{12}$, —S(O$_2$)R$_{11}$, —SOR$_{11}$ and —S(O$_2$)NR$_{11}$R$_{12}$;

each $R_{16}$ is independently selected from alkyl, halogen, —CN, —CO$_2$R$_{11}$, —OR$_{11}$, —SR$_{11}$, —NR$_{17}$R$_{18}$, —CONR$_{17}$R$_{18}$ and —OCOR$_{11}$;

Het$_{3-6}$ is a 3- to 6-membered saturated monocyclic heterocyclic ring containing one heteroatom selected from O, S and N, wherein said ring is bonded to the rest of the molecule through any available C atom and wherein said ring can be optionally substituted by one or more substituents independently selected from $C_{1-4}$alkyl or halo$C_{1-4}$alkyl; and each $R_{17}$ and $R_{18}$ are independently selected from hydrogen, $C_{1-4}$alkyl and halo$C_{1-4}$alkyl, or $R_{17}$ and $R_{18}$ form, together with the N atom to which they are attached, a 4- to 6-membered saturated heterocycle, which optionally contains one additional heteroatom selected from N, S and O, said heterocycle is optionally substituted by one or more substituents independently selected from $C_{1-4}$alkyl and halo$C_{1-4}$alkyl;

and wherein the following products are excluded:

tert-butyl (S)-2-(2-phenylhydrazine-1-carbonyl)pyrrolidine-1-carboxylate, tert-butyl (R)-2-(1-methyl-2-phenylhydrazine-1-carbonyl)pyrrolidine-1-carboxylate, tert-butyl (2S,4S)-4-mercapto-2-(2-(3-sulfamoylphenyl)hydrazine-1-carbonyl) pyrrolidine-1-carboxylate, 3-(2-((2S,4S)-1-(tert-butoxycarbonyl)-4-mercaptopyrrolidine-2-carbonyl)hydrazinyl) benzoic acid, tert-butyl (2S,4S)-4-mercapto-2-(2-(2-(trifluoromethyl)phenyl)hydrazine-1-carbonyl) pyrrolidine-1-carboxylate, and tert-butyl (2S,4S)-2-(2-(2-chloro-5-(trifluoromethyl)phenyl)hydrazine-1-carbonyl)-4-mercaptopyrrolidine-1-carboxylate.

14. A pharmaceutical composition comprising a compound of formula (I):

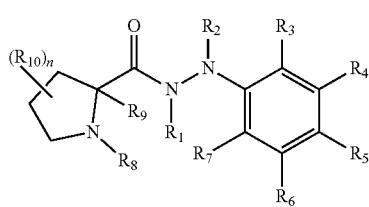

(I)

or a pharmaceutically acceptable salt or solvate thereof, wherein $R_1$ and $R_2$ are independently selected from hydrogen, $C_{1-4}$alkyl, halo$C_{1-4}$alkyl and hydroxy$C_{1-4}$alkyl;

$R_3$, $R_4$, $R_5$, $R_6$ and $R_7$ are independently selected from hydrogen, —OH, halogen, $C_{1-6}$alkoxy, halo$C_{1-6}$alkoxy, —OC$_{3-6}$cycloalkylC$_{0-4}$alkyl, $C_{1-6}$alkyl, $C_{3-6}$cycloalkyl $C_{0-4}$alkyl, halo$C_{1-6}$alkyl, hydroxy$C_{1-6}$alkyl, $C_{1-4}$alkoxy$C_{1-6}$alkyl, $C_{1-4}$alkoxy$C_{1-4}$alkoxy, —OCOR$_{11}$, —OS(O$_2$)R$_{11}$, —NR$_{11}$R$_{12}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CONR$_{11}$R$_{12}$, —S(O$_2$)NR$_{11}$R$_{12}$, —S(O$_2$)R$_{11}$, —CN and —CO$_2$R$_{11}$; or two of $R_3$ to $R_7$ attached to adjacent carbon atoms are connected to form a 5- or 6-membered cycloalkyl, wherein 1 or 2 methylene groups of the cycloalkyl are optionally replaced by O, said cycloalkyl is optionally substituted by one or more $C_{1-4}$alkyl or halo$C_{1-4}$alkyl;

$R_8$ is selected from —OH, $C_{1-6}$alkyl, halo$C_{1-6}$alkyl, hydroxy$C_{1-4}$alkyl, $C_{1-4}$alkoxy$C_{0-4}$alkyl, $C_{3-6}$cycloalkyl $C_{0-4}$alkyl, —C(O)$C_{1-4}$alkyl, —C(O)$C_{3-6}$cycloalkyl$C_{0-2}$alkyl, —CONR$_{13}$R$_{14}$, —C(NR$_{15}$)NR$_{11}$R$_{12}$ and —CO$_2$R$_{11}$;

$R_9$ is selected from hydrogen, $C_{1-4}$alkyl and halo$C_{1-4}$alkyl;

n is 0, 1, 2 or 3;

each $R_{10}$, if present, is independently selected from —OH, halogen, $C_{1-6}$alkyl, halo$C_{1-6}$alkyl, $C_{1-6}$alkoxy, $C_{1-4}$alkoxy$C_{1-6}$alkyl, —OC$_{3-6}$cycloalkylC$_{0-4}$alkyl, —SR$_{11}$, —NR$_{11}$R$_{12}$, —OCOR$_{11}$, —OS(O$_2$)R$_{11}$, —NR$_{11}$COR$_{12}$, —NR$_{11}$CO$_2$R$_{12}$, —NR$_{11}$S(O$_2$)R$_{12}$, —OCONR$_{11}$R$_{12}$, —CN, phenyl, 5- or 6-membered heteroaryl ring comprising 1 or 2 heteroatoms selected from N, O and S; wherein said phenyl and said heteroaryl ring are optionally substituted by one or more $C_{1-4}$alkyl or halo$C_{1-4}$alkyl; or two $R_{10}$ attached to a common carbon atom form an oxo; or two $R_{10}$ attached to a common carbon atom form a spiro $C_{3-6}$cycloalkyl, or two $R_{10}$ attached to adjacent carbon atoms are connected to form a 3- to 6-membered cycloalkyl, said cycloalkyl is optionally substituted by one or more substituents independently selected from $C_{1-4}$alkyl, $C_{1-4}$alkoxy, halo$C_{1-4}$alkyl and halogen;

each $R_{11}$ and $R_{12}$ are independently selected from hydrogen, $C_{1-4}$alkyl, halo$C_{1-4}$alkyl and $C_{3-6}$cycloalkyl$C_{0-4}$alkyl;

each $R_{13}$ and $R_{14}$ are independently selected from hydrogen, $C_{1-4}$alkyl, $C_{3-6}$cycloalkyl$C_{0-4}$alkyl and Het$_{3-6}$, wherein each $C_{1-4}$alkyl and $C_{3-6}$cycloalkyl$C_{0-4}$alkyl are optionally substituted by one or more $R_{16}$, and wherein each $C_{1-4}$alkyl are optionally substituted by one or more Het$_{3-6}$; or $R_{13}$ and $R_{14}$ form, together with the N atom to which they are attached, a 4- to 6-membered saturated heterocycle, which optionally contain one additional heteroatom selected from N, S and O, said heterocycle is optionally substituted by one or more substituents independently selected from $C_{1-4}$alkyl, halo $C_{1-4}$alkyl and —C(O)$C_{1-4}$alkyl;

$R_{15}$ is selected from hydrogen, $C_{1-6}$alkyl, halo$C_{1-6}$alkyl, —CN, —CONR$_{11}$R$_{12}$, —S(O$_2$)R$_{11}$, —SOR$_{11}$ and —S(O$_2$)NR$_{11}$R$_{12}$;

each $R_{16}$ is independently selected from alkyl, halogen, —CN, —CO$_2$R$_{11}$, —OR$_{11}$, —SR$_{11}$, —NR$_{17}$R$_{18}$, —CONR$_{17}$R$_{18}$ and —OCOR$_{11}$;

Het$_{3-6}$ is a 3- to 6-membered saturated monocyclic heterocyclic ring containing one heteroatom selected from O, S and N, wherein said ring is bonded to the rest of the molecule through any available C atom and wherein said ring is optionally substituted by one or more substituents independently selected from $C_{1-4}$alkyl or halo$C_{1-4}$alkyl; and each $R_{17}$ and $R_{18}$ are independently selected from hydrogen, $C_{1-4}$alkyl and halo$C_{1-4}$alkyl, or $R_{17}$ and $R_{18}$ form, together with the N atom to which they are attached, a 4- to 6-membered saturated heterocycle, which optionally contains one additional heteroatom selected from N, S and O, said heterocycle is optionally substituted by one or more substituents independently selected from $C_{1-4}$alkyl and halo$C_{1-4}$alkyl;

and at least one pharmaceutically acceptable excipient and/or carrier and wherein the following are excluded:

tert-butyl (S)-2-(2-phenylhydrazine-1-carbonyl)pyrrolidine-1-carboxylate, tert-butyl (R)-2-(1-methyl-2-phenylhydrazine-1-carbonyl) pyrrolidine-1-carboxylate, tert-butyl (2S,4S)-4-mercapto-2-(2-(3-sulfamoylphenyl)hydrazine-1-carbonyl) pyrrolidine-1-carboxylate, 3-(2-((2S,4S)-1-(tert-butoxycarbonyl)-4-mercaptopyrrolidine-2-carbonyl)hydrazinyl) benzoic acid, tert-butyl (2S,4S)-4-mercapto-2-(2-(2-(trifluoromethyl)phenyl)hydrazine-1-carbonyl) pyrrolidine-1-carboxylate, and tert-butyl (2S,4S)-2-(2-(2-chloro-5-(trifluoromethyl)phenyl)hydrazine-1-carbonyl)-4-mercaptopyrrolidine-1-carboxylate.

15. A process for the preparation of a compound of claim 1, comprising reacting a compound of formula (II)

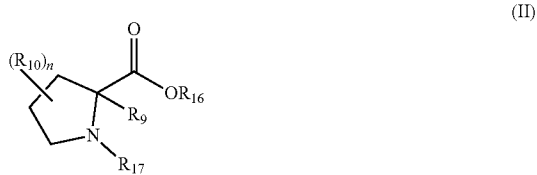

with a compound of formula (III) or a pharmaceutically acceptable salt or solvate thereof

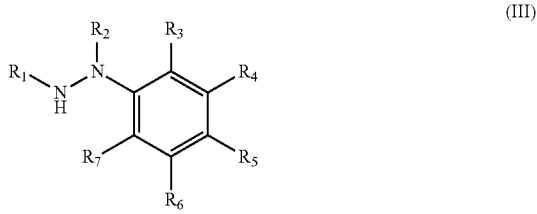

wherein $R_{16}$ is hydrogen or a $C_{1-4}$alkyl, $R_{17}$ is hydrogen or $R_8$, and n and $R_1$ to $R_{15}$ have the same meaning as described in claim 1.

16. The method according to claim 13, wherein
$R_1$, $R_2$ and $R_9$ are hydrogen;
$R_3$, $R_4$, $R_6$ and $R_7$ are independently selected from hydrogen, —OH, halogen, $C_{1-6}$ alkyl, $C_{3-6}$cycloalkyl$C_{0-4}$alkyl, —$NR_{11}R_{12}$, halo$C_{1-6}$alkyl, hydroxy$C_{1-6}$alkyl, $C_{1-4}$alkoxy$C_{0-6}$alkyl, $C_{1-4}$alkoxy$C_{1-4}$alkoxy, —$CONR_{11}R_{12}$, —$SO_2$—$NR_{11}R_{12}$, and halo$C_{1-4}$alkoxy, or two of $R_3$ to $R_7$ attached to adjacent carbon atoms are connected to form a 5- or 6-membered cycloalkyl, wherein 1 or 2 methylene groups of the cycloalkyl are optionally replaced by O, said cycloalkyl is optionally substituted by one or more $C_{1-4}$alkyl;
$R_5$ is selected from halogen, $C_{1-4}$alkyl, halo$C_{1-4}$alkyl, $C_{1-4}$alkoxy, —$SO_2$—$NR_{11}R_{12}$ and halo$C_{1-4}$alkoxy; $R_3$ is selected from hydrogen, halogen and $C_{1-4}$alkyl; and $R_4$, $R_6$ and $R_7$ are hydrogen;
at least one of $R_3$ to $R_7$ is not hydrogen and at least two of $R_3$ to $R_7$ are hydrogen;
$R_8$ is selected from —OH, $C_{1-4}$alkyl, $C_{3-6}$cycloalkyl $C_{1-4}$alkyl, —$C(O)C_{1-4}$alkyl, —$CONR_{13}R_{14}$ and —$C(NR_{15})NR_{11}R_{12}$; wherein each $R_{13}$ and $R_{14}$ are independently selected from hydrogen and $C_{1-4}$alkyl, or $R_{13}$ and $R_{14}$ form, together with the N atom to which they are attached, a 6-membered saturated heterocycle, which contains one additional heteroatom selected from N and O, said heterocycle is optionally substituted by one or more substituents independently selected from $C_{1-4}$alkyl and —$C(O)C_{1-2}$alkyl;
n is 1 or 2 and each $R_{10}$ is independently selected from halogen, $C_{1-4}$alkyl and —$NR_{11}R_{12}$; or two $R_{10}$ attached to a common carbon atom form an oxo; or two $R_{10}$ attached to adjacent carbon atoms are connected to form a 3- to 5-membered cycloalkyl, said cycloalkyl is optionally substituted by one or more substituents independently selected from $C_{1-4}$alkyl and halogen; or n is 0;
each $R_{11}$ and $R_{12}$ are independently selected from hydrogen and $C_{1-4}$alkyl; and
$R_{15}$ is selected from hydrogen, $C_{1-6}$alkyl, halo$C_{1-6}$alkyl, —CN, —$CONR_{11}R_{12}$, —$SO_2$—$R_{11}$, —SO—$R_{11}$ and —$SO_2$—$NR_{11}R_{12}$.

17. The method according to claim 13, wherein the compound is selected from the group consisting of:

N'-(4-fluorophenyl)-1,5-dimethypyrrolidine-2-carbohydrazide (R)-2-(2-(4-fluorophenyl)hydrazinecarbonyl)pyrrolidine-1-carboxamide (S)-2-(2-(4-fluorophenyl)hydrazinecarbonyl)pyrrolidine-1-carboxamide 2-(2-(4-fluorophenyl)hydrazinecarbonyl)pyrrolidine-1-carboxamide 2-(2-(4-fluoro-2-methylphenyl)hydrazine-1-carbonyl)pyrrolidine-1-carboxamide 2-(2-(3,5-difluorophenyl)hydrazinecarbonyl)pyrrolidine-1-carboxamide 2-(2-(4-(trifluoromethoxy)phenyl)hydrazinecarbonyl)pyrrolidine-1-carboxamide 2-(2-(4-(trifluoromethyl)phenyl)hydrazinecarbonyl)pyrrolidine-1-carboxamide 2-(2-(4-chloro-2-fluorophenyl)hydrazinecarbonyl)pyrrolidine-1-carboxamide 2-(2-(4-methoxyphenyl)hydrazinecarbonyl)pyrrolidine-1-carboxamide 2-(2-(2,3-dihydrobenzo[b][1,4]dioxin-6-yl)hydrazinecarbonyl)pyrrolidine-1-carboxamide 2-(2-(4-sulfamoylphenyl)hydrazinecarbonyl)pyrrolidine-1-carboxamide (2S,4S)-4-fluoro-2-(2-(4-fluorophenyl)hydrazinecarbonyl)pyrrolidine-1-carboxamide (R)-1-acetyl-N'-(4-fluorophenyl)pyrrolidine-2-carbohydrazide N'-(4-fluorophenyl)-1-hydroxypyrrolidine-2-carbohydrazide N'-(4-fluorophenyl)-1,2-dimethylpyrrolidine-2-carbohydrazide 2-(2-(4-fluorophenyl)hydrazinecarbonyl)-N,N-dimethylpyrrolidine-1-carboxamide N'-(4-fluorophenyl)-1-(piperazine-1-carbonyl)pyrrolidine-2-carbohydrazide 1-(4-acetylpiperazine-1-carbonyl)-N'-(4-fluorophenyl) pyrrolidine-2-carbohydrazide N'-(4-fluorophenyl)-1-(morpholine-4-carbonyl)pyrrolidine-2-carbohydrazide N'-(4-fluorophenyl)-1-methyl-5-oxopyrrolidine-2-carbohydrazide N'-(4-fluorophenyl)-1-methylpyrrolidine-2-carbohydrazide 4-amino-N'-(4-fluorophenyl)-1-methylpyrrolidine-2-carbohydrazide 4-fluoro-N'-(4-fluorophenyl)-1-methylpyrrolidine-2-carbohydrazide (S)-1-(cyclopropylmethyl)-N'-(4-fluorophenyl)pyrrolidine-2-carbohydrazide N'-(4-fluorophenyl)-3-methyl-3-azabicyclo[3.1.0]hexane-2-carbohydrazide N'-(4-fluorophenyl)-1,4-dimethylpyrrolidine-2-carbohydrazide N'-(4-fluorophenyl)-1,3-dimethylpyrrolidine-2-carbohydrazide 1-ethyl-N'-(4-fluorophenyl)pyrrolidine-2-carbohydrazide
2-(2-(4-fluorophenyl)hydrazinecarbonyl)pyrrolidine-1-carboximidamide or a pharmaceutically acceptable salt, or solvate thereof.

18. The method according to claim 13, wherein the compound is administered in combination with one or more other antibacterial agents.

19. The method according to claim 18, wherein the compound is combined with another antibacterial agent by chemically bonding both compounds to form a single molecule.

* * * * *